(12) United States Patent
Arline et al.

(10) Patent No.: US 10,933,061 B2
(45) Date of Patent: Mar. 2, 2021

(54) PYRVINIUM PAMOATE THERAPIES AND METHODS OF USE

(71) Applicant: Shepherd Therapeutics, Inc., Natick, MA (US)

(72) Inventors: Katherine Arline, Cambridge, MA (US); Jamie Dempsey Barber, Hanover, MA (US); William M. Siders, Franklin, MA (US); Johanne Kaplan, Sherborn, MA (US)

(73) Assignee: Shepherd Therapeutics, Inc., Natick, MA (US)

( * ) Notice: Subject to any disclaimer, the term of this patent is extended or adjusted under 35 U.S.C. 154(b) by 0 days.

(21) Appl. No.: 16/229,783

(22) Filed: Dec. 21, 2018

(65) Prior Publication Data
US 2019/0209549 A1 Jul. 11, 2019

Related U.S. Application Data

(60) Provisional application No. 62/636,553, filed on Feb. 28, 2018, provisional application No. 62/609,104, filed on Dec. 21, 2017.

(51) Int. Cl.
| | | |
|---|---|---|
| *A61K 31/4709* | (2006.01) | |
| *A61K 45/06* | (2006.01) | |
| *A61P 35/00* | (2006.01) | |
| *A61P 35/04* | (2006.01) | |
| *A61K 47/61* | (2017.01) | |
| *A61K 31/282* | (2006.01) | |
| *A61K 31/4745* | (2006.01) | |
| *A61K 31/44* | (2006.01) | |
| *A61K 31/704* | (2006.01) | |
| *A61K 31/7048* | (2006.01) | |
| *A61K 33/242* | (2019.01) | |
| *A61K 31/475* | (2006.01) | |
| *A61K 31/337* | (2006.01) | |
| *A61K 31/513* | (2006.01) | |
| *A61K 31/675* | (2006.01) | |
| *A61K 31/555* | (2006.01) | |
| *A61K 31/506* | (2006.01) | |
| *A61K 31/655* | (2006.01) | |
| *A61K 31/7068* | (2006.01) | |
| *A61K 47/69* | (2017.01) | |
| *A61K 31/495* | (2006.01) | |
| *A61K 31/517* | (2006.01) | |
| *A61K 47/68* | (2017.01) | |
| *A61K 9/127* | (2006.01) | |
| *A61K 47/36* | (2006.01) | |

(52) U.S. Cl.
CPC ......... *A61K 31/4709* (2013.01); *A61K 9/127* (2013.01); *A61K 31/282* (2013.01); *A61K 31/337* (2013.01); *A61K 31/44* (2013.01); *A61K 31/475* (2013.01); *A61K 31/4745* (2013.01); *A61K 31/495* (2013.01); *A61K 31/506* (2013.01); *A61K 31/513* (2013.01); *A61K 31/517* (2013.01); *A61K 31/555* (2013.01); *A61K 31/655* (2013.01); *A61K 31/675* (2013.01); *A61K 31/704* (2013.01); *A61K 31/7048* (2013.01); *A61K 31/7068* (2013.01); *A61K 33/242* (2019.01); *A61K 45/06* (2013.01); *A61K 47/36* (2013.01); *A61K 47/61* (2017.08); *A61K 47/6801* (2017.08); *A61K 47/6937* (2017.08); *A61P 35/00* (2018.01); *A61P 35/04* (2018.01)

(58) Field of Classification Search
CPC .................................................. A61K 31/4709
See application file for complete search history.

(56) References Cited

U.S. PATENT DOCUMENTS

| | | | |
|---|---|---|---|
| 2,925,417 A | | 2/1960 | Elslager et al. |
| 4,522,811 A | | 6/1985 | Eppstein et al. |
| 6,395,299 B1 | | 5/2002 | Babich et al. |
| 8,323,698 B2 | | 12/2012 | Gu et al. |
| 8,367,113 B2 | | 2/2013 | Gu et al. |
| 8,580,773 B2 | | 11/2013 | Diamond et al. |
| 8,632,510 B2 | | 1/2014 | Ferrari et al. |
| 8,697,098 B2 | | 4/2014 | Perumal et al. |
| 8,790,650 B2 | | 7/2014 | Lee et al. |
| 9,532,956 B2 | | 1/2017 | Radovic-Moreno et al. |
| 9,549,965 B2 | | 1/2017 | Hu et al. |
| 9,618,513 B2 | | 4/2017 | Zou et al. |
| 2003/0059471 A1* | | 3/2003 | Compton ............. A61K 9/1694 424/489 |

(Continued)

FOREIGN PATENT DOCUMENTS

| | | |
|---|---|---|
| CN | 103664876 B | 4/2016 |
| EP | 2 980 585 A1 | 2/2016 |

(Continued)

OTHER PUBLICATIONS

American Cancer Society, "Special Section: Rare Cancers in Adults," Cancer Facts & Figures 2017, pp. 30-39, retrieved from: https://www.cancer.org/content/dam/cancer-org/research/cancer-facts-and-statistics/annual-cancer-facts-and-figures/2017/cancer-facts-and-figures-2017-special-section-rare-cancers-in-adults.pdf.

(Continued)

*Primary Examiner* — Yong S. Chong
(74) *Attorney, Agent, or Firm* — Cooley LLP; Heidi A. Erlacher; Jessica D. Cande

(57) ABSTRACT

The disclosure relates to a method of treating cancer by administering to the subject a therapeutically effective amount of a composition comprising pyrvinium pamoate, optionally in combination with at least one additional therapeutic agent or modality.

31 Claims, 18 Drawing Sheets

(56) References Cited

U.S. PATENT DOCUMENTS

| | | |
|---|---|---|
| 2003/0068365 A1 | 4/2003 | Suvanprakorn et al. |
| 2007/0093462 A1 | 4/2007 | Rogers et al. |
| 2008/0293766 A1 | 11/2008 | Diamond et al. |
| 2009/0023673 A1 | 1/2009 | Manoharan et al. |
| 2009/0099062 A1 | 4/2009 | Lee et al. |
| 2010/0144845 A1 | 6/2010 | Farokhzad et al. |
| 2011/0144043 A1 | 6/2011 | Frank |
| 2011/0263693 A1 | 10/2011 | Vinson-Hieronymus et al. |
| 2011/0287953 A1 | 11/2011 | Huang et al. |
| 2012/0052053 A1 | 3/2012 | Manning-Bog et al. |
| 2012/0064008 A1 | 3/2012 | Zetter et al. |
| 2012/0082659 A1 | 4/2012 | Land et al. |
| 2012/0283120 A1 | 11/2012 | Watanabe et al. |
| 2012/0302624 A1 | 11/2012 | Lai |
| 2012/0318262 A1 | 12/2012 | Lee et al. |
| 2014/0005379 A1 | 1/2014 | Gu |
| 2017/0042857 A1 | 2/2017 | Yarden et al. |
| 2017/0056347 A1 | 3/2017 | Glick et al. |
| 2017/0112829 A1 | 4/2017 | Baeyens-Cabrera et al. |

FOREIGN PATENT DOCUMENTS

| | | |
|---|---|---|
| JP | 2004-189712 A | 7/2004 |
| JP | 2005-029480 A | 2/2005 |
| JP | 6124389 B2 | 4/2017 |
| WO | WO 98/046286 A1 | 10/1998 |
| WO | WO 2006/078754 A1 | 7/2006 |
| WO | WO 2007/117466 A2 | 10/2007 |
| WO | WO 2008/150845 A1 | 12/2008 |
| WO | WO 2008/156644 A2 | 12/2008 |
| WO | WO 2010/101649 A2 | 9/2010 |
| WO | WO 2014/089160 A1 | 6/2014 |
| WO | WO 2015/009851 A1 | 1/2015 |
| WO | WO 2015/079413 A2 | 6/2015 |
| WO | WO 2015/120543 A1 | 8/2015 |
| WO | WO 2016/187544 A1 | 11/2016 |
| WO | WO 2016/191695 A2 | 12/2016 |
| WO | WO 2016/210330 A1 | 12/2016 |
| WO | WO 2017/048800 A1 | 3/2017 |
| WO | WO 2017/136515 A1 | 8/2017 |
| WO | WO 2017/151786 A1 | 9/2017 |
| WO | WO 2009/003147 A1 | 12/2018 |

OTHER PUBLICATIONS

Arline et al., "Rare Isn't Rare—Rare cancers compose up to 50% of all U.S. diagnoses," Poster, AACR 2018, 1 page.

Arline et al., "Rare Isn't Rare: Rare cancers compose up to 50% of all U.S. diagnoses," Abstract 1198, AACR Annual Meeting 2018; Apr. 14-18, 2018, 2 pages.

Center for Disease Control National Center for Health Statistics, "Cancer," CDC/National Center for Health Statistics, May 3, 2017, 2 pages, retrieved from: https://www.cdc.gov/nchs/fastats/cancer.htm.

Chen, B. et al., "Reversal of cancer gene expression correlates with drug efficacy and reveals therapeutic targets," Nature Communications, 2017, 8: 16022, 12 pages.

Chou, T.C., "Drug Combination Studies and Their Synergy Quantification Using the Chou-Talalay Method," Cancer Research; 2010, 70(2); 440-446.

Dabrowska et al., "How FDA Approves Drugs and Regulates Their Safety and Effectiveness," Congressional Research Service, May 8, 2018, Jul. 5700, R41983, 31 pages.

Deng, L. et al., "Pyrvinium targets autophagy addiction to promote cancer cell death," Cell Death and Disease (2013) 4, e614, 10 pages.

DiMasi et al., "Innovation in the pharmaceutical industry: New estimates of R&D costs," Journal of Health Economics (May 2016) 47:20-33.

Drugs.com, "Pyrvinium (Oral-Local)," (Mar. 17, 2000) 6 pages, retrieved from https://www.drugs.com/mmx/pyrvinium-pamoate.html on Mar. 13, 2019.

Esumi, H. et al., "Antitumor activity of pyrvinium pamoate, 6-(dimethylamino)-2-[2-(2,5-dimethyl-1-phenyl-1H-pyrrol-3-yl)ethenyl]-1-methyl-quinolinium pamoate salt, showing preferential cytotoxicity during glucose starvation," (2004) Cancer Sci, 95: 685-690.

EvaluatePharma, "Orphan Drug Report 2017," Feb. 2017, 4th Edition, 26 pages, retrieved from: http://info.evaluategroup.com/rs/607-YGS-364/images/EPOD17.pdf.

Ford, C.E., et al., "Wnt signalling in gynaecological cancers: A future target for personalised medicine?" Gynecologic Oncology (Feb. 2016) 140, No. 2 :345-351.

Genetic and Rare Diseases Information Center (GARD), "Rare Cancers," 14 pages, retrieved from https://rarediseases.info.nih.gov/diseases/diseases-by-category/1/rarecancers on Feb. 21, 2019.

Greenlee, R.T. et al., "The Occurrence of Rare Cancers in U.S. Adults, 1995-2004," Public Health Rep., Jan.-Feb. 2010;125(1):28-43.

Gu, L. et al, "A Combination RNAi-Chemotherapy Layer-byLayer Nanoparticle for Systemic Targeting of KRAS/P53 with Cisplatin to Treat Non—Small Cell Lung Cancer," Clinical Cancer Research; 23(23) Dec. 1, 2017, DOI:10.1158/1078-0432.CCR-16-2186; 13 pages.

Harada, Y. et al., "Pyrvinium pamoate inhibits proliferation of myeloma/erythroleukemia cells by suppressing mitochondrial respiratory complex 1 and STAT3," Cancer Letters (2012) 319: 83-88.

Ishii, I. et al., "Reprofiling a classical anthelmintic, pyrvinium pamoate, as an anti-cancer drug targeting mitochondrial respiration," Frontiers in Oncology, Oct. 2012, vol. 2, Article 137, 4 pages.

Keshavan, M., "Database sleuths turn up a surprising new drug to test against cancer," STAT+, Jul. 13, 2017, 3 pages.

Kesselheim et al., "Trends in utilization of FDA expedited drug development and approval programs, 1987-2014: cohort study," BMJ 2015;351:h4633; 7 pages.

Li, B. et al., "Pyrvinium Attenuates Hedgehog Signaling Downstream of Smoothened," Cancer Res; 2014, 74(17); 4811-4821.

Li, B. et al., "Repurposing the FDA-Approved Pinworm Drug Pyrvinium as a Novel Chemotherapeutic Agent for Intestinal Polyposis," PLoS ONE, 2014, 9(7): e101969; 9 pages.

Li, Y. et al., "Selective killing of cancer cells by β-lapachone: Direct checkpoint activation as a strategy against cancer," PNAS 100(5): 2674-2678, 2003.

Macmillan Cancer Support, "What is rare cancer?" retrieved from: https://www.macmillan.org.uk/information-and-support/audience/rare-cancers/what-is-rare-cancer.html on Feb. 26, 2019, 4 pages.

Mayo Clinic, "Pyrvinium (Oral Route)," Feb. 1, 2019, 5 pages, retrieved from: https://www.mayoclinic.org/drugs-supplements/pyrvinium-oral-route/side-effects/drg-20065693.

Mihaela Catalina Stanciu Foundation for Life, "Pyrvinium Pamoate: An Anti Worm Drug with Important Anti Cancer Potential," Mihaela Catalina Stanciu Foundation for Life, Mar. 12, 2016, 16 pages, retrieved from: https://www.cancertreatmentsresearch.com/pyrvinium-pamoate/.

National Cancer Institute, "Common Cancer Types," Feb. 21, 2019, 2 pages, retrieved from: https://www.cancer.gov/types/common-cancers.

National Cancer Institute, "Targeted Cancer Therapies Fact Sheet," Feb. 6, 2019, 8 pages, retrieved from: https://www.cancer.gov/about-cancer/treatment/types/targeted-therapies/targeted-therapies-fact-sheet.

National Cancer Institute, "Targeted Therapy to Treat Cancer", Nov. 28, 2018, 4 pages, retrieved from: https://www.cancer.gov/about-cancer/treatment/types/targeted-therapies.

Saraswati, S. et al., "Pyrvinium, a Potent Small Molecule WNT Inhibitor, Increases Engraftment and Inhibits Lineage Commitment of Mesenchymal Stem Cells (MSCs)," Wound Repair Regen. 2012; 20(2): 185-193; 16 pages provided.

Sertkaya, A. et al., "Key cost drivers of pharmaceutical clinical trials in the United States," Clinical Trials 2016, 13(2):117-126.

Sigma-Aldrich, "Pyrvinium pamoate salt hydrate," 4 pages, retrieved from https://www.sigmaaldrich.com/catalog/product/sigma/p0027?lang=en&region=US on Mar. 13, 2019.

(56) References Cited

OTHER PUBLICATIONS

Sugimoto, K. et al., "Discovery of a drug targeting microenvironmental support for lymphoma cells by screening using patient-derived xenograft cells," Scientific Reports, 2015, 5:13054, 12 pages.

The ASCO Post, "One in Five Cancers Diagnosed in the United States Is a Rare Cancer," May 23, 2017, 2 pages, retrieved from: http://www.ascopost.com/News/55663.

Thorne, C. et al., "Small-molecule inhibition of Wnt signaling through activation of casein kinase 1α," Nat Chem Biol. Nov. 2010; 6(11): 829-836; 19 pages provided.

Toxnet, "Pyrvinium," Toxicology Data Network, Nov. 8, 2002, 8 pages, retrieved from: https://toxnet.nlm.nih.gov/cgi-bin/sis/search/a?dbs+hsdb:@term+@DOCNO+3178.

Venugopal, C. et al., "Pyrvinium Targets CD133 in Human Glioblastoma Brain Tumor-Initiating Cells," Clinical Cancer Research; 2015, 21(23); 5324-5337.

Wiegering, A. et al., "The impact of pyrvinium pamoate on colon cancer cell viability," Int J Colorectal Dis (2014) 29:1189-1198.

Xiang, W. et al., "Pyrvinium selectively targets blast phase-chronic myeloid leukemia through inhibition of mitochondrial respiration," Oncotarget, 2015, vol. 6, No. 32, pp. 33769-33780.

Xu, L. et al., "WNT pathway inhibitor pyrvinium pamoate inhibits the self-renewal and metastasis of breast cancer stem cells," International Journal of Oncology, 2016, 48: 1175-1186.

Xu, W. et al., "The Antihelmintic Drug Pyrvinium Pamoate Targets Aggressive Breast Cancer," PLoS ONE, 2013, 8(8): e71508, 12 pages.

Yu, D. et al., "Pyrvinium Targets the Unfolded Protein Response to Hypoglycemia and Its Anti-Tumor Activity Is Enhanced by Combination Therapy," PLoS ONE, 2008, 3(12): e3951, 10 pages.

Database EMBASE, "The antiproliferative properties of pyrvinium pamoate on human adrenocortical carcinoma cells," EMBASE Database accession No. 0052542328, May 2, 2017, 2 pages.

\* cited by examiner

FIG. 12

Exposure level of PP following a single injection of 1 mg/kg of PP encapsulated nanoparticle

FIG. 15

| | Pyrvinium Pamoate | | | | |
|---|---|---|---|---|---|
| | 0.0044 µM | 0.013 µM | 0.04 µM | 0.12 µM | 0.36 µM |
| 0.02 µM | 0.925 | 1.025 | 1.077 | 1.303 | 0.675 |
| 0.06 µM | 1.445 | 1.476 | 1.090 | 0.961 | 0.494 |
| 0.18 µM | 1.749 | 1.667 | 1.162 | 0.761 | 0.164 |
| 0.54 µM | 0.766 | 0.725 | 0.549 | 0.252 | 0.106 |
| 1.62 µM | 0.650 | 0.631 | 0.366 | 0.316 | 0.269 |
| Chemo therapy | | | | | |

FIG. 16

Chou Talalay

| | | Pyrvinium Pamoate | | | | |
|---|---|---|---|---|---|---|
| | 0.0 uM | 0.0067 uM | 0.021 uM | 0.06 uM | 0.18 uM | 0.54 uM |
| Paclitaxel | 0.0008 uM | 1.0759 | 0.5478 | | | 0.8195 |
| | 0.0024 uM | 0.4633 | | | | 0.7455 |
| | 0.0024 uM | 0.5487 | 0.3221 | | | 0.7596 |
| | 0.0072 uM | 0.5792 | 0.5052 | | | 0.7032 |
| | 0.0216 uM | 0.6945 | 0.8313 | 0.316 | | 0.7067 |

PYRVINIUM PAMOATE THERAPIES AND METHODS OF USE

RELATED APPLICATIONS

This application claims priority to U.S. Application No. 62/609,104, filed on Dec. 21, 2017 and U.S. Application No. 62/636,553, filed on Feb. 28, 2018, the contents of each of which are herein incorporated by reference in their entirety.

FIELD OF THE DISCLOSURE

The disclosure relates to the fields of molecular biology, oncology and human therapeutics for the treatment of cancer.

BACKGROUND

Cancer is a proliferative disease in which the cells of a subject grow abnormally and in an uncontrolled way, in some cases leading to the death of the subject with cancer. There are many independent events and causes which can lead to cancer, and many different cell types and tissues that can give rise to cancers. As such, treatments developed for one type of cancer may not work on another type of cancer. Despite many years of research, and a plethora of treatments available to cancer sufferers, there is still a long felt need in the art for additional cancer therapies. This need is particularly acute in rare cancers, which in many cases may be under-resourced because of their rarity. The disclosure provides additional methods for the treatment of cancer.

SUMMARY

The disclosure provides methods of treating a cancer in a subject in need thereof, comprising administering to the subject a therapeutically effective amount of a composition comprising 3-carboxy-1-[(3-carboxy-2-oxidonaphthalen-1-yl)methyl]naphthalen-2-olate; 2-[(E)-2-(2,5-dimethyl-1-phenylpyrrol-3-yl)ethenyl]-N,N,1-trimethylquinolin-1-ium-6-amine (pyrvinium pamoate).

The disclosure provides compositions for use in treating cancer in a subject in need thereof, comprising a therapeutically effective amount of a composition comprising pyrvinium pamoate.

The disclosure provides compositions for use in the manufacture of a medicament for the prevention or treatment of cancer, comprising a therapeutically effective amount of a composition comprising pyrvinium pamoate.

In some embodiments of the methods or compositions for use of the disclosure, the composition comprising pyrvinium pamoate comprises a salt or a salt hydrate. In some embodiments, the salt comprises an anhydrous dipyrvinium pamoate salt.

In some embodiments of the methods or compositions for use of the disclosure, the composition comprising pyrvinium pamoate further comprises a nanoparticle. In some embodiments, the nanoparticle comprises a liposome, a micelle, a polymer-based nanoparticle, a lipid-polymer based nanoparticle, a metal based nanoparticle, a nanocrystal, a carbon nanotube based nanoparticle or a polymeric micelle. In some embodiments, the polymer-based nanoparticle comprises a multiblock copolymer, a diblock copolymer, a polymeric micelle or a hyperbranched macromolecule. In some embodiments, the polymer-based nanoparticle comprises a multiblock copolymer a diblock copolymer. In some embodiments, the polymer-based nanoparticle comprises a poly(lactic-co-glycolic acid) PLGA polymer. In some embodiments, the polymer-based nanoparticle is pH responsive. In some embodiments, the polymer-based nanoparticle further comprises a buffering component. In some embodiments, the nanoparticle further comprises a targeting agent. In some embodiments, the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment. In some embodiments, the targeting agent comprises hyaluronic acid (HA). In some embodiments, the targeting agent binds to the surface of a cell of the cancer of the subject. In some embodiments, the HA binds to CD44 on the surface of the cancer of the subject. In some embodiments, the targeting agent increases uptake of the nanoparticle by a cancer cell of the subject.

In some embodiments of the methods or compositions for use of the disclosure, the cancer comprises a colon cancer, a breast cancer, a liver cancer, a lung cancer, a brain cancer, a pancreatic cancer or a renal cancer. In some embodiments, the lung cancer comprises a small cell lung cancer or a non-small cell lung cancer.

In some embodiments of the methods or compositions for use of the disclosure, the cancer is a rare cancer. In some embodiments, the rare cancer is a blastoma, a glioma, a sarcoma, a carcinoma, a neuroendocrine cancer, a mesothelioma, a chordoma or a thymic cancer. In some embodiments, the blastoma comprises a neuroblastoma.

In some embodiments of the methods or compositions for use of the disclosure, the cancer is a rare cancer. In some embodiments, the rare cancer is a blastoma, a sarcoma, a carcinoma, a neuroendocrine cancer, a mesothelioma, a chordoma, thymic cancer, a gastrointestinal stromal tumor or a pheochromocytoma. In some embodiments, the sarcoma comprises an Ewing's sarcoma, a leiomyosarcoma, an angiosarcoma or a rhabdomyosarcoma.

In some embodiments of the methods or compositions for use of the disclosure, the cancer is a rare cancer. In some embodiments, the rare cancer is a blastoma, a sarcoma, a carcinoma, a neuroendocrine cancer, a mesothelioma, a chordoma or a thymic cancer. In some embodiments, the carcinoma comprises an adenoid cystic carcinoma (ACC), a uterine serous carcinoma, a cholangiocarcinoma, a colorectal carcinoma, an esophageal carcinoma, a hepatocellular carcinoma, a pancreatic carcinoma, a small cell lung carcinoma, an adrenocortical carcinoma, an ovarian carcinoma, a gastric carcinoma or a thymic carcinoma. In some embodiments, the ovarian carcinoma comprises an endometrioid or epithelial ovarian carcinoma. In some embodiments, the adenoid cystic carcinoma (ACC) comprises a salivary gland cell, a trachea cell, a lacrimal gland cell, a skin cell or a vulval cell.

In some embodiments of the methods or compositions for use of the disclosure, the cancer is a rare cancer. In some embodiments, the rare cancer is a blastoma, a sarcoma, a carcinoma, a neuroendocrine cancer, a mesothelioma, a chordoma or a thymic cancer. In some embodiments, the neuroendocrine cancer comprises an adrenocortical carcinoma, a carcinoid tumor or a thymic cancer. In some embodiments, the thymic cancer comprises a thymoma or a thymic carcinoma.

In some embodiments of the methods or compositions for use of the disclosure, the cancer is a rare cancer. In some embodiments, the rare cancer is a blastoma, a sarcoma, a carcinoma, a neuroendocrine cancer, a mesothelioma, a chordoma or a thymic cancer. In some embodiments, the neuroendocrine cancer comprises an adrenocortical carcinoma, a carcinoid tumor or a thymic cancer. In some embodiments, the carcinoid tumor comprises a small intestine tumor, an appendix tumor, a tumor of the bronchial system, a brain tumor, colon tumor, a stomach tumor, a gallbladder tumor, a bile duct tumor, an ovarian tumor, a testicular tumor, a bladder tumor, a kidney tumor, a thymic tumor, an eye tumor or an ear tumor.

In some embodiments of the methods or compositions for use of the disclosure, the method of treatment or use of the composition further comprises administering at least one other chemotherapeutic agent.

In some embodiments of the methods or compositions for use of the disclosure, the composition comprising pyrvinium pamoate and the at least one other chemotherapeutic agent exhibit synergy. In some embodiments, the synergy is measured using the Chou-Talalay method in at least one cancer cell line. In some embodiments, the synergy comprises a CI of less than 0.9 when measured at at least three concentrations of the composition comprising pyrvinium pamoate and the at least one other chemotherapeutic agent in at least one cancer cell line.

In some embodiments of the methods or compositions for use of the disclosure, the at least one other chemotherapeutic agent comprises a taxane. In some embodiments, the taxane comprises Paclitaxel or Docetaxel.

In some embodiments of the methods or compositions for use of the disclosure, the at least one other chemotherapeutic agent comprises a Vinca alkaloid. In some embodiments, the Vinca alkaloid comprises Vinblastine, Vincristine or Vinorelbine.

In some embodiments of the methods or compositions for use of the disclosure, the at least one other chemotherapeutic agent comprises a platinum based antineoplastic drug. In some embodiments, the platinum based antineoplastic drug comprises Cisplatin, Carboplatin or Oxaliplatin.

In some embodiments of the methods or compositions for use of the disclosure, the at least one other chemotherapeutic agent comprises a Topoisomerase inhibitor. In some embodiments, the topoisomerase inhibitor comprises Irinotecan or Etoposide.

In some embodiments of the methods or compositions for use of the disclosure, the at least one other chemotherapeutic agent comprises a thymidylate synthase inhibitor. In some embodiments, the thymidylate synthase inhibitor comprises 5-Fluorouracil (5-FU).

In some embodiments of the methods or compositions for use of the disclosure, the at least one other chemotherapeutic agent comprises a DNA intercalating agent. In some embodiments, the DNA intercalating agent comprises Doxorubicin.

In some embodiments of the methods or compositions for use of the disclosure, the at least one other chemotherapeutic agent comprises a DNA alkylating agent. In some embodiments, the DNA alkylating agent comprises Dacarbazine, Temozolomide, Cyclophosphamide or Ifosfamide. In some embodiments, the DNA alkylating agent comprises Temozolomide.

In some embodiments of the methods or compositions for use of the disclosure, the at least one other chemotherapeutic agent comprises an agent that binds to DNA and causes DNA damage.

In some embodiments of the methods or compositions for use of the disclosure, the at least one other chemotherapeutic agent comprises a cyclin dependent kinase (CDK) inhibitor. In some embodiments, the CDK inhibitor comprises an inhibitor of CDK4, an inhibitor of CDK6 or an inhibitor of CDK4 and CDK6. In some embodiments, the CDK inhibitor comprises Abemaciclib (Verzenio), Palbociclib (Ibrance) or Ribociclib (Kisqali).

In some embodiments of the methods or compositions for use of the disclosure, the at least one other chemotherapeutic agent comprises a mechanistic target of rapamycin kinase (mTOR) inhibitor. In some embodiments of the methods of the disclosure, the mTOR inhibitor comprises Rapamycin (Sirolimus), Temsirolimus (Torisel), Everolimus (Afinitor) or Ridaforolimus.

In some embodiments of the methods or compositions for use of the disclosure, the at least one other chemotherapeutic agent comprises a DNA damaging agent. In some embodiments, the DNA damaging agent comprises Gemcitabine.

In some embodiments of the methods or compositions for use of the disclosure, the at least one other chemotherapeutic agent comprises a combination chemotherapy. In some embodiments, the combination chemotherapy comprises 7+3, ABVD, AC, AD, ADE, ADOC, BEACOPP, BEP, CAF, CAPIRI, CAPDX, CB, CBI, CEF, CEPP, CFAR, CHOP, CIM, CLAG, CLAG-M, CMC, CMF, COI, CVD, CVP, DHAP, DVD, ECF, ECX, EOF, EOX, EP, EPOCH, EPOCH+R, ESHAP, FAMTX, FC, FCR, FEC, FLAG-IDA, FLO, FLOX, FOLFIRI, FOLFOX, FOLFOXIRI, GEMOX-B, GVD, Hyper-CVAD, ICE, ICE-V, IFL, IROX, LV5FU2, LV5FU-P, MAID, MFL, MINE, MOPP, MP, MPV, MVAC, OFF, PAC, PAD, PCR, PCV, R-MPV, R-GemOx, R-CHOP, R-CVP, R-FCM, RICE, TAC, TC, TCH, TIP, TPC, TPF, VAD, VIP, VMP, VMPT, XELIRI or XELOX.

In some embodiments of the methods or compositions for use of the disclosure, the composition comprising pyrvinium pamoate and the at least one other chemotherapeutic agent are in the same composition. In some embodiments, the composition comprising pyrvinium pamoate and the at least one other chemotherapeutic agent are formulated in a nanoparticle. In some embodiments, the composition comprising pyrvinium pamoate and the at least one other chemotherapeutic agent are formulated in the same nanoparticle.

In some embodiments of the methods of the disclosure, the composition comprising pyrvinium pamoate and the at least one other chemotherapeutic agent are administered sequentially. In some embodiments, the composition comprising pyrvinium pamoate and the at least one other chemotherapeutic agent are administered in an alternating series. In some embodiments, the composition comprising pyrvinium pamoate and the at least one other chemotherapeutic agent are administered simultaneously. In some embodiments, the composition comprising pyrvinium pamoate and the at least one other chemotherapeutic agent are administered in temporal proximity. In some embodiments, the composition comprising pyrvinium pamoate and the at least one other chemotherapeutic agent are combined in a mixed composition.

In some embodiments of the methods or compositions for use of the disclosure, the composition comprising pyrvinium pamoate is suitable for oral administration or administered orally and the at least one other chemotherapeutic agent is suitable for parenteral administration or administered parenterally. In some embodiments, the composition comprising pyrvinium pamoate is suitable for parenteral administration or administered parenterally and the at least one other chemotherapeutic agent is suitable for oral administration or administered orally. In some embodiments, the composition comprising pyrvinium pamoate and the at least one other chemotherapeutic agent are suitable for oral administration or administered orally. In some embodiments, the composition comprising pyrvinium pamoate and the at least one other chemotherapeutic agent are suitable for parenteral administration or administered parenterally.

In some embodiments of the methods or compositions for use of the disclosure, including those embodiments wherein composition comprising pyrvinium pamoate or the at least one other chemotherapeutic agent or both are suitable for parenteral administration or administered parenterally, the parenteral administration comprises an injection or an infusion. In some embodiments, the injection comprises a subcutaneous injection, an intraperitoneal injection, an intravenous injection or an intramuscular injection. In some embodiments, the infusion comprises an intravenous infusion.

In some embodiments of the methods or compositions for use of the disclosure, the disclosure provides a method of treating a cancer in a subject in need thereof, comprising administering to the subject a therapeutically effective amount of a composition comprising 3-carboxy-1-[(3-carboxy-2-oxidonaphthalen-1-yl)methyl]naphthalen-2-olate; 2-[(E)-2-(2,5-dimethyl-1-phenylpyrrol-3-yl)ethenyl]-N,N,1-trimethylquinolin-1-ium-6-amine (pyrvinium pamoate). In some embodiments the method further comprises administering a second composition comprising at least one other chemotherapeutic agent. In some embodiments, the cancer comprises a colorectal cancer, a gastric cancer, a brain cancer, colon cancer, a breast cancer, a liver cancer, a lung cancer, a pancreatic cancer or a renal cancer. In some embodiments, the lung cancer comprises a small cell lung cancer or a non-small cell lung cancer.

In some embodiments of the methods or compositions for use of the disclosure, the disclosure provides a method of treating a cancer in a subject in need thereof, comprising administering to the subject a therapeutically effective amount of a composition comprising pyrvinium pamoate. In some embodiments the method further comprises administering a second composition comprising at least one other chemotherapeutic agent. In some embodiments, the cancer comprises a rare cancer. In some embodiments, the cancer is a blastoma, a sarcoma, a carcinoma, a neuroendocrine cancer, a gastric cancer, a mesothelioma, a chordoma, thymic cancer, a gastrointestinal stromal tumor or a pheochromocytoma. In some embodiments, the blastoma comprises a neuroblastoma.

In some embodiments of the methods or compositions for use of the disclosure, the cancer comprises a rare cancer. In some embodiments, the cancer is a blastoma, a sarcoma, a carcinoma, a neuroendocrine cancer, a gastric cancer, a mesothelioma, a chordoma or a thymic cancer. In some embodiments, the sarcoma comprises an Ewing's sarcoma, a leiomyosarcoma, an angiosarcoma or a rhabdomyosarcoma.

In some embodiments of the methods or compositions for use of the disclosure, the cancer comprises a rare cancer. In some embodiments, the cancer is a blastoma, a sarcoma, a carcinoma, a neuroendocrine cancer, a gastric cancer, a mesothelioma, a chordoma or a thymic cancer. In some embodiments, the carcinoma comprises an adrenocortical carcinoma, an adenoid cystic carcinoma (ACC), a uterine serous carcinoma, a cholangiocarcinoma, a colorectal carcinoma, an esophageal carcinoma, a hepatocellular carcinoma, a pancreatic carcinoma, a small cell lung carcinoma, an ovarian carcinoma, a gastric carcinoma or a thymic carcinoma. In some embodiments, the ovarian carcinoma comprises an endometrioid or epithelial ovarian carcinoma.

In some embodiments of the methods or compositions for use of the disclosure, the cancer comprises a rare cancer. In some embodiments, the cancer is a blastoma, a sarcoma, a carcinoma, a neuroendocrine cancer, a gastric cancer, a mesothelioma, a chordoma or a thymic cancer. In some embodiments, the thymic cancer comprises a thymoma or a thymic carcinoma.

In some embodiments of the methods or compositions for use of the disclosure, the cancer comprises a rare cancer. In some embodiments, the cancer is a blastoma, a sarcoma, a carcinoma, a neuroendocrine cancer, a gastric cancer, a mesothelioma, a chordoma or a thymic cancer. In some embodiments, the gastric cancer comprises a gastrointestinal stromal cell tumor (GIST), a lymphoma, a carcinoid tumor, a squamous cell carcinoma, small cell carcinoma or a leiomyosarcoma.

In some embodiments of the methods or compositions for use of the disclosure, the cancer comprises a rare cancer. In some embodiments, the cancer is a blastoma, a sarcoma, a carcinoma, a neuroendocrine cancer, a gastric cancer, a mesothelioma, a chordoma or a thymic cancer. In some embodiments, the neuroendocrine cancer comprises an adrenocortical carcinoma, a carcinoid tumor or a thymic cancer. In some embodiments, the carcinoid tumor comprises a small intestine tumor, an appendix tumor, a tumor of the rectum, a tumor of the bronchial system, colon tumor, a stomach tumor, a pancreatic tumor, a liver tumor, a gallbladder tumor, a bile duct tumor, an ovarian tumor, a testicular tumor, a bladder tumor, a tumor of the prostate gland, a breast tumor, a kidney tumor, a thymic tumor, an eye tumor or an ear tumor.

In some embodiments of the methods or compositions for use of the disclosure, the cancer is a stage 0 or stage 1 (early stage, pre-metastatic) cancer. In some embodiments, the cancer is a stage 2 cancer or stage 3 (spread to nearby tissues and lymph nodes) cancer. In some embodiments, the cancer is a stage 4 (advanced or metastatic) cancer.

In some embodiments of the methods or compositions for use of the disclosure, the subject is a mammal, a non-human primate or a human. In some embodiments, the subject is a human. In some embodiments, the human is a man, a woman, a child (age 1-14 years, inclusive of the final year), a baby (a 2 months to 12 months, inclusive of the final month) or a neonate (age 0 to 2 months, inclusive of the final month).

In some embodiments of the methods or compositions for use of the disclosure, the method of treatment or use of the composition further comprises at least one additional cancer treatment. In some embodiments, the at least one additional cancer treatment comprises a surgical procedure to remove at least one tumor of the cancer, at least one dose of a radiation therapy or a combination thereof. In some embodiments, the method of treatment or use of the composition comprises at least one third additional chemotherapeutic agent, a therapeutic antibody, at least one immune checkpoint modulator, a combination chemotherapy or a combination thereof. In some embodiments, the at least one third chemotherapeutic agent comprises a cell cycle checkpoint inhibitor, an immune checkpoint modulator, an antimitotic agent, a pro-apoptotic agent, a DNA damaging agent, a combination chemotherapy or an inhibitor of a DNA damage response pathway.

In some embodiments of the methods or compositions for use of the disclosure, the method of treatment or use of the composition further comprises an additional cancer treatment. In some embodiments, the additional cancer treatment comprises a surgical procedure to remove at least one tumor of the cancer, at least one dose of a radiation therapy, at least one third additional chemotherapeutic agent, a therapeutic antibody, at least one immune checkpoint modulator, a combination chemotherapy or a combination thereof. In some embodiments, the immune checkpoint modulator comprises Yervoy (Ipilimumab), Opdivo (Nivolumab), Tecentriq (Atezolizumab) or Keytruda (Pembrolizumab).

In some embodiments of the methods or compositions for use of the disclosure, the method of treatment or use of the composition further comprises an additional cancer treatment. In some embodiments, the additional cancer treatment comprises at least one third additional chemotherapeutic agent. In some embodiments, the at least one third additional chemotherapeutic agent comprises Abitrexate (Methotrexate), Afinitor (Everolimus), Alimta (PEMETREXED), Alkeran (Melphalan), Aredia (Pamidronate), Arimidex (Anastrozole), Aromasin (Exemestane), Arranon (Nelarabine), Beleodaq (Belinostat), BiCNU (Carmustine), Blenoxane (Bleomycin), Bosulif (Bosutinib), Busulfex (Busulfan), Caprelsa (Vandetanib), Carboplatin, Casodex (Bicalutamide), CeeNU (Lomustine), Cerubidine (Daunorubicin), Cisplatin, Clolar (Clofarabine), Cometriq (Cabozantinib), Cosmegen (Dactinomycin), Cotellic (Cobimetinib), CytosarU (Cytarabine), Cytoxan, Dacarbazine, Dacogen (Decitabine), DaunoXome (Daunorubicin Lipid Complex), Decadron (Dexamethasone), Docetaxel, Doxorubicin, DepoCyt (Cytarabine Lipid Complex), Dexamethasone Intensol (Dexamethasone), Dexpak Taperpak (Dexamethasone), Droxia (Hydroxyurea), Eligard (Leuprolide), Ellence (Epirubicin), Eloxatin (Oxaliplatin), Elspar (Asparaginase), Emcyt (Estramustine), Erivedge (Vismodegib), Erwinaze (Asparaginase *Erwinia chrysanthemi*), Ethyol (Amifostine), Etopophos (Etoposide), Eulexin (Flutamide), Fareston (Toremifene), Farydak (Panobinostat), Faslodex (Fulvestrant), Femara (Letrozole), Firmagon (Degarelix), Fludara (Fludarabine), 5-Fluorouracil, Folex (methotrexate), Folotyn (Pralatrexate Injection), FUDR (floxuridine), Gemzar (Gemcitabine), Gilotrif (Afatinib), Gleevec (Imatinib Mesylate), Gliadel (Carmustine), HDAC (High Dose Cytarabine), Halaven (Eribulin), Hexalen (Altretamine), Hycamtin (Topotecan), Hycamtin (Topotecan), Hydrea (Hydroxyurea), Ibrance (Palbociclib), Iclusig (Ponatinib), Idamycin PFS (Idarubicin), Ifex (Ifosfamide), Imbruvica (Ibrutinib), Inlyta (Axitinib), Intron A alfab (Interferon alfa-2a), Iressa (Gefitinib), Irinotecan, Istodax (Romidepsin), Ixempra (Ixabepilone), Jakafi (Ruxolitinib), Jevtana (Cabazitaxel Injection), Kyprolis (Carfilzomib), Lenvima (Lenvatinib mesylate), Somatuline Depot (Lanreotide acetate), Leukeran (Chlorambucil), Leukine (Sargramostim), Leustatin (Cladribine), Lonsurf (Trifluridine and Tipiracil), Lupron (Leuprolide), Lupron Depot (Leuprolide), Lupron Depot-PED (Leuprolide), Lynparza (Olaparib), Lysodren (Mitotane), Matulane (Procarbazine), Xofigo (Radium 223 dichloride), Megace (Megestrol), Mekinist (Trametinib), Mesnex (Mesna), Mesnex (Mesna Injection), Metastron (Strontium-89 Chloride), Mexate (Methotrexate) Mustargen (Mechlorethamine), Mutamycin (Mitomycin), Myleran (Busulfan), Navelbine (Vinorelbine), Neosar (Cyclophosphamide), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Odomzo (Sonidegib), Oncaspar (Pegaspargase), Ontak (Denileukin Diftitox), Paclitaxel, Panretin (Alitretinoin), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), RoferonA alfa (Interferon alfa-2a), Sandostatin (Octreotide), Sandostatin LARDepot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b), Synribo (Omacetaxin), Tabloid (Thioguanine), Taflinar (Dabrafenib), Tarceva (Erlotinib), Targretin (Bexarotene), Tasigna (Nilotinib), Temodar (Temozolomide), Tepadina (Thiotepa), Thalomid (Thalidomide), TheraCys BCG (BCG), Thioplex (Thiotepa), TICE BCG (BCG), Toposar (Etoposide), Torisel (Temsirolimus), Yondelis (Trabectedin), Treanda (Bendamustine hydrochloride), Trelstar (Triptorelin), Trexall (Methotrexate), Trisenox (Arsenic trioxide), Tykerb (lapatinib), Valstar (Valrubicin Intravesical), Vantas (Histrelin Implant), Velcade (Bortezomib), Vepesid (Etoposide), Vesanoid (Tretinoin), Vincristine, Vidaza (Azacitidine), Vinblastine, Votrient (Pazopanib), Vumon (Teniposide), Wellcovorin IV (Leucovorin), Xalkori (Crizotinib), Xeloda (Capecitabine), Xtandi (Enzalutamide), Zaltrap (Ziv-aflibercept), Zanosar (Streptozocin), Zelboraf (Vemurafenib), Zoladex (Goserelin), Zolinza (Vorinostat), Zometa (Zoledronic acid), Zortress (Everolimus), Zydelig (Idelalisib), Zykadia (Ceritinib), Zytiga (Abiraterone acetate), Vindesine (Eldesine), Raltitrexed (Tomudex), Lometrexol, Satraplatin, Larotaxel, Alectinib (Alecensa), Ixazomib (Ninlaro), Nilotinib (Tasigna), Osimertinib (Tagrisso), Venetoclax (Venclexta), Ribociclib (Kisqali), Enasidenib (Idhifa), Rucaparib (Rubraca), Niraparib (Zejula), Copanlisib (Aliqopa), Neratinib (Nerlynx), Brigatinib (Alunbrig), Midostaurin (Rydapt), Abemaciclib (Verzenio), Rapamycin (Sirolimus), Temsirolimus (Torisel), Ridaforolimus or a combination thereof.

In some embodiments of the methods or compositions for use of the disclosure, the method of treatment or use of the composition further comprises an additional cancer treatment. In some embodiments, the additional cancer treatment comprises a therapeutic antibody. In some embodiments, the therapeutic antibody comprises therapeutic antibody comprises Adcetris (Brentuximab Vedotin), Arzerra (Ofatumumab), Avastin (Bevacizumab), Bexxar (Tositumomab), Bavencio (Avelumab), Blincyto (Blinatumomab), Campath (Alemtuzumab), Cyramza (Ramucirumab), Darzalex (Daratumumab), Empliciti (Elotuzumab), Erbitux (Cetuximab), Gazyva (Obinutuzumab), Imfinzi (Durvalumab), Herceptin (Trastuzumab), Gazyvaro (Obinutuzumab), Kadcyla (Ado-trastuzumab Emtansine), Keytruda (Pembrolizumab), Lartruvo (Olaratumab), Mylotarg (Gemtuzumab Ozogamicin), Ocrevus (Ocrelizumab), Opdivo (Nivolumab), Perj eta (Pertuzumab), Portrazza (Necitumumab), Proxinium (Catumaxomab), Removab (Catumaxomab), Rituxan (Rituximab), Sylvant (Siltuximab), Tecentriq (Atezolizumab), Unituxin (Dinutuximab), Vectibix (Panitumumab), Yervoy (Ipilimumab), Xgeva (Denosumab), Zevalin (Ibritumomab Tiuxetan), Mogamulizumab (Poteligeo) or a combination thereof.

In some embodiments of the methods or compositions for use of the disclosure, the method of treatment or use of the composition further comprises an additional cancer treatment. In some embodiments, the additional cancer treatment comprises a combination chemotherapy. In some embodiments of the methods or compositions for use of the disclosure, the combination chemotherapy comprises 7+3, ABVD, AC, AD, ADE, ADOC, BEACOPP, BEP, CAF, CAPIRI, CAPDX, CB, CBI, CEF, CEPP, CFAR, CHOP, CIM, CLAG, CLAG-M, CMC, CMF, COI, CVD, CVP, DHAP, DVD, ECF, ECX, EOF, EOX, EP, EPOCH, EPOCH+R, ESHAP, FAMTX, FC, FCR, FEC, FLAG-IDA, FLO, FLOX, FOLFIRI, FOLFOX, FOLFOXIRI, GEMOX-B, GVD, Hyper-CVAD, ICE, ICE-V, IFL, IROX, LV5FU2, LVSFU-P, MAID, MFL, MINE, MOPP, MP, MPV, MVAC, OFF, PAC, PAD, PCR, PCV, R-MPV, R-GemOx, R-CHOP, R-CVP, R-FCM, RICE, TAC, TC, TCH, TIP, TPC, TPF, VAD, VIP, VMP, VMPT, XELIRI or XELOX.

In some embodiments of the methods or compositions for use of the disclosure, the method of treatment or use of the composition further comprises at least one additional cancer treatment. In some embodiments, the at least one additional cancer treatment comprises a surgical procedure to remove at least one tumor of the cancer or at least one dose of a radiation therapy, or a combination thereof. In some embodiments of the methods of the disclosure, the composition comprising pyrvinium pamoate is suitable for or administered at the same time as the at least one dose of radiation therapy. In some embodiments, the composition comprising pyrvinium pamoate is suitable for or administered prior to the at least one dose of radiation therapy. In some embodiments, the composition comprising pyrvinium pamoate is suitable for or administered after the at least one dose of radiation therapy. In some embodiments, the composition comprising pyrvinium pamoate is suitable for or administered in temporal proximity to the at least one dose of radiation therapy.

In some embodiments of the methods or compositions for use of the disclosure, the method of treatment or use of the composition further comprises at least one additional cancer treatment. In some embodiments, the additional cancer treatment comprises a surgical procedure to remove at least one tumor of the cancer, at least one dose of a radiation therapy or a combination thereof. In some embodiments, the surgical procedure to remove at least one tumor of the cancer removes the entire tumor. In some embodiments, the surgical procedure to remove at least one tumor of the cancer removes a part of the tumor.

In some embodiments of the methods of the disclosure, the method or use of the composition further comprises adoptive cell therapy, a therapy comprising a viral vector or a combination thereof. In some embodiments, the adoptive cell therapy comprises a chimeric antigen receptor T cell (CAR-T) therapy.

In some embodiments of the methods or compositions for use of the disclosure, the method of treatment or use of the composition alleviates a sign or a symptom of the cancer. In some embodiments, the alleviation of the sign or the symptom of the cancer comprises a reduction in size of at least one tumor, a reduction in the volume of at least one tumor, a decrease in the number of tumors, a decrease in the number of metastatic lesions of the cancer, a reduction of the rate of growth of the cancer or a remission of the cancer.

The disclosure provides a composition comprising a synergistic combination of pyrvinium pamoate and at least one additional cancer therapeutic agent.

In some embodiments of the compositions of the disclosure, the synergy is measured using the Chou-Talalay method in at least one cancer cell line. In some embodiments, the synergy comprises a CI of less than 0.9 when measured at at least three concentrations of the additional cancer therapeutic agent and the composition comprising pyrvinium pamoate in at least one cancer cell line. In some embodiments, the composition comprising pyrvinium pamoate comprises a salt or a salt hydrate. In some embodiments, the salt comprises an anhydrous dipyrvinium pamoate salt.

In some embodiments of the compositions of the disclosure, the at least one additional cancer therapeutic agent comprises Cisplatin, Doxorubicin, Etoposide, Vincristine, Paclitaxel, 5-FU, Irinotecan, Carboplatin, Cyclophosphamide, Gemcitabine, Abemaciclib, Oxaliplatin, Erlotinib, Imatinib or Sorafenib.

In some embodiments of the compositions of the disclosure, the pyrvinium pamoate is formulated in a nanoparticle. In some embodiments, the composition comprising pyrvinium pamoate and the at least one additional cancer therapeutic agent are formulated in a nanoparticle. In some embodiments, composition comprising pyrvinium pamoate and the at least one additional cancer therapeutic agent are formulated in the same nanoparticle. In some embodiments, the nanoparticle comprises a liposome, a micelle, a polymer-based nanoparticle, a lipid-polymer based nanoparticle, a metal based nanoparticle, a nanocrystal, a carbon nanotube based nanoparticle or a polymeric micelle. In some embodiments, the polymer-based nanoparticle comprises a multiblock copolymer, a diblock copolymer, a polymeric micelle or a hyperbranched macromolecule. In some embodiments, the polymer-based nanoparticle comprises a multiblock copolymer a diblock copolymer. In some embodiments, the polymer-based nanoparticle comprises a poly(lactic-co-glycolic acid) PLGA polymer. In some embodiments of the compositions of the disclosure, the polymer-based nanoparticle is pH responsive. In some embodiments of the compositions of the disclosure, the polymer-based nanoparticle further comprises a buffering component.

In some embodiments of the compositions of the disclosure, the nanoparticle further comprises a targeting agent. In some embodiments, the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment. In some embodiments, the targeting agent comprises hyaluronic acid (HA). In some embodiments, the targeting agent binds to the surface of a cell of the cancer of the subject. In some embodiments, the targeting agent comprises HA and the HA binds to CD44 on the surface of a cell of the cancer.

The disclosure provides pharmaceutical compositions comprising the pyrvinium pamoate compositions of the disclosure and a pharmaceutically acceptable carrier, diluent or excipient.

The disclosure provides a combinational therapy for treating cancer, comprising administering a therapeutically effective amount of a composition comprising pyrvinium pamoate of the disclosure to a subject in need thereof.

The disclosure provides a combinational therapy for treating cancer, comprising administering a synergistically effective amount of a composition comprising pyrvinium pamoate of the disclosure to a subject in need thereof.

The disclosure provides a composition for use in a combinational therapy to treat cancer, comprising a therapeutically effective amount of a composition comprising pyrvinium pamoate of the disclosure. In some embodiments, the combinational therapy comprises administering one or more additional cancer therapies to the subject.

The disclosure provides kits comprising a composition comprising pyrvinium pamoate of the disclosure and instructions for use in the treatment of cancer.

The disclosure provides kits comprising a therapeutically effective amount of a composition comprising pyrvinium pamoate and instructions for use in the treatment of cancer.

In some embodiments of the kits of the disclosure, the kit further comprises at least one additional cancer therapeutic agent. In some embodiments, the therapeutically effective amount of the composition comprising pyrvinium pamoate comprises a synergistically effective amount of the composition comprising pyrvinium pamoate. In some embodiments, the composition comprising pyrvinium pamoate and the at least one additional cancer therapeutic agent exhibit synergy. In some embodiments, the at least one additional cancer therapeutic agent comprises a second chemotherapeutic agent, a combination chemotherapy, a therapeutic antibody, a chimeric antigen receptor T cell (CAR-T) therapy or a combination thereof. In some embodiments, the at least one additional cancer therapeutic agent comprises Paclitaxel, Docetaxel, Vincristine, Vinorelbine, Cisplatin, Carboplatin, Oxaliplatin, Irinotecan, Etoposide, 5-FU, Doxorubicin, Temozolomide, Dacarbazine, Cyclophosphamide, Ifosfamide, Abemaciclib, Gemcitabine, Erlotinib, Imatinib or Sorafenib.

In some embodiments of the kits of the disclosure, the pyrvinium pamoate is formulated in a nanoparticle. In some embodiments, the pyrvinium pamoate and the at least one additional cancer therapeutic agent are formulated in a nanoparticle. In some embodiments, the nanoparticle comprises a PLGA polymer and an HA targeting agent.

BRIEF DESCRIPTION OF THE DRAWINGS

FIG. 2A shows the TC-71 cell line. FIG. 2B shows the TC-32 cell line. FIG. 2C shows the CHLA-9 cell line. Cells were treated with nine serial dilutions of pyrvinium pamoate (0-2 µM).

FIG. 3A show the IMR-32 cell line. FIG. 3B shows the CHP-212 cell line. Cells were treated with nine serial dilutions of pyrvinium pamoate (0-2 µM).

FIG. 5A shows the SW-13 cell line. FIG. 5B shows the NCI-H295R cell line. Cells were treated with nine serial dilutions of pyrvinium pamoate (0-2 µM).

FIG. 6A shows the Rh30 cell line. FIG. 6B shows the Rh41 cell line. Cells were treated with nine serial dilutions of pyrvinium pamoate (0-2 µM).

FIG. 7A shows the SNU-16 cell line. FIG. 7B shows the KATO-III cell line. FIG. 7C shows the NCI-N87 cell line. Cells were treated with nine serial dilutions of pyrvinium pamoate (0-2 µM).

FIG. 8A shows the TOV-112D cell line. FIG. 8B shows the COV362 cell line. Cells were treated with nine serial dilutions of pyrvinium pamoate (0-2 µM).

FIG. 9A shows the U-CH2 cell line. FIG. 9B shows the MUG-Chor1 cell line. Cells were treated with nine serial dilutions of pyrvinium pamoate (0-2 µM).

FIG. 10A shows CHP212 cells. FIG. 10B shows COV362 cells.

FIG. 12 is a plot showing exposure level of pyrvinium pamoate (PP) following a single injection of 1 mg/kg of pyrvinium pamoate encapsulated nanoparticle.

FIG. 15 is a table showing a combination analysis of pyrvinium pamoate and an exemplary chemotherapeutic agent in a Latin square using the Chou-Talalay method in a representative cell line. The Combination Index (CI) at each pair of concentrations is indicated. Shaded boxes indicate concentrations of pyrvinium pamoate and the exemplary chemotherapeutic agent that are synergistic.

FIG. 16 is a table showing a combination analysis of pyrvinium pamoate and Paclitaxel in a Latin square using the Chou-Talalay method. Pyrvinium pamoate and Paclitaxel combinations were tested in the gastric cancer cell line SNU16. The Combination Index (CI) at each pair of concentrations is indicated. Shaded boxes indicate concentrations of pyrvinium pamoate and Paclitaxel that are synergistic.

FIG. 17A shows rare and non-rare cancer diagnoses in the U.S. in 2017. FIG. 17B shows the proportion of rare and non-rare cancers in the 396 known distinct cancers.

FIG. 18A is a graph showing rare vs non-rare percent of 2017 diagnoses. FIG. 18B is a pie chart showing rare vs non-rare forms of 7 "common" cancers. Major types of cancer, including breast, lung, and leukemia, are composed of many forms of cancer, both rare and common, each with distinct molecular drivers that require different treatments. As more molecular data become available, additional rare forms of cancer will likely be identified.

DETAILED DESCRIPTION

Figure 1:
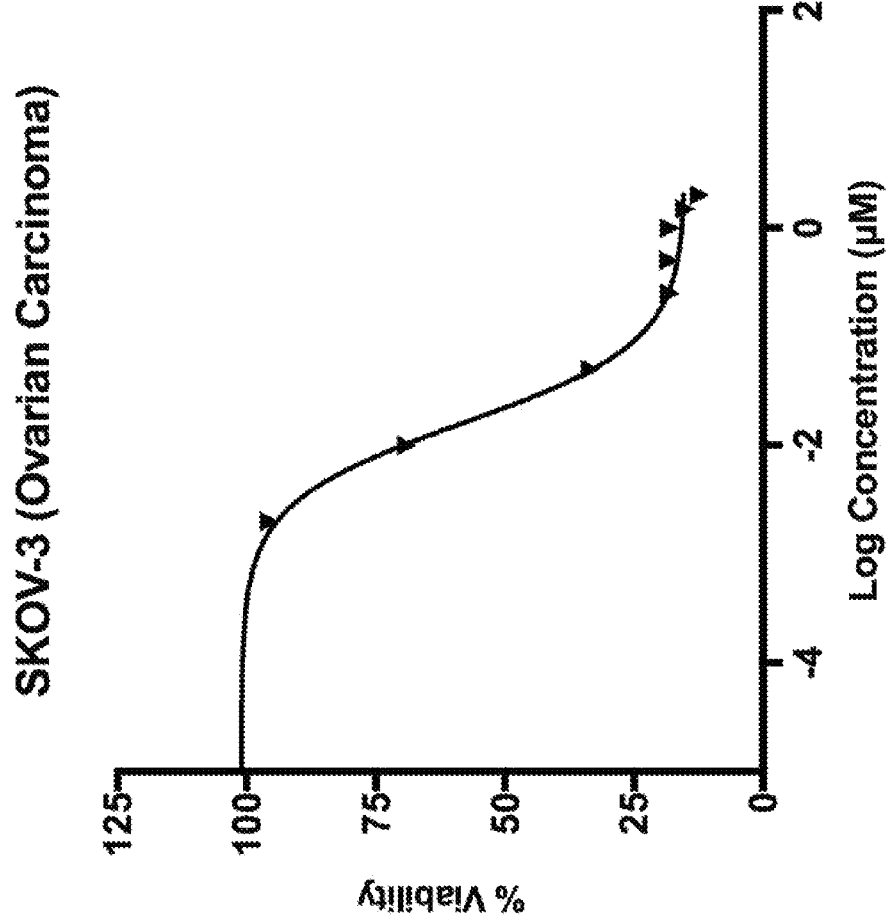
FIG. 1 is a plot showing the effect of pyrvinium pamoate on the ovarian carcinoma cell line SKOV-3 cell viability. Cells were treated with nine serial dilutions of pyrvinium pamoate (0 to 2 µM) for 72 hours.

The present invention is related to the finding that the anti-helminthic drug pyrvinium pamoate (PP) can affect several relevant molecular pathways in tumor growth and metastasis. Pyrvinium pamoate is an antihelmintic drug that was first offered for sale in 1977 or earlier. Unlike some other anthelmintics, pyrvinium pamoate works exclusively against pinworms, where it is thought to impede exogenous carbohydrate metabolism. Pyrvinium pamoate has been well studied in humans, and has low toxicity.

Pyrvinium pamoate's potential anti-cancer activities are thought to have multiple potential mechanisms of action, which makes pyrvinium pamoate an attractive candidate for treating any number of cancers. Without wishing to be bound by any particular theory or limited to any one mode of action, a few of the pathways thought to be affected by pyrvinium pamoate are laid out below.

For example, pyrvinium pamoate is thought to inhibit the Wingless/Integrated (Wnt) signaling pathway. Wnt signal transduction occurs through several pathways, and the best characterized are the canonical Wnt pathway, the non-canonical pathway, and Wnt signaling involvement in planar cell polarity. All three pathways are activated by binding of the Wnt ligand to the Frizzled transmembrane receptor, which acts through Dishevelled to transduce the signal inside the cell. In the canonical pathway, binding of Wnt to its receptor complex (Frizzled and the LDL receptor related protein 5 and LDL receptor related protein 6) leads to the disruption of the adenomatous polyposis coli (APC)/Axin/Glycogen synthase kinase 3 (GSK3) complex. The APC/Axin/GSK3 complex is required for the targeted destruction of β-catenin in the cytoplasm, and upon its disruption, β-catenin translocates to the nucleus where it can regulate gene expression. The activity of Dishevelled can be regulated through phosphorylation by a number of kinases, including Casein Kinase 1, Casein Kinase 2, Metastasis Associated Kinase, Protein Kinase C and Parl. The non-canonical Wnt pathways proceed downstream of Dishevelled largely independent of beta-catenin, and are thought to signal through additional cellular pathways such as through Rho-associated protein kinase (ROCK), the c-JUN N-terminal kinase (JNK), or through Protein Kinase C (to name a few). There are thus a number of mechanisms by which pyrvinium pamoate could affect Wnt signaling. Without wishing to be bound by any particular theory, for example, pyrvinium pamoate could bind to all casein kinase 1 (CK1) family members in and selectively potentiate casein kinase 1a (CK1a) kinase activity to inhibit Wnt signaling activity.

Pyrvinium pamoate's potential effect on Wnt signaling makes it an attractive therapeutic agent for those cancers, for example, in which Wnt signaling has been implicated. These cancers include adrenocortical and hepatocellular cancers, hepatoblastoma, malignant melanoma, glioblastoma, ovarian cancer, Wilm's tumor, Barrett's esophageal, glioma, bladder, breast, gastric, head & neck, colon, myeloma, lung cell, and mesothelioma, uterine, and cervical cancers. Combined, ovarian, uterine, and cervical cancers are responsible for 14 percent of female cancer deaths, and have a mortality rate of 45 percent.

In addition, pyrvinium pamoate is also thought to inhibit mitochondrial respiration, and as such may affect apoptosis. A hallmark of malignant cancer cells is the ability to evade apoptosis. Pyrvinium pamoate's ability to interfere with the mitochondria makes it especially attractive as a potential radio- or chemo-enhancer, or as a maintenance therapy, where its use may prevent dormant cancer cells from becoming active. Further, pyrvinium pamoate is also thought to inhibit STAT3 signaling. Janus Kinase/Signal Transduced and Activator of Transcription (Jak/Stat) signaling is important in cytokine mediated immune responses, and has also been shown to be involved in cellular processes such as proliferation, apoptosis and migration, which are important pathways in cancer progression. Jak/Stat dysregulation has frequently been found in diverse types of cancer. Thus, STAT3 is a potential therapeutic target in developing cancer treatments.

Pyrvinium pamoate is also thought to suppress the transcriptional activation of the glucose regulated protein 78 (GRP78) and glucose regulated protein 94 (GRP94). GRP78 and GRP94 are heat shock family member molecular chaperones, and as such are involved in the regulation of protein machinery and may play a role in the invasion of various cancers. Pyrvinium pamoate may also induce autophagy via regulation of the mTOR pathway by AMPK. Autophagy is a process that leads to cellular proteins and organelles being engulfed by autophagosomes and recycled to sustain cellular metabolism. In cancers, autophagy is activated as a response to the stress and increased demands of rapid cellular growth of the cancer. Autophagy thus represents an additional therapeutic target in the treatment of cancer. Given its potential roles in a variety of molecular and cellular processes critical to cancer progression, pyrvinium pamoate represents a novel therapeutic agent for the treatment of cancers, and one whose safety in humans as an antihelmintic is well characterized.

Cancer is a proliferative disease of a subject's own cells. In cancer, malignant cells in a subject overcome normal constraints on cellular proliferation and multiply unchecked. Because cancer is a disease of a subject's own cells the therapeutic window for treating cancer, i.e. killing only cancer cells and not healthy cells, is correspondingly narrow. Even a well-characterized and common cancer such as breast cancer, for which a variety of treatments is available, has a five-year relapse rate of around 7 to 13 percent. There thus exists an unmet need in the field for additional cancer therapies. This need is particularly acute with respect to rare cancers. Rare cancers are defined by the National Cancer Institute as cancers that occur in less than 15 cases per 100,000 people per year. The American Cancer Society's (ACS) metric for rare cancers is less than 6 per 100,000 incidence. Using this metric, of 396 known distinct cancers, 374 are rare forms. Cumulatively, estimates for the number of rare cancers diagnosed in adults range between 22% and 42% of all diagnosed cancers. In 2017, by the conservative ACS metric, there were over 500,000 rare cancer diagnoses in the United States alone. Extrapolating from U.S. metrics, the U.S., E.U. and China alone likely had over 3.2 million rare cancer diagnoses in 2017. However, because each cancer is unique, recently developed targeted cancer therapies, such as immune and antibody based therapies or chemotherapies that target particular pathways specific to certain cancers may not work or have not been investigated in rare cancers. Depending upon the definition used, as many as half of all cancers diagnosed are considered rare cancers. The disclosure provides methods for using an additional therapeutic agent, pyrvinium pamoate, for use in the cancer treatment arsenal.

Pyrvinium Pamoate

The disclosure provides the use of pyrvinium pamoate, or a pharmaceutically acceptable salt, polymorph or solvate thereof in the treatment of cancer in a subject, or for the preparation of a therapeutically effective composition useful for the treatment of such a cancer. In some embodiments, pyrvinium pamoate may be used as a monotherapy. Alternatively, in some embodiments, pyrvinium pamoate may be combined with additional cancer therapies. The disclosure provides a method of treating a cancer in a subject in need thereof, comprising administering to the subject a therapeutically effective amount of a composition comprising 3-carboxy-1-[(3-carboxy-2-oxidonaphthalen-1-yl)methyl]naphthalen-2-olate;2-[(E)-2-(2,5-dimethyl-1-phenylpyrrol-3-yl)ethenyl]-N,N,1-trimethylquinolin-1-ium-6-amine (pyrvinium pamoate, or PP). Pyrvinium is represented by the formula:

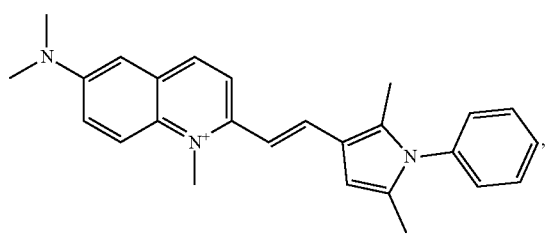 [SMILES: Cc1cc(/C=C/c2ccc3cc(N(C)C)ccc3[n+]2C)c(C)n1-c1ccccc1]

while pyrvinium pamoate comprises the formula of:

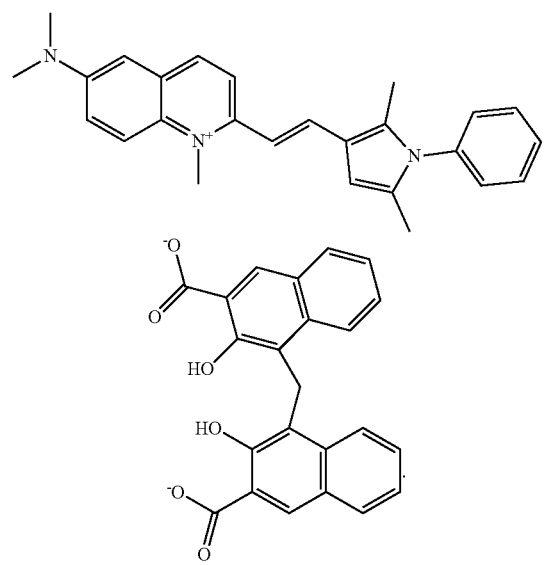

In some embodiments of the pyrvinium of the disclosure, the pyrvinium comprises a salt. In some embodiments, the pyrvinium salt comprises a pyrvinium pamoate salt. Additional forms of pyrvinium fall within the scope of the invention. In some embodiments, the pyrvinium salt comprises a halide, a tosylate or triflate. Additional, but non-limiting examples of pyrvinium salts comprise pyrvinium chloride and pyrvinium iodide.

Additionally, in some embodiments of the pyrvinium of the present disclosure, a salt of pyrvinium can exist in either hydrated or unhydrated (the anhydrous) form or as solvates with other solvent molecules. In some embodiments, the pyrvinium of the disclosure comprises a solvate. In some embodiments, the pyrvinium pamoate comprises a pyrvinium pamoate solvate. In some embodiments, the solvate comprises one or more water molecules (a hydrate). Non-limiting examples of hydrates include monohydrates, dihydrates, and so forth. Non-limiting examples of solvates include ethanol solvates, acetone solvates, and forth.

In some embodiments of the pyrvinium pamoate of the disclosure, the pyrvinium pamoate is anhydrous. In some embodiments, the pyrvinium pamoate comprises an anhydrous dipyrvinium pamoate.

In some embodiments, the pyrvinium pamoate of the disclosure comprises a crystal. All crystal polymorph forms of pyrvinium are considered to be within the scope of the invention.

Administering a composition comprising pyrvinium pamoate, or a pharmaceutically acceptable salt, polymorph or solvate thereof, to a cell or a subject in need thereof results in modulation (i.e., stimulation or inhibition) of an activity of an intracellular target (e.g., substrate). In some embodiments, several intracellular targets can be modulated with the composition comprising pyrvinium pamoate.

Without wishing to be bound by any particular theory or limit the mechanisms or biological pathways through which pyrvinium pamoate may act, set forth are some ways in which pyrvinium pamaote can affect the cancer cells of a subject.

Contacting a cell with a composition comprising pyrvinium pamoate, or a pharmaceutically acceptable salt, polymorph or solvate thereof or nanoparticle formulation thereof, can induce or activate cell death preferentially in cancer cells, or slow the growth or progression of the cancer cells. Administering to a subject in need thereof a composition comprising pyrvinium pamoate, or a pharmaceutically acceptable salt, polymorph or solvate thereof or a nanoparticle formulation thereof, can induce or activate cell death, or slow the growth of in cancer cells, or otherwise hinder the progression of the cancer. Preferably, administering to a subject in need thereof a composition comprising pyrvinium pamoate, or a pharmaceutically acceptable salt, polymorph or solvate thereof or a nanoparticle formulation thereof, induces cell death or halts cell division preferentially in one or more cells affected by a cell proliferative disorder. Preferably, the overall toxicity of the therapeutic amount of the composition comprising pyrvinium pamoate is well tolerated.

In some embodiments, the therapeutically effective amount of the composition that comprises pyrvinium pamoate interferes with the carbohydrate metabolism of the cancer cells of a subject. Exemplary effects of inhibiting carbohydrate metabolism comprise causing glycogen depletion, inhibiting glucose uptake, and/or disrupting enzymes involved in carbohydrate metabolism. In some embodiments, interfering with carbohydrate metabolism causes the death of the cell.

In some embodiments, pyrvinium pamoate inhibits Wnt signaling in the cancer cells of the subject. Inhibiting Wnt signaling can change cancer cell metabolism, and inhibit the growth of Wnt-activated cancer cells, preventing the cancer from progressing. In some embodiments, pyrvinium pamoate may inhibit mitochondrial respiration, promoting apoptosis of cancer cells. In some embodiments, pyrvinium pamoate can inhibit STAT3 signaling, inhibiting the proliferation or progression of the cancer. In some embodiments, pyrvinium pamoate can affect the function of molecular chaperones such as GRP78 and GRP94, affecting the protein metabolism and protein recycling of the cancer cell. In some embodiments, pyrvinium pamoate may induce autophagy via the mTOR pathway, leading to a decrease in cancer cell survival.

As used herein, "apoptosis" refers to the process of programmed cell death that occurs to selectively kill a cell in a multicellular organism. During apoptosis, the mitochondria release of cytochrome c into the cytosol, which triggers a cascade of caspase activation, leading to cell death. During apoptosis, phosphorylation of Bcl-2 (BCL2, apoptosis regulator), prevents Bcl-2 from interacting with the proapoptotic BCL2 associated X, apoptosis regulator (Bax) protein and promoting apoptosis. Bcl-2 is an integral outer mitochondrial membrane protein that blocks apoptotic death in some cells. Bax is a member of the Bcl-2 protein family and a proapoptotic protein. Upon triggering of apoptosis, Bax and the related protein BCL2 antagonist/killer 1 (Bak) form oligomers in the outer mitochondrial membrane, allowing contents from the mitochondrial intermembrane space to translocate to the cytosol, leading to apoptosis.

As used herein, "molecular chaperone" refers to a protein that assists in the folding or unfolding of a protein, or in the assembly or disassembly of a macromolecular structure. Exemplary molecular chaperones comprise heat shock proteins.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

"Halide" as used herein refers to a binary compound comprising a halogen with another element or group that is less electronegative than the halogen. Exemplary halides comprise fluoride, chloride, bromide, iodide and astatide. "Tosylate" as used herein refers to a salt or an ester containing a tosyl group, or toluenesulfonic acid. "Triflate" as used herein refers to a function group containing trifluoromethanesulfonate.

It should be understood that all references to pharmaceutically acceptable salts include solvent addition forms (solvates) or crystal forms (polymorphs) as defined herein, of the same salt.

In some embodiments of the methods of the disclosure, the composition comprising pyrvinium pamoate further comprises a nanoparticle. In some embodiments, the nanoparticle comprises a liposome, a micelle, a polymer-based nanoparticle, a lipid-polymer based nanoparticle, a metal based nanoparticle, a carbon nanotube based nanoparticle, a nanocrystal or a polymeric micelle. In some embodiments, the polymer-based nanoparticle comprises a multiblock copolymer, a diblock copolymer, a polymeric micelle or a hyperbranched macromolecule. In some embodiments, the polymer-based nanoparticle comprises a multiblock copolymer a diblock copolymer. In some embodiments, the polymer-based nanoparticle is pH responsive. In some embodiments, the polymer-based nanoparticle further comprises a buffering component.

In some embodiments, the composition comprising pyrvinium pamoate further comprises a nanoparticle. In some embodiments, the nanoparticle comprises a liposome. Liposomes are spherical vesicles having at least one lipid bilayer, and in some embodiments, an aqueous core. In some embodiments, the lipid bilayer of the liposome may comprise phospholipids. An exemplary but non-limiting example of a phospholipid is phosphatidylcholine, but the lipid bilayer may comprise additional lipids, such as phosphatydilethanoamine. Liposomes may be multilamellar, i.e. consisting of several lamellar phase lipid bilayers, or unilamellar liposomes with a single lipid bilayer. Liposomes can be made in a particular size range that makes them viable targets for phagocytosis. Liposomes can range in size from 20 nm to 100 nm, 100 nm to 400 nm, 1 μM and larger, or 200 nm to 3 μM. Examples of lipidoids and lipid-based formulations are provided in U.S. Published Application 20090023673. In other embodiments, the one or more lipids are one or more cationic lipids. One skilled in the art will recognize which liposomes are appropriate for pyrvinium pamoate encapsulation.

In some embodiments, the nanoparticle comprises a micelle. A micelle is an aggregate of surfactant molecules. An exemplary micelle comprises an aggregate of amphiphilic macromolecules, polymers or copolymers in aqueous solution, wherein the hydrophilic head portions contact the surrounding solvent, while the hydrophobic tail regions are sequestered in the center of the micelle.

In some embodiments, the nanoparticle comprises a nanocrystal. Exemplary nanocrystals are crystalline particles with at least one dimension of less than 1000 nanometers, preferably of less than 100 nanometers.

In some embodiments, the nanoparticle comprises a polymer based nanoparticle. In some embodiments, the polymer comprises a multiblock copolymer, a diblock copolymer, a polymeric micelle or a hyperbranched macromolecule. In some embodiments, the particle comprises one or more cationic polymers. In some embodiments, the cationic polymer is chitosan, protamine, polylysine, polyhistidine, polyarginine or poly(ethylene)imine. In other embodiments, the one or more polymers contain the buffering component, degradable component, hydrophilic component, cleavable bond component or some combination thereof.

In some embodiments, the nanoparticles or some portion thereof are degradable. In other embodiments, the lipids and/or polymers of the nanoparticles are degradable.

In some embodiments, any of these nanoparticles can comprise a buffering component. In other embodiments, any of the nanoparticles can comprise a buffering component and a degradable component. In still other embodiments, any of the nanoparticles can comprise a buffering component and a hydrophilic component. In yet other embodiments, any of the nanoparticles can comprise a buffering component and a cleavable bond component. In yet other embodiments, any of the nanoparticles can comprise a buffering component, a degradable component and a hydrophilic component. In still other embodiments, any of the nanoparticles can comprise a buffering component, a degradable component and a cleavable bond component. In further embodiments, any of the nanoparticles can comprise a buffering component, a hydrophilic component and a cleavable bond component. In yet another embodiment, any of the nanoparticles can comprise a buffering component, a degradable component, a hydrophilic component and a cleavable bond component. In some embodiments, the particle is composed of one or more polymers that contain any of the aforementioned combinations of components.

In some embodiments, the nanoparticle further comprises pyrvinium pamoate. In some embodiments, the pyrvinium pamoate is on the surface and/or within the nanoparticle. In other embodiments, the pyrvinium pamoate is conjugated to, complexed to or encapsulated within the nanoparticle. In further embodiments, the pyrvinium pamoate is conjugated to, complexed to or encapsulated by the one or more lipids or polymers of the nanoparticle. In some embodiments, the conjugation is covalent. In some embodiments, the pyrvinium pamoate is intercalated within the lipids or polymers of the nanoparticle.

In some embodiments, the nanoparticle further comprises a targeting agent. In some embodiments, the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment. In some embodiments, the targeting agent binds to the surface of a cell of the cancer of the subject. In some embodiments, the targeting agent is on the surface and/or within the nanoparticle.

In some embodiments, the targeting agent comprises hyaluronic acid (HA). HA binds to CD44, a transmembrane peptidoglycan expressed on the surface of many types of cancer cells. CD44 integrates cellular environmental cues with growth factors and cytokine signals, and plays a role in the progression of many cancers. Targeting of CD44+ cells by HA nanoparticles thus provides superior delivery and specificity of the compositions of the disclosure to cancer cells.

In some embodiments, the nanoparticle further comprises a blending polymer. In some embodiments, the blending polymer is a copolymer comprising a degradable component and hydrophilic component. In some embodiments, the degradable component of the blending polymer is a polyester, poly(ortho ester), poly(ethylene imine), poly(caprolactone), polyanhydride, poly(acrylic acid), polyglycolide or poly(urethane). In some embodiments, the degradable component of the blending polymer is poly(lactic acid) (PLA) or poly(lactic-co-glycolic acid) (PLGA). In some embodiments, the hydrophilic component of the blending polymer is a polyalkylene glycol or a polyalkylene oxide. In some embodiments, the polyalkylene glycol is polyethylene glycol (PEG). In other embodiments, the polyalkylene oxide is polyethylene oxide (PEO).

In some embodiments, the one or more polymers comprise a polyester, poly(ortho ester), poly(ethylene imine), poly(caprolactone), polyanhydride, poly(acrylic acid), polyglycolide or poly(urethane). In still other embodiments, the one or more polymers comprise poly(lactic acid) (PLA) or poly(lactic-co-glycolic acid) (PLGA). In some embodiments, the one or more polymers comprise poly(lactic-co-glycolic acid) (PLGA). In some embodiments, the one or more polymers comprise polyalkylene glycol or a polyalkylene oxide. In some embodiments, the polyalkylene glycol is polyethylene glycol (PEG) or the polyalkylene oxide is polyethylene oxide (PEO).

In some embodiments, the nanoparticle has an average characteristic dimension of less than about 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm or 20 nm. In other embodiments, the nanoparticle has an average characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm. In further embodiments, the nanoparticle has an average characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

Sterile injectable solutions comprising a nanoparticle of the disclosure can be prepared by incorporating the pyrvinium pamoate in the nanoparticles in the required amount in an appropriate solvent with one or a combination of ingredients enumerated herein, as required, followed by filtered sterilization. Alternatively, or in addition, sterilization can be achieved through other means such as radiation or gas. Generally, dispersions are prepared by incorporating the nanoparticles into a sterile vehicle that contains a basic dispersion medium and the required other ingredients from those enumerated above. In the case of sterile powders for the preparation of sterile injectable solutions, methods of preparation are vacuum drying and freeze-drying that yields a powder of pyrvinium pamoate nanoparticles plus any additional desired ingredient from a previously sterile-filtered solution thereof.

Oral compositions comprising the pyrvinium pamoate nanoparticles of the disclosure generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the nanoparticles in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as sodium starch glycolate, starch or lactose, a diluent such as microcrystalline cellulose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the pyrvinium pamoate nanoparticle is delivered in the form of an aerosol spray from pressured container or dispenser, which contains a suitable propellant, e.g., a gas such as carbon dioxide, or a nebulizer.

Systemic administration of a nanoparticle of the disclosure can also be by intravenous, transmucosal, subcutaneous, intraperitoneal, intramuscular or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the formulation into salves, gels, or creams as generally known in the art.

The pyrvinium pamoate nanoparticles can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, for example those embodiments wherein the composition comprising pyrvinium pamoate is administered with one or more additional cancer therapies, the nanoparticle comprises pyrvinium pamoate and one or more additional therapeutic or chemotherapeutic agents. For example, the nanoparticle comprises pyrvinium pamoate and Paclitaxel, Docetaxel, Vincristine, Vinorelbine, Cisplatin, Carboplatin, Oxaliplatin, Irinotecan, Etoposide, 5-FU, Doxorubicin, Temozolomide, Dacarbazine, Cyclophosphamide, Ifosfamide, Abemaciclib, Gemcitabine, Erlotinib, Imatinib or Sorafenib. In some embodiments, the nanoparticle comprises a synergistic combination of pyrvinium and one or more therapeutic or chemotherapeutic agents.

Cancers

The methods of the disclosure are not intended to be limited to any particular sort of cancer. Indeed, given the effects of pyrvinium pamoate on multiple cellular pathways, treatment methods comprising administering a therapeutically effective amount of a composition comprising pyrvinium pamoate or a pyrvinium combinational therapy to a subject with a cancer are anticipated to be effective on a wide array of cancers in which these cellular pathways have been implicated.

The effectiveness of pyrvinium pamoate or a pyrvinium combinational therapy in the treatment of particular cancer or type of cancer can be assayed using a variety of in vitro and in vivo models, as well be set forth in greater detail in the Examples. One approach to determining the effectiveness of pyrvinium pamoate or a pyrvinium combinational therapy in the treatment of cancer comprises administering increasing concentrations of pyrvinium pamoate or pyrvinium pamoate and an additional chemotherapeutic agent to an exemplary cancer cell line, and determining the $IC_{50}$ value. As used herein, the term "$IC_{50}$ value" refers to the concentration of a compound wherein the cell viability is reduced by half. The $IC_{50}$ is thus a measure of the effectiveness of a compound in inhibiting a biological process. In this model, cancerous cell lines indicative of the various cancers of the disclosures are cultured using standard techniques, treated with pyrvinium pamoate, and the $IC_{50}$ value is calculated after 24, 48 or 72 hours to determine the effectiveness of pyrvinium pamoate or a pyrvinium pamoate combination therapy in killing the cancer cells.

Alternatively, or in addition, the effectiveness of pyrvinium pamoate or a pyrvinium pamoate combinational therapy can be assayed in vivo using a standard cell line xenograft or a patient derived xenograft mouse model. In patient derived xenograft mice, cancerous cells isolated from a cancer patient or from a cancer cell line are implanted into an immunodeficient mouse, and allowed to form tumors. The mice are then administered pyrvinium pamoate or pyrvinium pamoate in combination with an additional chemotherapeutic or therapeutic agent, and the effect on tumor size and mouse survival is assayed. As xenograft cancers can be implanted from a variety of cell lines and patient sources, the effectiveness of a treatment comprising pyrvinium pamoate on multiple cancers can be assayed in this manner.

In some embodiments, the cancer treated by a composition comprising a therapeutically effective amount of pyrvinium pamoate and, optionally, an additional chemotherapeutic or therapeutic agent comprises a commonly occurring cancer. In some embodiments, the cancer treated by a composition comprising a therapeutically effective amount of pyrvinium pamoate or a pyrvinium pamoate combination therapy comprises a colorectal cancer, a gastric cancer, a brain cancer, a colon cancer, a breast cancer, a liver cancer, a lung cancer, an ovarian cancer, a pancreatic cancer or a renal cancer.

In some embodiments, the cancer treated by a composition comprising a therapeutically effective amount of pyrvinium pamoate, and optionally a pyrvinium pamoate combinational therapy comprises a colon cancer. Colon cancers are cancers of the large intestine, or colon, which is the final part of the digestive tract. In some embodiments, colon cancers begin as small noncancerous clumps of cells called adenomatous polyps. These polyps typically form on the inner walls of the large intestine. In some embodiments, colon cancer cells can metastasize throughout the body. Typically, colon cancer occurs in people who are over 50 years of age. Risk factors include obesity, diet, smoking, and genetic factors.

In some embodiments, the cancer treated by a composition comprising a therapeutically effective amount of pyrvinium pamoate, and optionally a pyrvinium pamoate combinational therapy comprises a colorectal cancer. Colorectal cancers comprise cancers of the colon or rectum. The rectum is the passageway that connects the colon to the anus. In certain embodiments, the colorectal cancer comprises a colorectal carcinoma.

In some embodiments, the cancer treated by a composition comprising a therapeutically effective amount of pyrvinium pamoate, and optionally a pyrvinium pamoate combinational therapy comprises a gastric cancer. Gastric cancers comprise cancers which form from the cells of the lining of the stomach. In some embodiments, the gastric cancer comprises a gastrointestinal stromal cell tumor (GIST), a lymphoma, a carcinoid tumor, a squamous cell carcinoma, a small cell carcinoma or a leiomyosarcoma. GISTs may be malignant or benign. GISTs are most commonly found in the stomach and small intestine, but may be found anywhere in in or near the gastrointestinal tract. In some embodiments, a GIST may arise from the interstitial cells of Cajal. A lymphoma is a cancer of the lymph nodes and lymphatic system. A gastric lymphoma may be a primary lymphoma (i.e., a lymphoma that originates in the stomach itself), or a secondary lymphoma that originated elsewhere and metastasized to the stomach. Gastric squamous cell carcinomas are extremely rare. Squamous cell carcinomas arise from abnormal squamous cells, which are cells in the upper layer of the skin. Small cell carcinomas are a highly malignant type of cancer that most frequently occur in the lungs, but can arise in the cervix, prostate, liver pancreas, gastrointestinal tract or bladder.

In some embodiments, the cancer treated by a composition comprising a therapeutically effective amount of pyrvinium pamoate, and optionally a pyrvinium pamoate combinational therapy comprises a brain cancer. Brain cancers comprise cancers that form from cells of the brain. Alternatively, or in addition, brain cancers comprise cancers located in, on or in close proximity to the brain. There are many types of brain cancers. Exemplary but non-limiting brain cancers comprise gliomas, neuromas, astrocytomas, glioblastomas, craniopharyngiomas and medulloblastomas. Gliomas are cancers that originate in glial cells of the central nervous system. Glial cells are cells that surround neurons and provide supporting functions for those neurons. Gliomas can form in the brain or spinal chord. Exemplary types of glial cells comprise oligodendrocytes, astrocytes, ependymal cells Schwann cells, microglia and satellite cells.

In some embodiments, the cancer treated by a composition comprising a therapeutically effective amount of pyrvinium pamoate, and optionally a pyrvinium pamoate combinational therapy comprises a liver cancer. Liver cancers comprise cancers that form from cells of the liver. Exemplary but non-limiting liver cancers include hepatocellular carcinoma, cholangiocarcinoma and hepatoblastoma. In some embodiments, the liver cancer comprises a hepatocellular carcinoma. In some embodiments, the hepatocellular carcinoma occurs in a patient with chronic liver disease and cirrhosis. In some embodiments, the hepatocellular carcinoma forms from hepatic stem cells. In some embodiments, the liver cancer comprises a cholangiocarcinoma. In some embodiments, the cholangiocarcinoma forms in the bile ducts just outside the liver. In some embodiments, the cholangiocarcinoma is intrahepatic, extrahepatic (i.e., perihilar) or a distal extrahepatic cholangiocarcinoma. In some embodiments, the liver cancer comprises a hepatoblastoma. In some embodiments, the hepatoblastoma occurs in a child or an infant. In some embodiments, the hepatoblastoma originates from immature liver precursor cells. In some embodiments, the hepatoblastoma originates from pluripotent stem cells. In some embodiments, risk factors for liver cancer include obesity, diet, smoking, and genetic factors.

In some embodiments, the cancer treated by a composition comprising a therapeutically effective amount of pyrvinium pamoate, and optionally a pyrvinium pamoate combinational therapy comprises a lung cancer. In some embodiments, the lung cancer is a small cell lung cancer. In some embodiments, the small cell lung cancer is a small cell carcinoma (oat cell cancer) or a combined small cell carcinoma. In some embodiments, the small cell carcinoma comprises a neuroendocrine subtype of lung cancer that likely arises from neuroendocrine cells in the lung. Risk factors include asbestos exposure and smoking. In some embodiments, the lung cancer is a non-small cell lung cancer. In some embodiments, the non-small cell lung cancer is a non-small cell lung carcinoma. In some embodiments, the non-small cell lung carcinoma is an epithelial lung cancer other than small cell lung carcinoma. In some embodiments the non-small cell lung cancer is an adenocarcinoma, a squamous cell (epidermoid) carcinoma, an adenosquamous carcinoma or a sarcomatoid carcinoma. Squamous cells are flat cells that line the insides of the airways in the lungs.

In some embodiments, the cancer treated by a composition comprising a therapeutically effective amount of pyrvinium pamoate, and optionally a pyrvinium pamoate combinational therapy comprises a pancreatic cancer. Pancreatic cancers typically arise from the cells in the pancreas, a glandular organ behind the stomach. In some, more frequent, embodiments, the pancreatic cancer is a pancreatic adenocarcinoma. Typically pancreatic adenocarcinomas arise from the part of the pancreas which makes digestive enzymes. In some embodiments, the pancreatic cancer is a neuroendocrine tumor, which arises from the hormone producing cells of the pancreas.

In some embodiments, the cancer treated by a composition comprising a therapeutically effective amount of pyrvinium pamoate, and optionally a pyrvinium pamoate combinational therapy comprises a renal cancer. Renal cancers are cancers that arise from cells of the kidney. In some embodiments, the renal cancer first appears in the tubules of the kidney. In some embodiments, the renal cancer is an adult cancer. In some embodiments, the renal cancer is a pediatric cancer. In some embodiments, the renal cancer is a renal cell carcinoma, an inherited papillary renal cell carcinoma, a urothelial cell carcinoma of the renal pelvis, a squamous cell carcinoma, a juxtaglomerular cell tumor (reninoma), an angiomyolipoma, a renal oncocytoma, a Bellini duct carcinoma, a clear-cell sarcoma of the kidney, a mesoblastic nephroma, a Wilms' tumor (usually diagnosed in children under 5 years of age) or a mixed epithelial stromal tumor.

In some embodiments, the cancer treated by a composition comprising a therapeutically effective amount of pyrvinium pamoate, and optionally a pyrvinium pamoate combinational therapy comprises a rare cancer. Rare cancers are cancer that affect a very small number of people. Rare cancers are defined by the National Cancer Institute as cancers that occur in less than 15 cases per 100,000 people per year. Alternatively, a consortium from the European Union (RARECARE) defines rare cancers as those with few than 6 cases per 100,000 people per year. Alternatively, or in addition, a cancer might be considered rare if it starts in an unusual place in the body, or if it is of an unusual type and needs special treatment.

In some embodiments, the rare cancer treated by a composition comprising a therapeutically effective amount of pyrvinium pamoate, and optionally a pyrvinium pamoate combinational therapy comprises a blastoma. Blastomas are cancers that arise from precursor cells, also known as blast cells. As used herein, the term "blast cells" refers to immature, not fully differentiated cells in the body. Exemplary blast cells comprise bone marrow blast cells. In some embodiments, the subject with a blastoma is a child. In some embodiments, the subject with a blastoma is an adult. Exemplary but not limiting blastomas comprise nephroblastoma, medulloblastoma, retinoblastoma and neuroblastoma.

In some embodiments, the blastoma is a neuroblastoma. In some embodiments, neuroblastomas are cancers that begin in certain forms of nerve cells typically found in an embryo or fetus. In some embodiments, the nerve cells that give rise to the neuroblastoma are neuroblasts. Neuroblastomas occur most frequently in infants and young children, and are found only rarely in subjects older than ten years of age. In some embodiments, the neuroblastoma starts in the adrenal gland. In some embodiments, the neuroblastoma starts in the sympathetic nerve ganglia in the abdomen. In some embodiments, the neuroblastoma starts in the sympathetic nerve ganglia near the spine in the chest, neck or pelvis. In some embodiments, the neuroblastoma is a ganglioneuroblastoma. In some embodiments, the ganglioneuroblastoma comprises both malignant and benign components.

In some embodiments, the blastoma is a glioblastoma, also known as glioblastoma multiforme. In some embodiments, the glioblastoma forms from astrocytes. Astrocytes, also known as astroglia, are star shaped glial cells in the brain and spinal chord. Astrocytes perform a variety of functions in the nervous system, including but not limited to axon guidance, synaptic support, and control of the blood flow. In some embodiments, the glioblastoma is an astrocytoma. In some embodiments, the glioblastoma is a primary glioblastoma. Primary glioblastomas develop rapidly de novo without clinical or histological evidence of a less malignant precursor lesion. Primary glioblastomas frequently occur in the elderly. In some embodiments, the glioblastoma is a secondary glioblastoma. In some embodiments, the secondary glioblastoma progresses from a low grade diffuse astrocytoma or an anaplastic astrocytoma. Secondary glioblastomas frequently occur in younger patients and have a lesser degree of necrosis. Secondary glioblastomas are frequently located in the frontal lobe. In some embodiments, the glioblastoma is an astrocytoma. In some embodiments, the glioblastoma forms in the brain or in the nerve chord.

In some embodiments, the rare cancer treated by a composition comprising a therapeutically effective amount of pyrvinium pamoate, and optionally a pyrvinium pamoate combinational therapy comprises a carcinoma. Carcinomas are cancers that arise from epithelial tissues of the skin and mucous membranes or linings of internal organs, glands, the bladder and nerves and so forth. In early stages, a carcinoma will be confined to the layer of the tissue in which it started. In later stages, the carcinoma spreads to surround tissues, and metastasizes throughout the body. In some embodiments, rare carcinomas to be treated by the methods of the disclosure comprise acinic cell carcinoma, adenoid cystic carcinoma (ACC), adrenocortical carcinoma, adenocarcinoma of the appendix, ameloblastic carcinoma, basal cell carcinoma (infundibulocystic), basal cell carcinoma (multiple), carcinoma of the vocal tract, childhood carcinoma of unknown primary site, childhood hepatocellular carcinoma, choriocarcinoma, choroid plexus carcinoma, chromophil renal cell carcinoma, clear cell renal cell carcinoma, collecting duct carcinoma, eccrine mucinous carcinoma, eccrine porocarcinoma, embryonal carcinoma, epithelial-myoepithelial carcinoma, fibrolamelar carcinoma, glassy cell carcinoma of the cervix, hereditary renal cell carcinoma, intrahepatic cholangiocarcinoma, keratosis palmoplantaris adenocarcinoma of the colon, krukenberg carcinoma, lung adenocarcinoma, Merkel cell carcinoma, metaplastic carcinoma of the breast, mucoepidermoid carcinoma, myoepithelia carcinoma, nasopharyngeal carcinoma, nevoid basal cell carcinoma syndrome, ovarian small cell carcinoma, pancreatic carcinoma, papillary cystadenocarcinoma, papillary renal cell carcinoma, papillary thyroid carcinoma, parathyroid carcinoma, polymorphous low grade adenocarcinoma, familial renal carcinoma, renal cell carcinoma 4, secretory breast carcinoma, sinonasale undifferentiated carcinoma, small cell carcinoma of the bladder, rare adenocarcinoma of the breast, transitional cell carcinoma and urachal adenocarcinoma. Alternatively, or in addition, in some embodiments, rare carcinomas to be treated by the methods of the disclosure comprise adenoid cystic carcinoma (ACC), uterine serous carcinoma, adrenocortical carcinoma, gastric carcinoma, ovarian carcinoma thymic carcinoma, cholangiocarcinoma, colorectal carcinoma and esophageal carcinoma.

In some embodiments, the rare carcinoma is an adenoid cystic carcinoma (ACC). ACC is a rare form of adenocarcinoma, a cancer that begins in glandular tissues. ACC is found mainly in the head and neck, but can occasionally occur in other locations, such as the uterus, the trachea, the lacrimal gland, breast, skin or vulva. As such, in some embodiments ACC can comprise a salivary gland cell, a trachea cell, a lacrimal gland cell, a breast cell, a skin cell or a vulval cell. In some common embodiments, ACC occurs in the salivary glands scattered throughout the upper aerodigestive tract. In some embodiments, ACC spreads along the nerves or through the bloodstream. In some embodiments, ACC will spread to the lymph nodes, the lungs or a combination thereof. In some embodiments, ACC is classified based on histological variations in the tumor. Exemplary classifications include cylindroma, cribiform or solid.

In some embodiments, the rare carcinoma is a uterine serous carcinoma. Also called papillary serous carcinoma, uterine papillary serous carcinoma (UPSC), endometrial type 2 tumor, uterine serous carcinoma is a rare form of endometrial cancer that typically arises in postmenopausal women. In some embodiments, uterine serous carcinoma is associated with mutations in the p53 tumor suppressor. In some embodiments, uterine serous carcinoma may spread throughout the abdomen. In some embodiments, the uterine serous carcinoma may be a superficial endometrial tumor with extensive peritoneal disease.

In some embodiments, the rare carcinoma is an adrenocortical carcinoma. In adrenocortical carcinoma, the cancer forms on the cortex (the outer layer) of the adrenal gland. The adrenal gland sits on top of the kidney, and the cortex makes hormones. In some embodiments, these hormones include hormones involved in water and salt homeostasis and blood pressure. In some embodiments, the adrenocortical carcinoma comprises a tumor that increases the amount of hormones produced by the adrenal cortex. In some embodiments, genetic disorders such as Li-Fraumeni syndrome, Beckwith-Wiedemann syndrome and Carney complex increase the risk of a subject with the disorder of developing adrenocortical carcinoma.

In some embodiments, the rare carcinoma is an ovarian carcinoma. In some embodiments, an ovarian carcinoma is a carcinoma that forms on or in an ovary of a subject. In some embodiments, the carcinoma forms on the fallopian tubes. In some, more frequent, embodiments, the ovarian carcinoma is an epithelial ovarian carcinoma. In some embodiments, the ovarian carcinoma is a papillary serous carcinoma. In some embodiments, the ovarian carcinoma comprises a germ cell carcinoma. The most common types of germ cell carcinomas are teratomas, dysgermimomas and endodermal sinus tumors. In some embodiments, the ovarian carcinoma comprises a stromal carcinoma. An ovarian stromal carcinoma develops from the connective tissue cells that hold the ovary together and produce female hormones such as estrogen and progesterone. Ovarian stromal carcinomas comprise granulosa cell tumors and Steroli-Leydig cell tumors. In some embodiments, the ovarian carcinoma comprises a small cell carcinoma of the ovary. Small cell carcinomas of the ovary are rare, highly malignant, and typically affect young women. Small cell carcinomas of the ovary comprise pulmonary, neuroendocrine and hypercalcemic small cell carcinomas of the ovary. In some embodiments, the ovarian carcinoma comprises endometrioid ovarian carcinoma. Endometrioid ovarian carcinomas are characterized by their resemblance to the endometrium, the epithelial layer that lines the uterus. They are a type of surface epithelial tumors, and can be found in the endometrium or ovary.

In some embodiments, the rare carcinoma is a gastric carcinoma. In some embodiments, the gastric carcinoma comprises an adenocarcinoma. Gastric adenocarcinomas develop from the cells that form the innermost lining of the stomach, also known as mucosa. Rarely, in some embodiments, gastric cancers arise from cells in the walls of the stomach called interstitial cells of Cajal (GIST tumors, also known as a gastrointestinal stromal tumor). In some embodiments, gastric cancers comprise carcinoid tumors. Carcinoid tumors arise from hormone producing cells of the stomach. In some rare embodiments, a squamous cell carcinoma, a small cell carcinoma or a leiomyosarcoma can form from cells of the stomach. There are many risk factors for gastric cancers. Exemplary risk factors comprise *Helicobacter pylori* infection, diet, Epstein-Barr virus infection, chronic inflammation, smoking and hereditary factors.

In some embodiments, the rare cancer treated by a composition comprising a therapeutically effective amount of pyrvinium pamoate and optionally, a pyrvinium pamoate combinational therapy, comprises a cholangiocarcinoma. Cholangiocarcinomas are tumors arising in the cells of the connective tissues of the bile ducts. In some embodiments, liver disease or colitis increases the risk of a subject developing cholangiocarcinoma. In some embodiments, the cholangiocarcinoma comprises an intrahepatic bile duct cancer. Intrahepatic bile duct cancers form in the bile ducts inside the liver. In some embodiments, the cholangiocarcinoma comprises an extrahepatic bile duct cancer. In some embodiments, the extrahepatic bile duct cancers form in the perihilar bile duct or the distal extrahepatic bile duct. In some embodiments, a subject with a cholangiocarcinoma produces a higher than normal level of a tumor marker such as CEA or CA 19-9 in blood, urine or tissue.

In some embodiments, the rare cancer treated by a composition comprising a therapeutically effective amount of pyrvinium pamoate, and optionally a pyrvinium pamoate combinational therapy comprises a neuroendocrine cancer. In some embodiments, the neuroendocrine cancer comprises a thymic cancer. In some embodiments, the thymic cancer comprises a thymic carcinoma or a thymoma. Thymic carcinomas are tumors that form on the outside surface of the thymus, a gland in the upper chest. In some embodiments, the thymic carcinoma is derived from thymic epithelia cells. In some embodiments, early thymic carcinoma may be asymptomatic, so that a thymic carcinoma of a subject is only identified late in the progression of the disease. In some embodiments, the thymic carcinoma may be highly aggressive. In some embodiments, the overall 5-year survival rate for patients with thymic carcinoma is only 30-50%. In some embodiments, the thymic cancer comprises a thymoma. In some embodiments, the cells of a thymoma tend to resemble normal thymus cells, grow slowly and rarely spread beyond the thymus.

In some embodiments, the rare cancer treated by a composition comprising a therapeutically effective amount of pyrvinium pamoate, and optionally a pyrvinium pamoate combinational therapy comprises a sarcoma. Sarcomas are rare cancers that arise from mesenchymal cells. In some embodiments, the sarcoma comprises a malignant tumor comprising cells arising from cancellous bone, cartilage, fat, muscle, vasculature or hematopoietic tissues. In some embodiments, the sarcoma comprises adenosarcoma of the uterus, alveolar soft part sarcoma, angiosarcoma of the breast, angiosarcoma of the liver, angiosarcoma of the scalp, cerebral sarcoma, chondrosarcoma, chromophil renal cell sarcoma, embryonal sarcoma, endemic Kaposi sarcoma, endometrial stromal sarcoma, Ewing's sarcoma, fibrosarcoma, gliosarcoma, Langerhans cell sarcoma, leiomyosarcoma, lymphosarcoma, malignant teratocacinosarcoma, microcystic adnexal carcinoma, myxoid liposarcoma, neurofibrosarcoma, oral squamous sarcoma, osteosarcoma, ovarian carcinosarcoma, paraganglioma and gastric stromal sarcoma, plexosarcoma, radiation induced angiosarcoma of the breast, alveolar rhabdomyosarcoma, embryonal rhabdomyosarcoma, soft tissue sarcoma, childhood soft tissue sarcoma, synovial sarcoma, undifferentiated pleiomorphic sarcoma, uterine carcinosarcoma or uterine sarcoma. Alternatively, or in addition, the sarcoma comprises an Ewing's sarcoma, a leiomyosarcoma, an angiosarcoma or a rhabdomyosarcoma.

In some embodiments, the rare cancer treated by a composition comprising a therapeutically effective amount of pyrvinium pamoate, and optionally a pyrvinium pamoate combinational therapy comprises an Ewing's sarcoma. Ewing's sarcoma comprises tumors of the bones, the soft tissue surrounding bones such as cartilage and nerves, or a combination thereof. Ewing's sarcoma typically affects children and young adults, although it can occur at any age. Ewing's sarcoma can occur in any bone. In some more frequent embodiments, Ewing's sarcoma begins in the leg bones, hipbones, arm bones, and bones in the chest, skull or spine. In some less common embodiments, Ewing's sarcoma occurs in the soft tissues of the arms, legs, abdomen, chest, neck, head or a combination thereof. In some embodiments of Ewing's sarcoma, there is no bone involvement. In some embodiments, treatments for Ewing's sarcoma comprise chemotherapy, surgery, or a combination thereof. In some embodiments, the chemotherapy comprises neoadjuvant chemotherapy, which may comprise vincristine, doxorubicin and cyclophosphamide with ifosfamide and etoposide. In some embodiments, Ewing's sarcoma is associated with a chromosomal translocations affecting the EWSR1 (EWS RNA binding protein 1), FLI1 (Fli-1 proto-oncogene), ERG (ERG, ETS transcription factor) and ETV1 (ETS variant 1) genes.

In some embodiments, the rare cancer treated by a composition comprising a therapeutically effective amount of pyrvinium pamoate, and optionally a pyrvinium pamoate combinational therapy comprises a leiomyosarcoma. Leiomyosarcomas are a type of soft tissue sarcoma. In some embodiments, the leiomyosarcoma comprises a malignant tumor that arises from smooth muscle cells. Smooth muscles cells are the cells of involuntary muscles, i.e. muscles over which the brain has no voluntary control. Exemplary involuntary muscles comprise the walls of the digestive tract and muscles controlling salivary gland secretions. In some embodiments, the leiomyosarcoma grows and spreads into surrounding tissues. In some embodiments, the leiomyosarcoma spreads to distant sites of the body via the bloodstream or lymphatic system, or both. In some embodiments, a leiomyosarcoma can form almost anywhere where there are blood vessels, such as the heart, liver, pancreas, genitourinary and gastrointestinal tract, the space behind the abdominal cavity (retroperitoneum), the uterus or skin. In some of the more common embodiments, the leiomyosarcoma forms in the uterus. Symptoms, diagnosis and treatment of leiomyosarcomas varies depending on the location and stage of the cancer.

In some embodiments, the rare cancer treated by a composition comprising a therapeutically effective amount of pyrvinium pamoate, and optionally a pyrvinium pamoate combinational therapy comprises an angiosarcoma. Angiosarcomas are sarcomas arising from cells of the inner lining of the blood vessels. Angiosarcomas can occur in any area of the body. In some embodiments, the angiosarcoma occurs in the skin, breast, liver, heart, spleen or deep tissue. In some embodiments, the angiosarcoma forms on the skin of the head and neck. In some embodiments, the rare cancer treated by a composition comprising a therapeutically effective amount of pyrvinium pamoate, and optionally a pyrvinium pamoate combinational therapy comprises a rhabdomyosarcoma. In some embodiments, the rhabdomyosarcoma comprises an embryonal rhabdomyosarcoma. Embryonal rhabdomyosarcomas typically affect children in their first five years of life. The cells of an embryonal rhabdomyosarcoma comprise cells that resemble the developing muscle cells of a six to eight week embryo. In some embodiments, embryonal rhabdomyosarcomas comprise rhabdomyosarcomas of the head and neck area, bladder vagina, or in or around the prostate and testicles. In some embodiments, embryonal rhabdomyosarcomas comprise botryoid and spindle rhabdomyosarcomas. In some embodiments, the rhabdomyosarcoma comprises an alveolar rhabdomyosarcoma. Alveolar rhabdomyosarcomas typically affect all age groups equally. Alveolar rhabdomyosarcomas typically occur in the large muscles of the trunk, arms and legs. The cells of an alveolar rhabdomyosarcoma comprise cells that resemble those of normal muscle cells seen in a ten week old fetus. In some embodiments, the rhabdomyosarcoma comprises an anaplastic rhabdomyosarcoma.

In some embodiments, the rare cancer treated by a composition comprising a therapeutically effective amount of pyrvinium pamoate, and optionally a pyrvinium pamoate combinational therapy comprises a neuroendocrine cancer. Neuroendocrine cancers arise from cells of the endocrine (hormonal) and nervous systems. In some embodiments, the neuroendocrine cancer comprises a carcinoid tumor. Carcinoid tumors are a type of slow growing tumor that comprise neuroendocrine cells and can arise at various places throughout the body. In some embodiments the carcinoid tumor comprises a small intestine tumor, an appendix tumor, a tumor of the rectum, a tumor of the bronchial system, a brain tumor, colon tumor, a stomach tumor, a pancreatic tumor, a liver tumor, a gallbladder tumor, a bile duct tumor, an ovarian tumor, a testicular tumor, a bladder tumor, a tumor of the prostate gland, a breast tumor, a kidney tumor, a thymic tumor, an eye tumor or an ear tumor. In some embodiments, the neuroendocrine cancer comprises a thymic cancer.

In some embodiments, the rare cancer treated by a composition comprising a therapeutically effective amount of pyrvinium pamoate, and optionally a pyrvinium pamoate combinational therapy comprises a mesothelioma. Mesotheliomas comprise cancers that develop from the mesothelial, a thin layer of tissue lining lungs, abdomen or heart. In some embodiments, mesotheliomas affect the pleura that surrounds the lungs (pleural mesothelioma). In some embodiments, mesotheliomas affect the tissue of the abdomen (peritoneal mesothelioma). Risk factors for mesothelioma comprise asbestos exposure.

In some embodiments, the rare cancer treated by a composition comprising a therapeutically effective amount of pyrvinium pamoate, and optionally a pyrvinium pamoate combinational therapy comprises a chordoma. Chordomas comprise cancerous tumors that occur along the spine. Chordomas are thought to arise from the cellular remnants of the notochord, the embryonic tissue that eventually forms the intervertebral disks. In some embodiments, the chordoma grows slowly, gradually extending into the surrounding bone and soft tissue. In some embodiments, the chordoma is relatively benign. In some embodiments, the chordoma is malignant.

In some embodiments, the rare cancer treated by a composition comprising a therapeutically effective amount of pyrvinium pamoate, and optionally a pyrvinium pamoate combinational therapy comprises a pheochromocytoma, sometimes also referred to as a paraganglioma when the cancer arises in a chromaffin cell outside of the adrenal gland. A pheochromocytoma/paraganglioma is a rare tumor that develops in a chromaffin cell either in the adrenal gland or in the parasympathetic-associated tissues.

An exemplary, but non-limiting list of rare cancers that can be treated by the methods of the disclosure can be found at rarediseases.info.nih.gov/diseases/diseases-by-category/1/rare-cancers, the contents of which are herein incorporated by reference in their entirety. A list of rare cancers treatable by the methods of the disclosure is set forth in Table 1, below.

TABLE 1

| Rare Cancers |
|---|
| 5q-syndrome |
| A |
| Acinic cell carcinoma |
| Acromegaly |
| ACTH-secreting pituitary adenoma |
| Acute lymphoblastic leukemia |
| Acute megakaryoblastic leukemia |
| Acute myeloblastic leukemia with maturation |
| Acute myeloid leukemia with abnormal bone marrow eosinophils inv(16)(p13q22) or t(16;16)(p13;q22) |
| Acute myelomonocytic leukemia |
| Acute panmyelosis with myelofibrosis |

TABLE 1-continued

| Rare Cancers |
|---|
| Adenocarcinoid tumor |
| Adenoid cystic carcinoma |
| Adrenal cancer |
| Adrenocortical carcinoma |
| Aicardi syndrome |
| Ameloblastic carcinoma |
| Anal cancer |
| Anaplastic ependymoma |
| Anaplastic large cell lymphoma |
| Anaplastic oligodendroglioma |
| Anaplastic small cell lymphoma |
| Angioimmunoblastic T-cell lymphoma |
| Angioma serpiginosum, autosomal dominant |
| Angiosarcoma of the breast |
| Angiosarcoma of the scalp |
| Ataxia telangiectasia |
| Autoimmune lymphoproliferative syndrome |
| Acral lentiginous melanoma |
| Acrospiroma |
| Acute erythroid leukemia |
| Acute lymphoblastic leukemia congenital sporadic aniridia |
| Acute monoblastic leukemia |
| Acute myeloblastic leukemia without maturation |
| Acute myeloid leukemia with inv3(p21;q26.2) or t(3;3)(p21;q26.2) |
| Acute non lymphoblastic leukemia |
| Acute promyelocytic leukemia |
| Adenocarcinoma of the appendix |
| Adenosarcoma of the uterus |
| Adrenal medulla cancer |
| Aggressive NK cell leukemia |
| Alveolar soft part sarcoma |
| AML with myelodysplasia-related features |
| Anaplastic astrocytoma |
| Anaplastic ganglioglioma |
| Anaplastic oligoastrocytoma |
| Anaplastic plasmacytoma |
| Angiofollicular lymph hyperplasia |
| Angioma hereditary neurocutaneous |
| Angioma serpiginosum, X-linked |
| Angiosarcoma of the liver |
| Astroblastoma |
| Atrial myxoma, familial |
| B |
| B cell prolymphocytic leukemia |
| Bannayan-Riley-Ruvalcaba syndrome |
| Basal cell carcinoma, multiple |
| Becker nevus syndrome |
| Benign metastasizing leiomyoma |
| Bile duct cancer |
| Birt-Hogg-Dube syndrome |
| Blastic plasmacytoid dendritic cell |
| Blue rubber bleb nevus syndrome |
| Brain stem cancer |
| Brain tumor, childhood |
| BRCA2 hereditary breast and ovarian cancer syndrome |
| Breast cancer, male |
| Brenner tumor of the vagina |
| Burkitt lymphoma |
| B-cell lymphoma |
| Basal cell carcinoma, infundibulocystic |
| Bazex-Dupre-Christol syndrome |
| Bednar tumor |
| Benign multicystic peritoneal mesothelioma |
| Bilialy tract cancer |
| Bladder cancer, childhood |
| Bloom syndrome |
| Bowen's disease |
| Brain tumor, adult |
| BRCA1 hereditary breast and ovarian cancer syndrome |
| Breast cancer, childhood |
| Brenner tumor of ovary |
| Bronchial adenomas/carcinoids childhood |
| Buschke Lowenstein tumor |

TABLE 1-continued

Rare Cancers

C

Capillary hemangioblastoma
Carcinoid tumor
Carcinoid tumor childhood
Carney complex
Carotid body tumor
CDK4 linked melanoma
Central neurocytoma
Cerebellar liponeurocytoma
Cerebral sarcoma
Cerebro-oculo-facio-skeletal syndrome
CHILD syndrome
Childhood brain stem glioma
Chordoid glioma of the third ventricle
Choriocarcinoma
Choroid plexus papilloma
Chronic lymphocytic leukemia
Clear cell renal cell carcinoma
Cockayne syndrome type I, type II and type III
Common variable immunodeficiency
Cowden syndrome
Cronkhite-Canada disease
Cutaneous T-cell lymphoma
Carcinoid syndrome
Carcinoma of the vocal tract
Carcinoma of unknown primary site, childhood
Carney triad
Cartilaginous cancer
Central nervous system germinoma
Cerebellar astrocytoma, childhood
Cerebral astrocytoma, childhood
Cerebral ventricle cancer
Cervical intraepithelial neoplasia
Childhood acute lymphoblastic leukemia
Chondrosarcoma
Chordoma
Choroid plexus carcinoma
Chromophil renal cell carcinoma
Chronic neutrophilic leukemia
CLOVES syndrome
Collecting duct carcinoma
Costello syndrome
Craniopharyngioma
Cutaneous mastocytoma

D

Deafness-lymphedema-leukemia syndrome
Denys-Drash syndrome
Desmoid tumor
Desmoplastic infantile astrocytoma
Diamond-Blackfan anemia
Diffuse astrocytoma
Diffuse gastric cancer
Digestive System Melanoma
Dysembryoplastic neuroepithelial tumor
Dyskeratosis congenita autosomal dominant
Dyskeratosis congenita X-linked
Dendritic cell tumor
Dermatofibrosarcoma protuberans
Desmoplastic infantile ganglioglioma
Desmoplastic small round cell tumor
Diaphyseal medullary stenosis with malignant fibrous histiocytoma
Diffuse cavernous hemangioma of the rectum
Diffuse Large B-Cell Lymphoma
Disseminated peritoneal leiomyomatosis
Dyskeratosis congenita
Dyskeratosis congenita autosomal recessive
Diffuse intrinsic pontine glioma

E

Eccrine mucinous carcinoma
Embryonal carcinoma
Embryonal tumor with multilayered rosettes
Endemic Kaposi sarcoma
Enteropathy-associated T-cell lymphoma
Epithelial-myoepithelial carcinoma
Esophageal cancer, childhood
Ewing sarcoma (Ewing's sarcoma)
Extragonadal germ cell tumor
Eccrine porocarcinoma
Embryonal sarcoma
Enchondroma
Endometrial stromal sarcoma
Ependymoma
Esophageal cancer
Essential thrombocythemia
Ewing's family of tumors
Extragonadal germ cell tumor

F

Fallopian tube cancer
Familial adenomatous polyposis
Familial cylindromatosis
Familial pancreatic cancer
Familial prostate cancer
Familial Wilms tumor 2
Fibrolamellar carcinoma
Follicular lymphoma
Functioning pancreatic endocrine tumor
Fallopian tube cancer
Familial colorectal cancer
Familial hyperaldosteronism type 2
Familial platelet disorder with associated myeloid malignancy
Familial stomach cancer
Fanconi anemia
Fibrosarcoma
Frasier syndrome

G

Gallbladder cancer
Ganglioglioma
Gastric lymphoma
Gastrointestinal Stromal Tumors
Giant congenital nevus
Glioblastoma
Gliosarcoma
Glomus tympanicum tumor
Glucagonoma
Goblet cell carcinoid
Granulomatous slack skin disease
Gray zone lymphoma
Gangliocytoma
Gardner syndrome
Gastro-enteropancreatic neuroendocrine tumor
Giant cell tumor of bone
Glassy cell carcinoma of the cervix
Glioma
Glomus jugulare tumors
Glomus vagale tumor
Glucagonoma syndrome
Granular cell tumor
Granulosa cell tumor of the ovary
Gynandroblastoma

H

Hairy cell leukemia
Hemangioblastoma
Hemangioma thrombocytopenia syndrome
Hemi 3 syndrome
Hereditary diffuse gastric cancer
Hereditary paraganglioma-pheochromocytoma
Hidradenocarcinoma
Hodgkin lymphoma, childhood
Hyaline fibromatosis syndrome
Hypopharyngeal cancer
Heart tumor
Hemangioendothelioma
Hemangiopericytoma
Hepatoblastoma
Hereditary leiomyomatosis and renal cell cancer
Hereditary multiple osteochondromas
Hereditary renal cell carcinoma
Hodgkin lymphoma TABLE 1-continued Rare Cancers Hurthle cell thyroid cancer
Hyperparathyroidism-jaw tumor syndrome
I Indolent B cell lymphoma
Inflammatory breast cancer
Inflammatory myofibroblastic tumor
Intrahepatic cholangiocarcinoma
Intraocular melanoma
Infantile myofibromatosis
Inflammatory linear verrucous epidermal nevus
Insulinoma
Intraneural perineurioma
J Juvenile myelomonocytic leukemia
Juvenile polyposis syndrome
K Kaposi sarcoma
Keratosis palmoplantaris adenocarcinoma of the colon
Klatskin tumor
Kaposiform Hemangioendothelioma
Kidney cancer, childhood
Krukenberg carcinoma
L Langerhans cell sarcoma
Laryngeal cancer
Ledderhose disease
Lentigo maligna melanoma
Leukemia subleukemic
Leukemia, T-cell, chronic
Li-Fraumeni syndrome
Lip and oral cavity cancer
Liposarcoma
Lymph Node Neoplasm
Lymphoma AIDS related
Lymphoma, large-cell
Lymphomatoid papulosis
Large granular lymphocyte leukemia
Laryngeal cancer, childhood
Leiomyosarcoma
LEOPARD syndrome
Leukemia, B-cell, chronic
Lhermitte-Duclos disease
Linear nevus sebaceous syndrome
Lipoblastoma
Lung adenocarcinoma
Lymphoblastic lymphoma
Lymphoma, gastric non Hodgkins type
Lymphoma, large-cell, immunoblastic
Lymphosarcoma
M Macrocephaly-capillary malformation
Mahvash disease
Malignant eccrine spiradenoma
Malignant melanoma, childhood
Malignant mesothelioma
Malignant peripheral nerve sheath tumor
Mantle cell lymphoma
Mediastinal endodermal sinus tumors
Medulloblastoma, childhood
Melanoma astrocytoma syndrome
Meningioma
Metaplastic carcinoma of the breast
Metastatic squamous neck cancer with occult primary
Microcystic lymphatic malformation
Mucoepidermoid carcinoma
Multicentric Castleman Disease
Multiple familial trichoepithelioma 1 and 2
Multiple myeloma
Myelocytic leukemia-like syndrome, familial, chronic
Myeloid leukemia
Myoepithelial carcinoma
Maffucci syndrome
Malignant cylindroma TABLE 1-continued Rare Cancers Malignant germ cell tumor
Malignant mesenchymoma
Malignant mixed Mullerian tumor
Malignant Teratocarcinosarcoma
McCune-Albright syndrome
Medulloblastoma
Melanocytic lesions of CNS
Melanoma, familial
Merkel cell carcinoma
Metastatic insulinoma
Microcystic adnexal carcinoma
Mosaic variegated aneuploidy syndrome
Muir-Torre syndrome
Multiple endocrine neoplasia type 1, 2A and 2B
Multiple fibrofolliculoma familial
Mycosis fungoides
Myelofibrosis
Myeloid sarcoma
Myxoid liposarcoma
N N syndrome
Nasopharyngeal cancer, childhood
Neural crest tumor
Neurocutaneous melanosis
Neuroepithelioma
Neurofibromatosis-Noonan syndrome
Nevoid basal cell carcinoma syndrome
Nevus of Ito
Nodular melanoma
Non-Hodgkin lymphoma, childhood
Non-involuting congenital hemangioma
Nonseminomatous germ cell tumor
Neuroectodermal tumor (primary)
Nasal cavity cancer, childhood
Nasopharyngeal carcinoma
Neuroblastoma
Neuroendocrine carcinoma of the cervix
Neurofibromatosis type 2
Neurofibrosarcoma
Nevus comedonicus syndrome
Nijmegen breakage syndrome
Non functioning pancreatic endocrine tumor
Non-Hodgkin lymphoma, during pregnancy
Non-small cell lung cancer, childhood
Noonan syndrome (1-6)
O Ocular melanoma
Oligoastrocytoma
Ollier disease
Optic pathway glioma
Oral squamous cell carcinoma
Orbital lymphoma
Oropharyngeal cancer, childhood
Osteofibrous dysplasia
Ovarian cancer
Ovarian epithelial cancer
Ovarian low malignant potential tumor
Olfactory neuroblastoma
Oligodendroglioma
Onychocytic matricoma
Oral cancer
Orbital lymphangioma
Oropharyngeal cancer, adult
Oslam syndrome
Osteosarcoma
Ovarian carcinosarcoma
Ovarian germ cell tumor
P Paget disease of the breast
Painful orbital and systemic neurofibromas-marfanoid habitus syndrome
Pancreatic cancer, childhood
Pancreatoblastoma
Papillary renal cell carcinoma
Paraganglioma and gastric stromal sarcoma

TABLE 1-continued

Rare Cancers

Paranasal sinus cancer, childhood
Parathyroid cancer, childhood
Pediatric T-cell leukemia
Penile cancer, childhood
Perlman syndrome
PHACE syndrome
Pheochromocytoma, childhood
Phyllodes tumor of the breast
Pilocytic astrocytoma
Pineal parenchymal tumors of intermediate differentiation
Pineoblastoma, childhood
Plasma cell leukemia
Pleuropulmonary blastoma
POEMS syndrome
Polyembryoma
Primary central nervous system lymphoma
Primary liver cancer
Primary malignant melanoma of the conjunctiva
Proliferating trichilemmal cyst
Proteus-like syndrome
Paget disease, extramammary
Pancreatic adenoma
Pancreatic islet cell tumors
Papillary cystadenocarcinoma
Papillary thyroid carcinoma
Paranasal sinus cancer, adult
Paraneoplastic cerebellar degeneration
Parathyroid carcinoma
Penile cancer, adult
Peripheral T-cell lymphoma
Peutz-Jeghers syndrome
Pheochromocytoma
Philadelphia-negative chronic myeloid leukemia
Phyllodes tumor of the prostate
Pilomatrixoma
Pineoblastoma
Pituitary cancer
Pleomorphic xanthoastrocytoma
Plexosarcoma
Polycythemia vera
Polymorphous low-grade adenocarcinoma
Primary effusion lymphoma
Primary malignant melanoma of the cervix
Primary melanoma of the central nervous system
Proteus syndrome
Pseudomyxoma peritonei

R

Radiation induced angiosarcoma of the breast
Radiation induced meningioma
Rectal cancer, childhood
Renal cell carcinoma 4
Retroperitoneal liposarcoma
Rhabdomyosarcoma alveolar
Richter syndrome
Rombo syndrome
Radiation induced cancer
Rare adenocarcinoma of the breast
Renal carcinoma, familial
Retinoblastoma
Rhabdoid tumor
Rhabdomyosarcoma embryonal
Ring dermoid of cornea

S

Sacrococcygeal Teratoma
Salivary gland cancer, childhood
Sarcoma botryoides
Schwannomatosis
Sertoli-leydig cell tumors
Sezary syndrome
Sideroblastic anemia pyridoxine-refractory autosomal recessive
Sinonasal undifferentiated carcinoma
Skin cancer, non melanoma, childhood
Small cell lung cancer, childhood and adult
Small intestine cancer

TABLE 1-continued

Rare Cancers

Soft tissue sarcoma childhood
Sotos syndrome
Stomach cancer
Subcutaneous panniculitis-like T-cell lymphoma
Subependymoma
Supraglottic laryngeal cancer
Supratentorial primitive neuroectodermal tumors, childhood
Synovial cancer
Saethre-Chotzen syndrome
Salivary gland cancer, adult
Schinzel Giedion syndrome
Secretory breast carcinoma
Severe congenital neutropenia autosomal recessive 3
Shwachman-Diamond syndrome
Simpson-Golabi-Behmel syndrome
Sinus cancer
Small cell carcinoma of the bladder
Small intestine cancer, childhood
Soft tissue sarcoma
Somatostatinoma
Splenic neoplasm
Stomach cancer, childhood
Subependymal giant cell astrocytoma
Superficial spreading melanoma
Supratentorial primitive neuroectodermal tumor
Supraumbilical midabdominal raphe and facial cavernous hemangiomas
Synovial sarcoma

T

T-cell lymphoma 1A
Teratoma with malignant transformation
Testicular cancer, childhood
Testicular yolk sac tumor
Thymic epithelial tumor
Thyroid cancer, anaplastic
Thyroid cancer, follicular
Tongue cancer
Transitional cell cancer of the renal pelvis and ureter
Trichofolliculoma
Tuberous sclerosis
Turcot syndrome
Tyrosinemia type 1
T-cell/histiocyte rich large B cell lymphoma
Testicular cancer
Testicular seminoma
Thoracolaryngopelvic dysplasia
Thymoma, childhood
Thyroid cancer, childhood
Thyroid cancer, medullary
Transient myeloproliferative syndrome
Transitional cell carcinoma
Trophoblastic tumor placental site
Tufted angioma
Tylosis with esophageal cancer
Teratoid Rhabdoid tumor (Atypical)

U

Undifferentiated pleomorphic sarcoma
Urachal adenocarcinoma
Urethral cancer
Uterine sarcoma
Unicentric Castleman disease
Urachal cancer
Uterine Carcinosarcoma

V

Vaginal cancer
VIPoma
Von Hippel-Lindau disease
Verrucous nevus acanthokeratolytic
Visual pathway and hypothalamic glioma, childhood
Vulvar cancer

W

WAGR syndrome
Werner's syndrome

TABLE 1-continued

Rare Cancers

Wilms tumor and radial bilateral aplasia
Wiskott Aldrich syndrome
Waldenstrom macroglobulinemia
White sponge nevus of cannon
Wilms' tumor
WT limb blood syndrome

X

X-linked lymphoproliferative syndrome
Xeroderma pigmentosum
X-linked lymphoprolifemtive syndrome 1

Z

Zollinger-Ellison syndrome
Zuska's disease

Pyrvinium Pamoate Therapies

In some embodiments of the methods of treating cancer of the disclosure, the administration of the composition comprising a therapeutically effective amount of pyrvinium pamoate comprises a cancer monotherapy. In some embodiments of the methods of treating cancer of the disclosure, the administration of the composition comprising a therapeutically effective amount of pyrvinium pamoate comprises is part of a cancer combinational therapy. The composition comprising pyrvinium pamoate can be combined with additional chemotherapeutic agents, cancer therapeutic agents, cancer combination therapies, targeted small molecules and biologics such as antibodies.

In some embodiments of the methods of treating cancer of the disclosure, the administration of the composition comprising a therapeutically effective amount of pyrvinium pamoate comprises a part of a cancer combinational therapy. In some embodiments, this combination therapy comprises treating a subject in need thereof with a composition comprising pyrvinium pamoate and a composition comprising at least one other therapeutic or chemotherapeutic agent.

The methods of, or compounds or medicaments for use in combination therapy with pyrvinium pamoate featured in the disclosure may result in a synergistic effect, wherein the effect of a combination of therapeutic agents (e.g. pyrvinium pamoate or a pharmaceutically acceptable salt thereof, and one or more second anti-cancer agents) is greater than the sum of the effects resulting from administration of any of the therapeutic agents as single agents. A synergistic effect may also be an effect that cannot be achieved by administration of any of the therapeutic agents as single agents. The synergistic effect may include, but is not limited to, an effect of treating cancer, e.g., by reducing tumor size, reducing the number or frequency of malignant cells in a subject or a sample obtained from a subject, inhibiting tumor growth, inhibiting growth, survival, or proliferation of malignant cells, or increasing survival of the subject. The synergistic effect may also include reducing cancer cell viability, inducing cancer cell death, and inhibiting or delaying cancer cell growth.

In some embodiments of the methods or compositions for use of the disclosure, the effect of pyrvinium pamoate or a pharmaceutically acceptable salt thereof and the one or more additional therapeutic agents may be additive. As used herein, "additive" refers to an effect on a cancer of a subject that is equal to, and not greater than sum of the effects of pyrvinium pamoate and the additional therapeutic agent were each administered to a subject alone. The additive effect may include, but is not limited to an effect of treating cancer, e.g., by reducing tumor size, reducing the number or frequency of malignant cells in a subject or a sample obtained from a subject, inhibiting tumor growth, inhibiting growth, survival, or proliferation of malignant cells, or increasing survival of the subject. The additive effect may also include reducing cancer cell viability, inducing cancer cell death, and inhibiting or delaying cancer cell growth.

All other additional chemotherapeutic agents known to one skilled in the art are contemplated for combination with pyrvinium pamoate. Exemplary, but non-limiting additional chemotherapeutic agents are described below.

In some embodiments, the additional chemotherapeutic agent may comprise a taxane. Taxanes are a class of diterpenes that have long been used in cancer treatment. Taxanes act by disrupting microtubule function, which in turn disrupts cell division. Typically, taxanes act by stabilizing GDP bound tubulin in the microtubule, disrupting microtubule depolymerization and dynamic instability of microtubules. Exemplary taxanes comprise Paclitaxel or Docetaxel, and analogs or derivatives thereof.

In some embodiments, the additional chemotherapeutic agent may comprise a Vinca alkaloid. Like taxanes, Vinca alkaloids also act upon tubulin. Vinca alkaloids prevent microtubule polymerization, thus preventing cell division. Exemplary but not limiting Vinca alkaloids comprise Vinblastine, Vincristine, Vinorelbine, Vincaminol, Vineridine, Vinburnine, Vindesine, Vincamine and analogs or derivatives thereof.

In some embodiments, the additional chemotherapeutic agent may comprise platinum based antineoplastic drug (platins). One mechanism of action by which platins work is through the crosslinking of DNA, which inhibits DNA repair, DNA synthesis, or both in cancer cells. Exemplary, but not limiting platins comprise Cisplatin or Carboplatin, and analogs or derivatives thereof.

In some embodiments, the additional chemotherapeutic agent may comprise a Topoisomerase I inhibitor or Topoisomerase II. Topoisomerase I and II are an enzymes which regulates DNA structure by breaking and rejoining the phosphodiester backbone of the DNA during the cell cycle (e.g., during DNA synthesis). Without functional Topoisomerase I or II, single and double strand breaks accumulate, leading to cell death. Exemplary but not limiting Topoisomerase I inhibitors comprise Irinotecan and analogs or derivatives thereof. Exemplary but not limiting Topoisomerase II inhibitors comprise Etoposide and analogs or derivatives thereof.

In some embodiments, the additional chemotherapeutic agent may comprise a thymidylate synthase inhibitor. Thymidylate synthase is a key enzyme involved in DNA synthesis. Exemplary but not limiting thymidylate synthase inhibitors comprise 5-Fluorouracil and analogs or derivatives thereof.

In some embodiments, the additional chemotherapeutic agent may comprise a DNA intercalating agent. DNA intercalating agents insert themselves into the structure of the DNA within a cell and bind to the DNA, causing DNA damage. This may kill cancer cells, or stop them from dividing. Exemplary but not limiting DNA intercalating agents comprise Doxorubicin and analogs or derivatives thereof.

In some embodiments, the additional chemotherapeutic agent may comprise a DNA alkylating agent. DNA alkylating agents attach an alkyl group to DNA, typically to the guanine base of the DNA. This causes DNA damage, and may kill the cancer cells or stop them from dividing. Exemplary but not limiting DNA alkylating agents comprise Dacarbazine and analogs or derivatives thereof and Temozolomide and analogs or derivatives thereof.

Additional chemotherapeutic agents that cause DNA damage, such as through the binding of DNA or interfering with DNA synthesis, are also considered as within the scope of the invention.

In some embodiments, the additional chemotherapeutic agent may comprise a cyclin dependent kinase (CDK) inhibitor. CDKs, together with cyclins, control the progression of the cell through the cell cycle. As cells divide, they pass through a number of checkpoints that divide the cell cycle into phases called growth 0 (no division), growth 1 (G1), synthesis (S, when DNA replication occurs), growth 2 (G2) and mitosis (M). Cyclin-CDK complexes regulate the progression of the cell through the phases of the cell cycle. Cyclins bind to their cognate CDKs with a degree of specificity, activating the CDK upon binding and allowing the CDK to phosphorylate targets and regulate the cell cycle. For example, CDK4 and CDK6 (CDK4/6) bind to D type cyclins. Upon binding to a D type cyclin, CDK4/6 phosphorylate RB, which leads to the induction of genes necessary to regulate G1 cellular activity. CDK4 binds to cyclins D1, D2, and D3 to regulate G1. CDK6 binds to cyclins D1, D2, and D3 to regulate G1. CDK2 binds to cyclin E to regulate the G1/S transition. CDK2 binds to cyclin A to regulate S phase. CDK1 binds to cyclin A to regulate the G2/M transition. CDK1 binds to cyclin B to regulate mitosis. CDK9 binds to cyclin T to regulate gene expression. Because of their role in the cell cycle, and hence cell proliferation, CDKs and cyclins are often mis-regulated in cancer cells. For example, CDKs and cyclins can be overexpressed, underexpressed or expressed at the wrong time in the cell cycle in cancer cells. Overexpression of cyclins is associated with some cancers. CDK inhibitors, by inhibiting CDK dependent cell cycle progression, can block the proliferation of cancer cells. Exemplary but non-limiting examples of CDKs targeted by a CDK inhibitor of the disclosure comprise CDK1, CDK2, CDK4, CDK6 and CDK9. Exemplary but non-limiting CDK inhibitors comprise Abemciclib (Verzenio), Palbociclib (Ibrance), Ribociclib (Kisqali) and analogs or derivatives thereof. Cyclin inhibitors, by inhibiting cyclin dependent CDK activation and CDK dependent cell cycle progression, can also block the proliferation of cancer cells. Exemplary but non-limiting examples of cyclins targeted by a cyclin inhibitor of the disclosure comprise cyclins D1, D2, D3, B, A, E, and T.

In some embodiments, the additional chemotherapeutic agent may comprise an mTOR inhibitor. Mechanistic target of rapamycin kinase (MTOR or mTOR) is a serine threonine kinase that belongs to the family of phosphatidylinositol-3 kinase (PI3K) related kinases. The mTOR pathway plays an important role in regulating cellular growth, metabolism, proliferation and apoptosis. For example, mTOR is downstream of PI3K and Protein kinase B (PKB, also known as AKT), a signaling pathway involved in regulating normal cellular processes such as cell cycle progression, growth, proliferation and survival. Aberrant activation of the PI3K/Akt/mTOR pathway is associated with many human cancers. Activation of this pathway in cancer cells occurs, for example, through the overexpression of genes or proteins in the pathway, or through the loss of function of inhibitors of the pathway. For example, loss of function of the PTEN tumor suppressor gene, which negatively regulates the PI3K/AKT, leads to upregulation of PI3K/AKT/mTOR pathway in cancer cells. mTOR functions through two distinct complexes, mTORC1 and mTORC2, which interact with each other and elements of other signaling pathways. Because of its role in cell proliferation, growth and survival, inhibiting the mTOR pathway can inhibit the proliferation and growth of cancer cells. Inhibitors of mTOR can inhibit the function of the mTOR protein, or act on other members of the mTOR signaling pathway to reduce the activity of the mTOR pathway. For example, mTOR inhibitors can inhibit the function of members of the mTORC1 or mTORC2 complexes, or inhibit the function of proteins upstream or downstream of mTOR in the mTOR signaling pathway. Exemplary, but non-limiting mTOR inhibitors comprise rapamycin, temsirolimus, everolimus, ridoforolimus and analogs or derivatives thereof. All inhibitors or mTOR are considered within the scope of the invention.

All possible methods of delivering the composition comprising pyrvinium pamoate and the composition comprising at least one other additional chemotherapeutic agent are considered within the scope of the invention. For example the composition comprising pyrvinium pamoate and the s at least one other chemotherapeutic agent can be administered sequentially. Alternatively, the composition comprising pyrvinium pamoate and the at least one other chemotherapeutic agent can be administered in an alternating series. Or, the composition comprising pyrvinium pamoate and the at least one other chemotherapeutic agent can be administered simultaneously. If delivered simultaneous the composition comprising pyrvinium pamoate and the at least one other chemotherapeutic agent can combined in a mixed composition, or delivered separately—e.g., one via injection and the other orally.

All possible combinations of routes of delivery of the composition comprising pyrvinium pamoate and the at least one additional chemotherapeutic agent are considered within the scope of the invention. For example, the composition comprising pyrvinium pamoate can administered orally and the at least one other chemotherapeutic agent can be administered parenterally. Alternatively, the composition comprising pyrvinium pamoate can administered parenterally and the at least one other chemotherapeutic agent can be administered orally. Or the composition comprising pyrvinium pamoate and at least one other chemotherapeutic agent can both be administered orally or parenterally. In any of these cases, the parenteral administration comprise can comprises an injection or an infusion. The injection can comprise a subcutaneous injection, an intraperitoneal injection, an intravenous injection or an intramuscular injection. The infusion can comprise an intravenous infusion.

Additional Cancer Treatments

In some embodiments of the methods of treating cancer of the disclosure, the administration of the composition comprising a therapeutically effective amount of pyrvinium pamoate, and optionally a pyrvinium pamoate combinational therapy comprises a cancer monotherapy.

In some embodiments of the methods of treating cancer of the disclosure, the treatment of cancer further comprises the administration of both the composition comprising a therapeutically effective amount of pyrvinium pamoate, optionally a pyrvinium pamoate combinational therapy, and one or more additional cancer treatments or therapeutic agents. Treatments of the rare cancers of the disclosure typically comprise surgical resection of the cancer. In some embodiments, especially those embodiments wherein the cancer is an early stage cancer that has not yet spread to surrounding tissues or metastasized throughout the body, treatment of the cancer may consist of complete surgical resection of the cancer. In some embodiments, the resection may comprise a partial removal of the cancer. Alternatively, or in addition, treatment of the cancer may further comprise chemotherapy, radiation therapy or a combination thereof. In some embodiments, treatment of a cancer of the disclosure may comprise neoadjuvant chemotherapy, i.e. chemotherapy that occurs before surgical intervention to remove the cancer. In some embodiments, in particular those embodiments wherein the cancer is a neuroendocrine cancer, treatment may comprise hormone therapy.

In some embodiments of the methods of treating cancer of the disclosure, the cancer treatment further comprises administering a third therapeutic agent or combination of therapeutic agents. In some embodiments, the third therapeutic agent or combination of therapeutic agents comprises a chemotherapeutic agent, a combination of chemotherapeutic agents, or a chemotherapeutic agent combined with an additional cancer therapy. In some embodiments, the one or more additional therapeutic agents comprises a Maytansinoid or an analog or derivative thereof. In some embodiments, the Maytansinoid comprises Maytansine, Maytansinol, or derivatives or analogs thereof. In some embodiments, the one or more additional therapeutic agents comprises a Calicheamicin, or a derivative or an analog thereof. In some embodiments, the one or more additional therapeutic agents comprises an Auristatin or a derivative or analog thereof. Exemplary but non-limiting auristatins comprise Monomethyl auristatin E, Monomethyl auristatin F, Dolastatin 10, Dolastatin 15, or analogs or derivatives thereof. In some embodiments, the one or more additional therapeutic agents comprises a Halichondrin and analogs or a derivative thereof. In some embodiments, the one or more additional therapeutic agents comprises a Hemiasterlin or an analog or a derivative thereof. In some embodiments, the one or more additional therapeutic agents comprises a Crytophycin or an analog or a derivative thereof. In some embodiments, the one or more additional therapeutic agents comprises a Spongistatin or an analog or a derivative thereof. In some embodiments, the one or more additional therapeutic agents comprises an Alkoyamine or an analog or a derivative thereof. In some embodiments, the one or more additional therapeutic agents comprises a Sesterterpenoid or an analog or a derivative thereof.

In some embodiments, the third therapeutic agent or combination of therapeutic agents other than pyrvinium pamoate, and optionally, a pyrvinium pamoate combination therapy, targets cellular pathways that are upregulated or critical in rapidly dividing cancer cells. Exemplary agents and pathways comprise cell cycle checkpoint inhibitors, antimitotic agents, pro-apoptotic agents, DNA damaging agents or inhibitors of the DNA damage response pathway. Exemplary but non-limiting chemotherapeutic agents which may, in some embodiments, be administered in combination with the composition comprising pyrvinium pamoate and, optionally, the composition comprising a second additional chemotherapeutic agent of the disclosure are shown in Table 2.

TABLE 2

| Chemotherapeutic Agents | | |
|---|---|---|
| generic name | brand name ® | other brand names ®/formulations |
| 5-fluorouracil | Adrucil | |
| Abemaciclib | Verzenio | |
| Abiraterone acetate | Zytiga | |
| Afatinib | Gilotrif | |
| Aldesleukin | Proleukin | |
| Alitretinoin | Panretin | |
| Altretamine | Hexalen | |
| Amifostine | Ethyol | |
| Anastrozole | Arimidex | |
| arsenic trioxide | Trisenox | |
| Asparaginase | Elspar | |
| Asparaginase Erwinia chrysanthemi | Erwinaze | |
| Axinitib | Inlyta | |
| Azacitidine | Vidaza | |
| BCG | TheraCys BCG, | TICE BCG, *Bacillus* Calmette-Guerin vaccine |
| Bendamustine hydrochloride | Treanda | |
| Bexarotene | Targretin | |
| Bicalutamide | Casodex | |
| Bilnostat | Beleodaq | |
| Bleomycin | Blenoxane | |
| Bortezomib | Velcade | |
| Bosutinib | Bosulif | |
| Buslfan | Buslfex | |
| Busulfan | Myleran | |
| Cabazitaxel | Jevtana | |
| Cabozantinib | Cometriq | |
| capecitabine | Xeloda | |
| carboplatin | Paraplatin | |
| Carfilzomib | Kyprolis | |
| Carmustine | BiCNU | |
| Carmustine | Gliadel Wafer | |
| Ceretinib | Zykadia | |
| Chlorambucil | Leukeran | |
| Cisplatin | Platinol | Platinol AQ |
| Cladribine | Leustatin | |
| Clofarabine | Clolar | |
| Cobemetinib | Cotellic | |
| Crizotinib | Xalkori | |

TABLE 2-continued

Chemotherapeutic Agents

| generic name | brand name ® | other brand names ®/formulations |
|---|---|---|
| Cyclophosphamide | Neosar | 4-hydroperoxycyclophosphamide (4-HC); Pergamid |
| Cytarabine | CytosarU | DepoCyt, Cytarabine lipid complex |
| Cytoxan | Cytoxan | Cyclophosphamide |
| Dabrafenib | Taflinar | |
| Dactinomycin | Cosmegen | |
| dasatinib | Sprycel | |
| Daunorubicin | Cerubidine | |
| Daunorubicin | DaunoXome | Daunorubicin lipid complex |
| Dacarbazine | DTIC | Imidazole Carboxamide |
| Decitabine | Dacogen | |
| Degarelix | Firmagon | |
| Denileukin diftitox | Ontak | |
| Dexamethasone | Decadron | Dexamethosone Intensol, Dexpak Taperpak |
| Docetaxel | Docefrez | |
| Doxorubicin | Adriamycin | Doxorubicin lipid complex, Doxil, Rubex |
| Ellence epirubicin | Ellence | |
| Eloxatin oxaliplatin | Eloxatin | |
| Enzalutamide | Xtandi | |
| Eribulin | Galaven | |
| Erlotinib | Tarceva | |
| Estramustine | Emcyt | |
| Etoposide | Etopophos | Toposar, Vepesid |
| Everolimus | Afinitor | Zortress, Afinitor Disperz |
| Exemestane | Aromasin | |
| Filgrastim | Neulasta | Pegfilgrastim, Neupogen |
| Fludarabine | Fludara | |
| Flutamide | Eulexin | |
| FUDR floxuridine | FUDR | |
| Fulvestrant | Faslodex | |
| Gefitinib | Iressa | |
| Gemcitabine | Gemzar | |
| Goserelin | Zoladex | |
| HDAC | High Dose Cytarabine | |
| Histrelin | Supprelin LA | Histrelin implant, Vantas |
| Hydroxyurea | Droxia | Hydrea |
| Iapatinib | Tykerb | |
| Ibrutinib | Imbruvica | |
| Idarubicin | Idamycin PFS | |
| idelalisib | Zydelig | |
| Ifosfamide | Ifex | |
| Imatinib Mesylate | Gleevec | |
| interferon alpha-2a | Intron A alfab | RoferonA alfaa |
| Irinotecan | Camptosar | |
| Ixabepilone | Ixempra | |
| Lapatinib | Tykerb | Tyverb, Lapatinib ditosylate |
| Lenalidomide | Revlimid | |
| Lenvatinib mesylate | Lenvima | |
| Lanreotide acetate | Somatuline Depot | |
| Letrozole | Femara | |
| Leucovorin | Wellcovorin IV | |
| Leuprolide | Eligard | Lupron, Lupron Depot, Lupron DepotPED |
| Lomustine | CeeNU | |
| Mechlorethamine | Mustargen | |
| Megestrol | Megace | |
| Melphalan | Alteran | |
| Mercaptopurine | Purinethol | |
| Mesna | Mesnex | |
| Methotrexate | Abitrexate | Folex, Mexate, Rheumatrex, Trexall |
| Mitomycin | Mutamycin | |
| Mitotane | Lysodren | |
| mitoxantrone | Novantrone | |
| Nelarabine | Arranon | |
| Nilandron nilutamide | Nilandron | |
| Octreotide | Sandostatin | Sandostatin LAR depot |
| Olaparib | Lynparza | |
| Omacetraxine | synribo | |
| Paclitaxel | Abraxane | Onxol, Taxol |
| Palbociclib | Ibrance | |
| Pamidronate | Aredia | |
| Panitumumab | Vectabix | |
| Panobinostat | Farydak | |
| Pazapanib | Votrient | |

TABLE 2-continued

Chemotherapeutic Agents

| generic name | brand name ® | other brand names ®/formulations |
|---|---|---|
| Pegaspargase | Oncaspar | |
| Peginterferon alpha-2b | Sylatron | |
| Pemetrexed | Alimta | |
| Pentostatin | Nipent | |
| Pomalidomide | Pomalyst | |
| Ponatinib | Iclusig | |
| Pralatrexate | Flolotyn | |
| Prednisone | Predisone intensol | Sterapred, Sterapred DS |
| Procarbazine | Matulane | |
| Raltitrexed | Tomudex | |
| Radium 223 dichloride | Xofigo | |
| Regorafenib | Stivarga | |
| Romidepsin | Istodax | |
| Ruxolitinib | Jakafi | |
| Sargramostim | Leukine | |
| Siltuximab | Sylvant | |
| Sonidegib | Odomzo | |
| Soragenib | Nexava | |
| Streptozocin | Zanosar | |
| Strontium 89 chloride | Metastron | |
| Sunitinib | Sutent | |
| Tamoxifen | Nolvadex | Soltamox |
| Temozolomide | Temodar | |
| Temsirolimus | Torisel | |
| Teniposide | Vumon | |
| Thalidomide | Thalomid | |
| Thioguanine | Tabloid | |
| Thiotepa | Tepadina | Thioplex |
| Topotecan | Hycamtin | |
| Toremifene | Fareston | |
| Trabectedin | Yondelis | |
| Trametinib | Mekinist | |
| Tretinoin | Sanoid | |
| Trifluridine and Tipiracil | Lonsurf | |
| Triptorelin | Trelstar | |
| Talrubicin intravesical | Valstar | |
| Vandetabib | Caprelsa | |
| vemurafenib | Zelboraf | |
| vinblastine | Velban | |
| Vincristine | Marqibo Kit | Vincristine lipid complex, Oncovin, Vincasar PFS, Vincrex |
| vinorelibine | Navelbine | |
| Vismodegib | Erivedge | |
| Vorinostat | Zolinza | |
| Ziv-aflibercept | Zaltrap | |
| Zoledronic acid | Zometra | Reclast |
| Alectinib | Alecensa | |
| Ixazomib | Ninlaro | |
| Nilotinib | Tasigna | |
| Osimertinib | Tagrisso | |
| Venetoclax | Venclexta | |
| Ribociclib | Kisqali | |
| Enasidenib | Idhifa | |
| Rucaparib | Rubraca | |
| Niraparib | Zejula | |
| Copanlisib | Aliqopa | |
| Neratinib | Nerlynx | |
| Brigatinib | Alunbrig | |
| Midostaurin | Rydapt | |
| Vindesine | Eldisine | Vindesine sulfate |
| Lometrexol | | |
| Satraplatin | | |
| Larotaxel | | |
| Rapamycin | Sirolimus | Rapamune |
| Temsirolimus | Torisel | |
| Ridaforolimus | Deforolimus | MK-8669 |

In some embodiments of the methods of treating cancer of the disclosure comprising administering a therapeutically effective amount of a composition comprising pyrvinium pamoate, and optionally, a composition comprising a second, additional chemotherapeutic agent, the treatment further comprises the administration of a small molecule targeted therapy. In some embodiments, the small molecule targeted therapy may comprise Alectinib (Alecensa), Ixazomib (Ninlaro), Nilotinib (Tasigna), Osimertinib (Tagrisso), Venetoclax (Venclexta), Ribociclib (Kisqali), Enasidenib (Idhifa), Rucaparib (Rubraca), Niraparib (Zejula), Copanlisib (Aliqopa), Neratinib (Nerlynx), Brigatinib (Alunbrig), Midostaurin (Rydapt) or a combination thereof.

In some embodiments of the methods of treating cancer of the disclosure comprising administering a therapeutically effective amount of a composition comprising pyrvinium pamoate, the treatment further comprises the administration of a combination chemotherapy. Exemplary but non-limiting examples of combination chemotherapies are disclosed in Table 3 below. The ordinarily skilled artisan will understand that there are variations known in the art of the combination chemotherapies disclosed in table 3. For example, combinations which substitute one steroid for another similar steroid may still be called by the same abbreviation.

TABLE 3

Combination Chemotherapies

| Name | Combination |
|---|---|
| 7 + 3 | 7 days of standard dose Cytarabine; 3 days of Daunorubicin, Doxorubicin, Idarubicin or Mitoxantrone |
| ABVD | Doxorubicin, Bleomycin, Vinblastine, Dacarbazine |
| AC | Doxorubicin, Cyclophosphamide |
| AD | Doxorubicin, Dacarbazine |
| ADE | Cytarabine, Daunorubicin, Etoposide |
| ADOC | Cisplatin, Doxorubicin, Vincristine, Cyclophosphamide |
| BEACOPP | Bleomycin, Etoposide, Doxorubicin, Cyclophosphamide, Vincristine, Procarbazine, Prednisone |
| BEP | Bleomycin, Etoposide, Cisplatin |
| CAF | Cyclophosphamide, Doxorubicin, 5-Fluorouracil (5-FU) |
| CAPIRI | Capecitabine, Irinotecan |
| CAPOX | Capecitabine, Oxaliplatin |
| CB | Cetuximab, Bevacizumab |
| CBI | Cetuximab, Bevacizumab, Irinotecan |
| CEF | Cyclophosphamide, Epirubicin, 5-FU |
| CEPP | Cyclophosphamide, Etoposide, Procarbazine, Prednisone |
| CFAR | Cyclophosphamide, Fludarabine, Alemtuzumab, Rituximab |
| CHOP | Cyclophosphamide, Doxorubicin, Vincristine, Prednisolone |
| CHOP + R (R-CHOP) | Cyclophosphamide, Doxorubicin, Vincristine, Prednisolone, Rituximab |
| CIM | Cisplatin, Ifosfamide, Mesna |
| CLAG | Cladribine, Cytarabine, |
| CLAG-M | Cladribine, Cytarabine, Mitoxantrone |
| CMC | Cladribine, Mitoxantrone, Cyclophosphamide |
| CMF | Cyclophosphamide, Methotrexate, 5-FU |
| COI | Capecitabine, Oxaliplatin, Irinotecan |
| CVD | Cisplatin, Vinblastine, Dacarbazine |
| CVP | Cyclophosphamide, Vincristine, Prednisone |
| DHAP | Cisplatin, Cytarabine, Dexamethasone |
| DVD | Doxorubicin, Vincristine, Dexamethasone |
| ECF | Epirubicin, Cisplatin, 5-FU |
| ECX | Epirubicin, Oxaliplatin, Capecitabine |
| EOF | Epirubicin, Oxaliplatin, 5-FU |
| EOX | Epirubicin, Oxaliplatin, Capecitabine |
| EP | Etoposide, Cisplatin |
| EPOCH | Etoposide, Prednisone, Vincristine, Cyclophosphamide, Doxorubicin |
| EPOCH + R | Etoposide, Prednisone, Vincristine, Cyclophosphamide, Doxorubicin, Rituximab |
| ESHAP | Etoposide, Methylprednisolone, Cisplatin, Cytarabine |
| FAMTX | Methotrexate, 5-FU, Doxorubicin |
| FC | Fludarabine, Cyclophosphamide |
| FCR | Fludarabine, Cyclophosphamide, Rituximab |
| FEC | 5-FU, Epirubicin, Cyclophosphamide |
| FLAG-IDA | Fludarabine, Cytarabine, Idarubicin |
| FLO | 5-FU, Leucovorin, Oxaliplatin |
| FLOX | 5-FU, Leucovorin, Oxaliplatin |
| FOLFIRI | Irinotecan, 5-FU, Leucovorin |
| FOLFOX | 5-FU, Leucovorin, Oxaliplatin |
| FOLFOXIRI | 5-FU, Leucovorin, Oxaliplatin, Irinotecan |
| GEMOX-B | Gemcitabine, Oxaliplatin, Bevacizumab |
| GVD | Gemcitabine, Vinorelbine, Doxorubicin |
| Hyper-CVAD | Cyclophosphamide, Doxorubicin, Vincristine, Dexamethasone, Mesna, Methotrexate, Leucovorin, Cytarabine |
| ICE | Ifosfamide, Carboplatin, Etoposide, Mesna |
| ICE-V | Ifosfamide, Carboplatin, Etoposide, Mesna, Vincristine |
| IFL | Irinotecan, 5-FU, Leucovorin |
| IROX | Irinotecan, Oxaliplatin |
| LV5FU2 | 5-FU, Leucovorin |
| LV5FU-P | Irinotecan, 5-FU, Leucovorin |
| MAID | Mesna, Doxorubicin, Ifosfamide, Dacarbazine |
| MFL | Methotrexate, 5-FU, Leucovorin |
| MINE | Mesna, Ifosfamide, Mitoxantrone, Etoposide |
| MOPP | Mechlorethamine, Vincristine, Prednisone, Procarbazine |
| MP | Melphalan, Prednisone |
| MPV | Methotrexate, Procarbazine, Vincristine |
| MVAC | Methotrexate, Vinblastine, Doxorubicin, Cisplatin |
| OFF | Oxaliplatin, 5-FU, Leucovorin |
| PAC | Cisplatin, Doxorubicin, Cyclophosphamide |
| PAD | Bortezomib, Dexamethasobne, Doxorubicin |
| PCR | Pentostatin, Cyclophosphamide, Rituximab |
| PCV | Procarbazine, Lomustine, Vincristine |
| R-MPV | Methotrexate, Procarbazine, Vincristine, Rituximab, Leucovorin |
| R-GemOx | Rituximab, Gemcitabine, Oxaliplatin |
| R-CVP | Cyclophosphamide, Vincristine, Prednisone, Rituximab |
| R-FCM | Rituximab, Cyclophosphamide, Fludarbine, Mitoxantrone |
| RICE | Ifosfamide, Carboplatin, Etoposide, Mesna, Rituximab |
| TAC | Docetaxel, Doxorubicin, Cyclophosphamide |
| TC | Docetaxel, Cyclophosphamide |
| TCH | Docetaxel, Carboplatin, Trastuzumab |
| TIP | Paclitaxel, Ifosfamide, Mesna, Cisplatin |
| TPC | Trastuzumab, Paclitaxel, Carboplatin |
| TPF | Docetaxel, Cisplatin, 5-FU |
| VAD | Vincristine, Doxorubicin, Dexamethosone |
| VIP | Etoposide, Vinblastine, Ifosfamide, Cisplatin, Mesna |
| VMP | Bortezomib, Melphalan, Prednisone |
| VMPT | Bortezomib, Melphalan, Prednisone, Thalidomide |
| XELIRI | Capecitabine, Irinotecan |
| XELOX | Capecitabine, Oxaliplatin |

In some embodiments of the methods of the disclosure, the methods further comprise administering a combination chemotherapy. In some embodiments, the combination chemotherapy comprises a 7+3 combination chemotherapy. Exemplary cancers treated by a 7+3 combination chemotherapy include but are not limited to acute myelogenous leukemia. In some embodiments, the combination chemotherapy comprises an ABVD combination chemotherapy. Exemplary cancers treated by an ABVD combination chemotherapy include but are not limited to Hodgkin lymphoma. In some embodiments, the combination chemotherapy comprises an AC or CMF combination chemotherapy. Exemplary cancers treated by an AC or CMF combination chemotherapy include but are not limited to breast cancers. In some embodiments, the combination chemotherapy comprises an AD combination chemotherapy. Exemplary cancers treated by an AD combination chemotherapy include but are not limited to sarcomas. In some embodiments, the combination chemotherapy comprises an ADE combination chemotherapy. Exemplary cancers treated by an ADE combination chemotherapy include but are not limited to acute myelogenous leukemias. In some embodiments, the combination chemotherapy comprises an ADOC combination chemotherapy. Exemplary cancers treated by an ADOC combination chemotherapy include but are not limited to thymoma. In some embodiments, the combination chemotherapy comprises a BEACOPP combination chemotherapy. Exemplary cancers treated by a BEACOPP combination chemotherapy include but are not limited to Hodgkin lymphomas. In some embodiments, the combination chemotherapy comprises a BEP combination chemotherapy. Exemplary cancers treated by a BEP combination chemotherapy include but are not limited to testicular cancers. In some embodiments, the combination chemotherapy comprises a CAF or CEF combination chemotherapy. Exemplary cancers treated by a CAF or CEF combination chemotherapy include but are not limited to breast cancers. In some embodiments, the combination chemotherapy comprises a CAPIRI, CAPDX, CB, CBI or COI combination chemotherapy. Exemplary cancers treated by a CAPIRI, CAPDX, CB, CBI or COI combination chemotherapy include but are not limited to colorectal cancers. In some embodiments, the combination chemotherapy comprises a CEPP, CHOP or R-CHOP combination chemotherapy. Exemplary cancers treated by a CEPP, CHOP or R-CHOP combination chemotherapy include but are not limited to non-Hodgkin lymphomas. In some embodiments, the combination chemotherapy comprises a CFAR or CMC combination chemotherapy. Exemplary cancers treated by a CFAR or CMC combination chemotherapy include but are not limited to chronic lymphocytic leukemias. In some embodiments, the combination chemotherapy comprises a CIM combination chemotherapy. Exemplary cancers treated by a CIM combination chemotherapy include but are not limited to uterine sarcomas. In some embodiments, the combination chemotherapy comprises a CLAG or a CLAG-M combination chemotherapy. Exemplary cancers treated by a CLAG or a CLAG-M combination chemotherapy include but are not limited to acute myelogenous leukemias. In some embodiments, the combination chemotherapy comprises a CVD combination chemotherapy. Exemplary cancers treated by a CVD combination chemotherapy include but are not limited to melanomas. In some embodiments, the combination chemotherapy comprises a CVP combination chemotherapy. Exemplary cancers treated by a CVP combination chemotherapy include but are not limited to chronic lymphocytic leukemias and non-Hodgkin lymphomas. In some embodiments, the combination chemotherapy comprises a DHAP combination chemotherapy. Exemplary cancers treated by a DHAP combination chemotherapy include but are not limited to lymphomas. In some embodiments, the combination chemotherapy comprises a DVD combination chemotherapy. Exemplary cancers treated by a DVD combination chemotherapy include but are not limited to multiple myelomas. In some embodiments, the combination chemotherapy comprises an ECF, ECX, EOF or EOX combination chemotherapy. Exemplary cancers treated by an ECF, ECX, EOF or EOX combination chemotherapy include but are not limited to esophageal cancers and gastric cancers. In some embodiments, the combination chemotherapy comprises an EP combination chemotherapy. Exemplary cancers treated by an EP combination chemotherapy include but are not limited to testicular cancers and thymomas. In some embodiments, the combination chemotherapy comprises an EPOCH, EPOCH+R or ESHAP combination chemotherapy. Exemplary cancers treated by an EPOCH, EPOCH+R or ESHAP combination chemotherapy include but are not limited to non-Hodgkin lymphomas. In some embodiments, the combination chemotherapy comprises a FAMTX combination chemotherapy. Exemplary cancers treated by a FAMTX combination chemotherapy include but are not limited to gastric cancers. In some embodiments, the combination chemotherapy comprises a FC or FCR combination chemotherapy. Exemplary cancers treated by a FC or FCR combination chemotherapy include but are not limited to chronic lymphocytic leukemias. In some embodiments, the combination chemotherapy comprises a FEC combination chemotherapy. Exemplary cancers treated by a FEC combination chemotherapy include but are not limited to breast cancers. In some embodiments, the combination chemotherapy comprises a FLAG-IDA combination chemotherapy. Exemplary cancers treated by a FLAF-IDA combination chemotherapy include but are not limited to acute myelogenous leukemias. In some embodiments, the combination chemotherapy comprises a FLO combination chemotherapy. Exemplary cancers treated by a FLO combination chemotherapy include but are not limited to colorectal cancers and gastric cancers. In some embodiments, the combination chemotherapy comprises a FLOX, FOLFIRI, FOLFOX or FOLFOXIRI combination chemotherapy. Exemplary cancers treated by a FLOX, FOLFIRI, FOLFOX or FOLFOXIRI combination chemotherapy include but are not limited to colorectal cancers. In some embodiments, the combination chemotherapy comprises a GEMOX-B combination chemotherapy. Exemplary cancers treated by a GEMOX-B combination chemotherapy include but are not limited to hepatocellular cancers. In some embodiments, the combination chemotherapy comprises a GVD combination chemotherapy. Exemplary cancers treated by a GVD combination chemotherapy include but are not limited to Hodgkin lymphomas. In some embodiments, the combination chemotherapy comprises a Hyper-CVAD combination chemotherapy. Exemplary cancers treated by a hyper-CVAD combination chemotherapy include but are not limited to acute lymphocytic leukemias. In some embodiments, the combination chemotherapy comprises an ICE combination chemotherapy. Exemplary cancers treated by an ICE combination chemotherapy include but are not limited to non-Hodgkin lymphomas. In some embodiments, the combination chemotherapy comprises an ICE-V combination chemotherapy. Exemplary cancers treated by an ICE-V combination chemotherapy include but are not limited to small cell lung cancers. In some embodiments, the combination chemotherapy comprises an IFL, IROX or LV5FU2 combination chemotherapy. Exemplary cancers treated by an IFL, IROX or LV5FU2 combination chemotherapy include but are not limited to colorectal cancers. In some embodiments, the combination chemotherapy comprises an LV5FU-P combination chemotherapy. Exemplary cancers treated by an LV5FU-P combination chemotherapy include but are not limited to biliary cancers. In some embodiments, the combination chemotherapy comprises a MAID combination chemotherapy. Exemplary cancers treated by a MAID combination chemotherapy include but are not limited to sarcomas. In some embodiments, the combination chemotherapy comprises a MFL combination chemotherapy. Exemplary cancers treated by a MFL combination chemotherapy include but are not limited to breast cancers. In some embodiments, the combination chemotherapy comprises a MINE combination chemotherapy. Exemplary cancers treated by a MINE combination chemotherapy include but are not limited to lymphomas. In some embodiments, the combination chemotherapy comprises a MOPP combination chemotherapy. Exemplary cancers treated by a MOPP combination chemotherapy include but are not limited to Hodgkin lymphomas. In some embodiments, the combination chemotherapy comprises a MP combination chemotherapy. Exemplary cancers treated by a MP combination chemotherapy include but are not limited to multiple myelomas. In some embodiments, the combination chemotherapy comprises a MVP combination chemotherapy. Exemplary cancers treated by a MVP combination chemotherapy include but are not limited to lung cancers, mesotheliomas and breast cancers. In some embodiments, the combination chemotherapy comprises a MVAC combination chemotherapy. Exemplary cancers treated by a MVAC combination chemotherapy include but are not limited to bladder cancers. In some embodiments, the combination chemotherapy comprises an OFF combination chemotherapy. Exemplary cancers treated by an OFF combination chemotherapy include but are not limited to pancreatic cancers. In some embodiments, the combination chemotherapy comprises a PAC combination chemotherapy. Exemplary cancers treated by a PAC combination chemotherapy include but are not limited to lymphomas. In some embodiments, the combination chemotherapy comprises a PAD combination chemotherapy. Exemplary cancers treated by a PAD combination chemotherapy include but are not limited to multiple myelomas. In some embodiments, the combination chemotherapy comprises a PCR combination chemotherapy. Exemplary cancers treated by a PCR combination chemotherapy include but are not limited to chronic lymphocytic leukemias. In some embodiments, the combination chemotherapy comprises a PCV combination chemotherapy. Exemplary cancers treated by a PCV combination chemotherapy include but are not limited to brain cancers. In some embodiments, the combination chemotherapy comprises an R-MPV combination chemotherapy. Exemplary cancers treated by an R-MPV combination chemotherapy include but are not limited to central nervous system lymphomas. In some embodiments, the combination chemotherapy comprises an R-GemOx, R-CVP, R-FCM or RICE combination chemotherapy. Exemplary cancers treated by an R-GemOx, R-CVP, R-FCM or RICE combination chemotherapy include but are not limited to non-Hodgkin lymphomas. In some embodiments, the combination chemotherapy comprises a TAC, TC, TCH or TPC combination chemotherapy. Exemplary cancers treated by a TAC, TC, TCH or TPC combination chemotherapy include but are not limited to breast cancers. In some embodiments, the combination chemotherapy comprises a TIP or VIP combination chemotherapy. Exemplary cancers treated by a TIP or VIP combination chemotherapy include but are not limited to testicular cancers. In some embodiments, the combination chemotherapy comprises a TPF combination chemotherapy. Exemplary cancers treated by a TPF combination chemotherapy include but are not limited to head and neck cancers. In some embodiments, the combination chemotherapy comprises a VAD combination chemotherapy. Exemplary cancers treated by a VAD combination chemotherapy include but are not limited to multiple myelomas. In some embodiments, the combination chemotherapy comprises a VMP or VMPT combination chemotherapy. Exemplary cancers treated by a VMP or VMPT combination chemotherapy include but are not limited to multiple myelomas. In some embodiments, the combination chemotherapy comprises a XELIRI or XELOX combination chemotherapy. Exemplary cancers treated by a XELIRI or XELOX combination chemotherapy include but are not limited to colorectal cancers.

Therapeutic or chemotherapeutic agents of the disclosure (including a first and/or one or more second agents) may be administered by any appropriate route including, but not limited to, enteral routes, and parenteral routes, e.g., oral routes, intravenous routes, intramuscular routes, and direct absorption through mucous membrane tissues. The therapeutic agents can be administered by the same route or by different routes.

Therapeutic or chemotherapeutic agents of the disclosure (including a first and/or one or more second agents) may be administered simultaneously with the composition comprising pyrvinium pamoate. In some embodiments, the additional therapeutic agent and the composition comprising pyrvinium pamoate are in the same composition. For example, the additional therapeutic agent and pyrvinium pamoate are formulated in the same nanoparticle. Alternatively, or in addition, the additional therapeutic agent or the composition comprising pyrvinium pamoate is formulated in a nanoparticle. Alternatively, or in addition, the additional therapeutic agent and the composition comprising pyrvinium pamoate is formulated in different nanoparticles in the same composition.

In some embodiments, the additional therapeutic agent and the composition comprising pyrvinium pamoate are in the different compositions which are administered simultaneously. This administration can be by any route of administration. For example, the composition comprising pyrvinium pamoate and the additional therapeutic agent are both administered orally. Alternatively, the composition comprising pyrvinium pamoate is administered orally and the additional therapeutic agent is administered intravenously. Alternatively, the composition comprising pyrvinium pamoate is administered orally and the additional therapeutic agent is a combination therapy that is administered orally and intravenously.

Therapeutic or chemotherapeutic agents of the disclosure (including a first and/or one or more second agents) may be administered sequentially with the composition comprising pyrvinium pamoate. As used herein, the term "sequential administration" refers to administration in a series of ordered steps. For example, the composition comprising pyrvinium pamoate is administered first, and the additional therapeutic agent is administered second. Alternatively, the composition comprising pyrvinium pamoate is administered second, and the additional therapeutic agent is administered first. In some embodiments, the sequential administration is repeated, for example in a repeating series. Sequential administration can be separated by any length of time, for example 1 hour, 2 hours, 3 hours, 6 hours, 12 hours, 1 day, 2 days, 3 days, 1, week or 1 month.

Administration of the additional therapeutic or chemotherapeutic agent(s) can be in temporal proximity. Sequential administration of the additional therapeutic or chemotherapeutic agent(s) can be in temporal proximity. As used herein, the term "temporal proximity" refers to administrations that occur close together in time. For example, administrations separated by less than a minute, less than 5 minutes, less than 15 minutes, less than 30 minutes, less than 1 hour, less than 3 hours, less than 6 hours, less than 8 hours, less than 12 hours, less than 1 day, less than 2 days, less than 3 days or less than 1 week occur in temporal proximity.

The methods of, or compounds or medicaments for use in combination with the composition comprising pyrvinium pamoate and, optionally, the composition comprising at least one additional chemotherapeutic agent may result in a synergistic effect, wherein the effect of a combination of therapeutic agents (e.g. pyrvinium pamoate or a pharmaceutically acceptable salt thereof, and one or more second anti-cancer agents) is greater than the sum of the effects resulting from administration of any of the therapeutic agents as single agents. A synergistic effect may also be an effect that cannot be achieved by administration of any of the therapeutic agents as single agents. The synergistic effect may include, but is not limited to, an effect of treating cancer, e.g., by reducing tumor size, reducing the number or frequency of malignant cells in a subject or a sample obtained from a subject, inhibiting tumor growth, inhibiting growth, survival, or proliferation of malignant cells, or increasing survival of the subject. The synergistic effect may also include reducing cancer cell viability, inducing cancer cell death, and inhibiting or delaying cancer cell growth.

Methods of measuring synergy are well known in the art. For example, synergy can be measured using the Chou-Talalay method described in Chou and Talalay (Cancer Res. 2010 Jan. 15; 70(2):440-6. doi: 10.1158/0008-5472.CAN-09-1947. Epub 2010 Jan. 12), the contents of which are herein incorporated by reference in their entirety. The Chou-Talalay method provides an objective, quantitative measure of synergy between combinations of two or more agents. In brief, the Chou-Talalay method measures the effect of a combination of agents on cells, for example on cell viability, at different concentrations of the combination of agents. The different concentrations are preferably at a constant ratio. This data is used to generate a combination index (CI) plot and determine CI values for each of the different concentrations of the combination of agents. When the effects of two agents are additive, the CI is equal to 1. When the effects of two agents are synergistic, the CI is less than 1, preferably less than 0.9. When the effects of two agents are antagonistic, the CI is greater than 1.

In some embodiments, the CI of pyrvinium pamoate and an additional cancer therapy, e.g. an additional therapeutic agent or chemotherapeutic agent, is measured in vitro in a cancer cell line isolated or derived from a rare cancer.

A combination of pyrvinium pamoate and an additional cancer therapy at a particular concentration is synergistic if the CI is less than 0.9. A combination of pyrvinium pamoate and an additional cancer therapy at a particular concentration is strongly synergistic if the CI is less than 0.5, less than 0.4, less than less than 0.3, less than 0.2 or less than 0.1.

A combination of pyrvinium pamoate and an additional cancer therapy is synergistic for an indicated cancer if at least 3 different concentrations of the combination of pyrvinium pamoate and the additional cancer therapy have a CI of less than 0.9 when assayed in vitro in a cancer cell line isolated or derived from the indicated cancer.

A combination of pyrvinium pamoate and an additional cancer therapy is synergistic for an indicated cancer if at least 3 different concentrations of the combination of pyrvinium pamoate and the additional cancer therapy have a CI of less than 0.9 when assayed in vitro in at least one cancer cell line isolated or derived from the indicated cancer.

A combination of pyrvinium pamoate and an additional cancer therapy is strongly synergistic for an indicated cancer if at least 3 different concentrations of the combination of pyrvinium pamoate and the additional cancer therapy have a CI of less than 0.9 when assayed in vitro in more than one cancer cell line isolated or derived from the indicated cancer.

When two agents act synergistically in combination, the therapeutically effective dose of each agent in the combination is typically less than the effective dose of either agent acting as monotherapy. Methods of treatment comprising a synergistic combination of two agents, for example a synergistic combination of pyrvinium pamoate and an additional cancer therapy, therefore typically use lower dosages of one or both agents in the synergistic combination. These lower doses reduce toxicity and harmful side effects. Thus, synergistic combinations of pyrvinium pamoate and an additional cancer therapy provide superior safety and efficacy when compared to monotherapies, or combinations of therapies that do not act synergistically.

In some embodiments, a synergistic amount of the composition comprising pyrvinium pamoate and the one or more additional therapeutic agents is a specific concentration of the composition comprising pyrvinium pamoate and the one or more additional therapeutic agents. In some embodiments, a synergistic amount of the composition comprising pyrvinium pamoate and the one or more additional therapeutic agents is a specific ratio of the composition comprising pyrvinium pamoate to the one or more additional therapeutic agents. Methods for determining synergistic concentrations and ratios of the agents in a synergistic combination will be readily apparent to one of ordinary skill in the art.

The synergistic effect of the composition comprising pyrvinium pamoate and the one or more additional therapeutic agents may include, but is not limited to an effect of treating cancer, e.g., by reducing tumor size, reducing the number or frequency of malignant cells in a subject or a sample obtained from a subject, inhibiting tumor growth, inhibiting growth, survival, or proliferation of malignant cells, or increasing survival of the subject. The synergistic effect may also include reducing cancer cell viability, inducing cancer cell death, and inhibiting or delaying cancer cell growth.

In some embodiments of the methods of the disclosure, the effect of pyrvinium pamoate or a pharmaceutically acceptable salt thereof, and optionally at least one additional chemotherapeutic agent and the third or more additional therapeutic agents may be additive. As used herein, "additive" refers to an effect on a cancer of a subject that is equal to, and not greater than sum of the effects of, for example, pyrvinium pamoate and an additional therapeutic agent which were each administered to a subject alone. The additive effect may include, but is not limited to an effect of treating cancer, e.g., by reducing tumor size, reducing the number or frequency of malignant cells in a subject or a sample obtained from a subject, inhibiting tumor growth, inhibiting growth, survival, or proliferation of malignant cells, or increasing survival of the subject. The additive effect may also include reducing cancer cell viability, inducing cancer cell death, and inhibiting or delaying cancer cell growth.

In some embodiments, "combination therapy" or "combinational therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be affected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects of the invention "combination therapy" or "combinational therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In further aspects, a composition of the disclosure, or a pharmaceutically acceptable salt, solvate, analog or derivative thereof or nanoparticle formulation thereof may be administered in combination with radiation therapy. Radiation therapy can also be administered in combination with a composition of the disclosure and another chemotherapeutic agent described herein as part of a multiple agent therapy. In some embodiments, the composition comprising pyrvinium pamoate may act as a radio-sensitizer in combination with radiation therapy. The composition comprising pyrvinium pamoate may be administered prior to radiation treatment, concurrent with radiation treatment, or following radiation treatment.

In some embodiments of the methods of the treating cancer of the disclosure, in addition to administering a therapeutically effective amount of the composition comprising pyrvinium pamoate, and, optionally, a second chemotherapeutic agent or combination of therapeutic agents, the treatment may further comprise an immunotherapy. In some embodiments, the immunotherapy comprises an adoptive cell therapy. In some embodiments, the adoptive cell therapy comprises a chimeric antigen receptor, or CAR-T therapy. The adoptive cells may be autologous or allogeneic. In some embodiments, the immunotherapy comprises an immune checkpoint modulator. In some embodiments, the immune checkpoint modulator comprises an antibody that binds to a component of or otherwise affects the cell cycle checkpoint pathway. In some embodiments, the immune checkpoint modulator modulates a T cell response to cancer. In some embodiments, the immune checkpoint modulator comprises a PD-1 or PD-L1 checkpoint inhibitor. In some embodiments, the immune checkpoint modulator comprises a CLTA-4 checkpoint inhibitor. Exemplary but non-limiting immunotherapies comprise administering to the subject a therapeutically effective amount of a therapeutic antibody or antibody-drug conjugate. Exemplary, but non-limiting therapeutic antibodies and antibody-drug conjugates which may, in some embodiments, be administered in combination with the composition comprising pyrvinium pamoate and, optionally, the composition comprising at least one additional chemotherapeutic agent of the disclosure are listed in Table 4.

TABLE 4

| Therapeutic Antibodies | |
|---|---|
| generic name | brand name ® |
| Ado-trastuzumab Emtansine | Kadcycla |
| Alemtuzumab | Campath |
| Atezolizumab | Tecentriq |
| Avelumab | Bavencio |
| Bevacizumab | Avastin |
| Blinatumomab | Blincyto |
| Brentuximab Vedotin | Adcetris |
| Catumaxumab | Proxinium |
| Cetuximab | Erbitux |
| Daratumumab | Darzalex |
| Denosumab | Xgeva |
| Dinutuximab | Unituxin |
| Durvalumab | Imfinzi |
| Elotuzumab | Empliciti |
| Gemtuzumab ozogamicin | Mylotarg |
| Ibritumumab Tiuxetan | Zevalin |
| Ipilimumab | Yervoy |
| Inotuzumab ozogamicin | Besponsa |
| Mogamulizumab | Poteligeo |
| Necitumumab | Portrazza |
| Nivolumab | Opdivo |
| Obinutuzumab | Gazyva |
| Ocrelizumab | Ocrevus |
| Ofatumab | Arzerra |
| Olaratumab | Lartruvo |
| Panitumumab | Vectibix |
| Pembrolizumab | Keytruda |
| Pertuzumab | Perjeta |
| Ramucirumab | Cyramza |
| Rituximab | Rituxan |
| Tositumomab | Bexxar |
| Trastuzumab | Herceptin |
| Zevalin | Ibritumomab tiuxetan |

Exemplary PD-L1 antibodies include, but are not limited to Atezolizumab, Avelumab and Durvalumab. Exemplary PD-1 antibodies include, but are not limited to Pembrolizumab, Nivolumab and Cemiplimab. Exemplary CTLA-4 antibodies include, but are not limited to Ipilimumab.

As used herein, the "term cell cycle checkpoint" refers to one of several points in the eukaryotic cell cycle at which progression of the cell to the next stage of the cell cycle can be halted under unfavorable conditions. Exemplary, but non-limiting unfavorable conditions comprise improper mitotic spindle formation, excessive levels of DNA damage, and problems with DNA replication.

A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1 (mi), PN1a, PN1b, PN1c, pN2, pN2a, pN2b, pN3, pN3a, pN3b, or pN3c. Alternatively, or in addition, a cancer can be staged according to the TNM staging system, which divides most types of cancers into 4 stages. Stage 1 usually means that a cancer is relatively small and contained within the organ of origin. Stage 2 cancers have usually not started to spread into surround tissues, but that the tumor is larger than stage 1. In some embodiments, stage 2 means that the cancer has spread into the lymph nodes close to the tumor. Stage 3 cancers are usually larger, and have started to spread into surrounding tissues and lymph nodes. Stage 4, or metastatic cancers, are typically cancers that have spread from the point of origin to other organ(s) in the body.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, polymorph, solvate, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, polymorph or solvate thereof, is more effective than combination therapy in inducing a desired biological effect.

As used herein, "treating" or "treat" describes the management and care of a subject for the purpose of combating a disease, condition, or disorder and includes the administration of a composition of the disclosure, or a pharmaceutically acceptable salt, prodrug, metabolite, polymorph or solvate thereof, to alleviate the symptoms or complications of cancer or to eliminate the cancer.

As used herein, the term "alleviate" is meant to describe a process by which the severity of a sign or symptom of cancer is decreased. Importantly, a sign or symptom can be alleviated without being eliminated. In a preferred embodiment, the administration of pharmaceutical compositions of the disclosure leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

As used herein, the term "aggressive" indicates a cancer that can grow, form or spread quickly. Cancers termed aggressive may be susceptible to treatment, or they may resist treatment. An aggressive cancer can comprise any sort of cancer. Alternatively, or in addition, the term "aggressive" may describe a cancer that requires a more severe or intense than the usual form of treatment for that cancer.

As used herein, the term "refractory" describes a cancer that does not respond to an attempted form of treatment. Refractory cancers can also be termed resistant cancers.

In another aspect of the disclosure, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. Cancers may form in places where it does not cause any symptoms until the cancer has grown quite large.

Cancer may also cause symptoms such as fever, fatigue, or weight loss. This may be because cancer cells use up much of the body's energy supply or release substances that change the body's metabolism. Or the cancer may cause the immune system to react in ways that produce these symptoms. While the signs and symptoms listed above are the more common ones seen with cancer, there are many others that are less common and are not listed here. However, all art-recognized signs and symptoms of cancer are contemplated and encompassed by the disclosure.

Treating cancer may result in a reduction in size of a tumor. A reduction in size of a tumor may also be referred to as "tumor regression". Preferably, after treatment according to the methods of the disclosure, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer may result in a reduction in tumor volume. Preferably, after treatment according to the methods of the disclosure, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer may result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in a decrease in number of metastatic lesions in other tissues or organs distant from the primary tumor site. Preferably, after treatment according to the methods of the disclosure, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, polymorph, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, polymorph, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating cancer can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating cancer can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating cancer can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating cancer can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Pharmaceutical Compositions

A "pharmaceutical composition" is a formulation comprising pyrvinium pamoate in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), intraperitoneal (into the body cavity) and transmucosal administration. Solutions or suspensions used for parenteral, intradermal, intraperitoneal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pyrvinium pamoate can be administered to a subject in many of the well-known methods currently used for therapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent a cancer in a subject, or to exhibit a detectable therapeutic or inhibitory effect on said cancer in a subject. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. In some embodiments, a standard xenograft or patient derived xenograft mouse model can be used to determine the effectiveness of pyrvinium pamoate on a cancer of the disclosure. Such information can then be used to determine useful doses and routes for administration in humans. Therapeutic/prophylactic efficacy and toxicity may be determined by standard pharmaceutical procedures in cell cultures or experimental animals, e.g., the maximum tolerated dose and no observable adverse effect dose. Pharmaceutical compositions that exhibit large therapeutic windows are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing pyrvinium pamoate may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required nanoparticle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by intramuscular, intraperitoneal, subcutaneous, transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages may vary depending on the age and size of the subject and the type and severity of the cancer. In some embodiments, the dosage of pyrvinium pamoate comprises at least 5 mg per kg of body weight in a single dose. In some embodiments, the dosage of pyrvinium pamoate comprises at least 50 mg per kg of body weight in a single dose. In some embodiments, the dosage of pyrvinium pamoate comprises 350 mg or less in a single dose, regardless of body weight. In some embodiments, the dosage of pyrvinium pamoate comprises 0.1-1 mg per kg of body weight administered 3 times per week. In some embodiments, the dosage of pyrvinium pamoate comprises 0.1-1 mg per kg of body weight per day. In some embodiments, the dosage of pyrvinium pamoate comprises 0.1-25 mg per kg of body weight administered 3 times per week. In some embodiments, the dosage of pyrvinium pamoate comprises 0.1-25 mg per kg of body weight per day. In some embodiments, the dosage of pyrvinium pamoate comprises 0.5 mg per kg of body weight per day. In some embodiments, the dosage of pyrvinium pamoate comprises 10 mg per kg of body weight per day. In some embodiments, the dosage of pyrvinium pamoate comprises a dosage of 25 mg per kg of body weight. In some embodiments, dosage of 25 mg per kg of body weight is administered daily. In some embodiments, dosage of 25 mg per kg of body weight is administered three times per week.

In some embodiments, the composition comprising pyrvinium pamoate is administered parenterally. In some embodiments, the parenteral administration comprises intramuscular, intraperitoneal, subcutaneous or intravenous administration. In some embodiments, the administration occurs once a month. In some embodiments, the administration occurs every two weeks. In some embodiments, the administration occurs once a week. In some embodiments, the administration occurs once a day. In some embodiments, the administration occurs twice a day. In some embodiments, the administration occurs three times a day. In some embodiments, the administration occurs four or more times a day. In some embodiments, the subject is administered a composition comprising a therapeutically effective amount of the composition comprising pyrvinium pamoate, for at least a week, at least a month, at least 2 months, at least 3 months, at least 4 months, at least 5 months, at least 6 months, at least 1 year, at least 2 years, at least 3 years or until the cancer is alleviated.

In some embodiments, the composition comprising pyrvinium pamoate is administered orally. In some embodiments, the oral administration comprises administration with food. In some embodiments, the administration occurs once a month. In some embodiments, the administration occurs every two weeks. In some embodiments, the administration occurs once a week. In some embodiments, the administration occurs once a day. In some embodiments, the administration occurs twice a day. In some embodiments, the administration occurs three times a day. In some embodiments, the administration occurs four or more times a day. In some embodiments, the subject is administered a composition comprising a therapeutically effective amount of the composition comprising pyrvinium pamoate, for at least a week, at least a month, at least 2 months, at least 3 months, at least 4 months, at least 5 months, at least 6 months, at least 1 year, at least 2 years, at least 3 years or until the cancer is alleviated.

In some embodiments, the composition comprising pyrvinium pamoate is administered daily, every day, without a holiday. In some embodiments, the composition comprising pyrvinium pamoate is administered with a holiday. In some embodiments, this holiday is once a week. In some embodiments, this holiday is twice a week. In some embodiments, this holiday is once every other week. In some embodiments, this holiday is once a month. In some embodiments, this holiday is determined by the effectiveness of the pyrvinium pamoate in alleviating a sign or a symptom of the cancer, and/or how well the subject with the cancer tolerates the administration of the composition comprising pyrvinium pamoate.

In some embodiments, the composition comprising pyrvinium pamoate and, optionally, the composition comprising at least one additional chemotherapeutic agent is administered simultaneously with one or more additional cancer therapies. In some embodiments, the composition comprising pyrvinium pamoate is administered before an additional cancer therapy. In some embodiments, the composition comprising pyrvinium pamoate and, optionally, the composition comprising at least one additional chemotherapeutic agent is administered after an additional cancer therapy. In some embodiments, the composition comprising pyrvinium pamoate and, optionally, the composition comprising at least one additional chemotherapeutic agent and the additional cancer therapy are administered in alternation. In some embodiments, this additional cancer therapy comprises an additional chemotherapy.

An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

Pyrvinium is capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as etha- nolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

The pyrvinium, or pharmaceutically acceptable salts or solvates thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In some embodiment, the composition comprising pyrvinium pamoate is administered orally. In some embodiments, the oral administration occurs with food. In some embodiments, the composition comprising pyrvinium pamoate is administered parenterally. In some embodiments, the parenteral administration comprises intramuscular, intraperitoneal, subcutaneous or intravenous administration. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In some embodiments, pyrvinium, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

Kits and Articles of Manufacture

The invention provides kits comprising any one or more of the compositions described herein, including but not limited to compositions comprising pyrvinium pamoate and compositions comprising pyrvinium pamoate and one or more additional therapeutic or chemotherapeutic agents. The kits are for use in the treatment of cancer.

In some embodiments of the kits of the disclosure, the kit comprises a therapeutically effective amount of the composition comprising pyrvinium pamoate and instructions for use in the treatment of cancer. In some embodiments, the kit further comprises at least one additional cancer therapeutic agent. The composition comprising pyrvinium pamoate and the additional cancer therapeutic agent are the same composition, e.g. a single pill or tablet formulated for oral administration, or a single liquid composition in a vial formulated for intravenous administration. Alternatively, the composition comprising pyrvinium pamoate and the additional cancer therapeutic agent are the different compositions both included in the kit.

In some embodiments of the kits of the disclosure, the therapeutically effective amount of the composition comprising pyrvinium pamoate comprises a synergistically effective amount of the composition comprising pyrvinium pamoate. In some embodiments, the composition comprising pyrvinium pamoate and the at least one additional cancer therapeutic agent exhibit synergy. Synergy between the composition comprising pyrvinium pamoate and the at least one additional cancer therapeutic agent can be measured using the methods described herein.

In some embodiments of the kits of the disclosure, the at least one additional cancer therapeutic agent comprises a second chemotherapeutic agent, a combination chemotherapy, a therapeutic antibody, a chimeric antigen receptor T cell (CAR-T) therapy or a combination thereof. In some embodiments, the at least one additional cancer therapeutic agent comprises Paclitaxel, Docetaxel, Vincristine, Vinorelbine, Cisplatin, Carboplatin, Oxaliplatin, Irinotecan, Etoposide, 5-FU, Doxorubicin, Temozolomide, Dacarbazine, Cyclophosphamide, Ifosfamide, Abemaciclib, Gemcitabine, Erlotinib, Imatinib or Sorafenib.

In some embodiments of the kits of the disclosure, the composition comprising pyrvinium pamoate comprises pyrvinium pamoate formulated in a nanoparticle. In some embodiments, both the pyrvinium pamoate and the at least one additional cancer therapeutic agent are formulated in a nanoparticle. In some embodiments, the nanoparticle is the same nanoparticle. In some embodiments, the nanoparticle comprises a PLGA polymer and an HA targeting agent.

Articles of manufacture include, but are not limited to, instructions for use of the kit in treating cancers, for example rare cancer indications of the disclosure, and vials.

ENUMERATED EMBODIMENTS

The invention may be defined by reference to the following enumerated, illustrative embodiments:

1. A method of treating a cancer in a subject in need thereof, comprising administering to the subject a therapeutically effective amount of a composition comprising pyrvinium pamoate.

2. A composition for use in treating cancer in a subject in need thereof, comprising a therapeutically effective amount of a composition comprising pyrvinium pamoate.

3. A composition for use in the manufacture of a medicament for the prevention or treatment of cancer, comprising a therapeutically effective amount of a composition comprising pyrvinium pamoate.

4. The method or composition for use according to any one of embodiments 1-3, wherein the composition comprising pyrvinium pamoate comprises a salt or a salt hydrate.

5. The method or composition for use according to embodiment 4, wherein the salt comprises an anhydrous dipyrvinium pamoate salt.

6. The method or composition for use according to any one of embodiments 1-5, wherein the composition comprising pyrvinium pamoate further comprises a nanoparticle.

7. The method or composition for use according to embodiment 6, wherein the nanoparticle comprises a liposome, a micelle, a polymer-based nanoparticle, a lipid-polymer based nanoparticle, a metal based nanoparticle, a nanocrystal, a carbon nanotube based nanoparticle or a polymeric micelle.

8. The method or composition for use according to embodiment 7, wherein the polymer-based nanoparticle comprises a multiblock copolymer, a diblock copolymer, a polymeric micelle or a hyperbranched macromolecule.

9. The method or composition for use according to embodiment 7, wherein the polymer-based nanoparticle comprises a multiblock copolymer a diblock copolymer.

10. The method or composition for use according to embodiment 7, wherein the polymer-based nanoparticle comprises a poly(lactic-co-glycolic acid) PLGA polymer.

11. The method or composition for use according to any one of embodiments 8-10, wherein the polymer-based nanoparticle is pH responsive.

12. The method or composition for use according to any one of embodiments 7-11, wherein the polymer-based nanoparticle further comprises a buffering component.

13. The method or composition for use according to any one of embodiments 7-12, wherein the nanoparticle further comprises a targeting agent.

14. The method or composition for use according to embodiment 13, wherein the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment.

15. The method or composition for use according to embodiment 13, wherein the targeting agent comprises hyaluronic acid.

16. The method or composition for use according to any one of embodiments 13-15, wherein the targeting agent binds to the surface of a cell of the cancer of the subject.

17. The method or composition for use according to any one of embodiments 13-15, wherein the targeting agent increases uptake of the nanoparticle by a cancer cell of the subject.

18. The method or composition for use according to any one of embodiments 1-167, wherein the cancer comprises a colon cancer, a breast cancer, a liver cancer, a lung cancer, a brain cancer, a pancreatic cancer or a renal cancer.

19. The method or composition for use according to embodiment 18, wherein the lung cancer comprises a small cell lung cancer or a non-small cell lung cancer.

20. The method or composition for use according to any one of embodiments 1-17, wherein the cancer is a rare cancer.

21. The method or composition for use according to embodiment 20, wherein the rare cancer is a blastoma, a glioma, a sarcoma, a carcinoma, a neuroendocrine cancer, a mesothelioma, a chordoma, a thymic cancer, a gastrointestinal stromal tumor or a pheochromocytoma.

22. The method or composition for use according to embodiment 21, wherein the blastoma comprises a neuroblastoma.

23. The method or composition for use according to embodiment 21, wherein the sarcoma comprises an Ewing's sarcoma, a leiomyosarcoma, an angiosarcoma or a rhabdomyosarcoma.

24. The method or composition for use according to embodiment 21, wherein the carcinoma comprises an adenoid cystic carcinoma (ACC), a uterine serous carcinoma, a cholangiocarcinoma, a colorectal carcinoma, an esophageal carcinoma, a hepatocellular carcinoma, a pancreatic carcinoma, a small cell lung carcinoma, an adrenocortical carcinoma, an ovarian carcinoma, a gastric carcinoma or a thymic carcinoma.

25. The method or composition for use according to embodiment 24, wherein the ovarian carcinoma comprises an endometrioid or epithelial ovarian carcinoma.

26. The method or composition for use according to embodiment 24, wherein the adenoid cystic carcinoma (ACC) comprises a salivary gland cell, a trachea cell, a lacrimal gland cell, a skin cell or a vulval cell.

27. The method or composition for use according to embodiment 21, wherein the neuroendocrine cancer comprises an adrenocortical carcinoma, a carcinoid tumor or a thymic cancer.

28. The method or composition for use according to embodiment 27, wherein the thymic cancer comprises a thymoma or a thymic carcinoma.

29. The method or composition for use according to embodiment 27, wherein the carcinoid tumor comprises a small intestine tumor, an appendix tumor, a tumor of the bronchial system, a brain tumor, colon tumor, a stomach tumor, a gallbladder tumor, a bile duct tumor, an ovarian tumor, a testicular tumor, a bladder tumor, a kidney tumor, a thymic tumor, an eye tumor, an ear tumor or an adrenal tumor.

30. The method or composition for use according to any one of embodiments 1-29, wherein the method of treatment or composition for use further comprises at least one other chemotherapeutic agent.

31. The method or composition for use according to embodiment 30, wherein the composition comprising pyrvinium pamoate and the at least one other chemotherapeutic agent exhibit synergy.

32. The method or composition for use according to embodiment 31, wherein the synergy is measured using the Chou-Talalay method in at least one cancer cell line.

33. The method or composition for use according to embodiment 32, wherein the synergy comprises a CI of less than 0.9 when measured at at least three concentrations of the composition comprising pyrvinium pamoate and the at least one other chemotherapeutic agent in at least one cancer cell line.

34. The method or composition for use according to any one of embodiments 30-33, wherein the at least one other chemotherapeutic agent comprises a taxane.

35. The method or composition for use according to embodiment 34, wherein the taxane comprises Paclitaxel or Docetaxel.

36. The method or composition for use according to any one of embodiments 30-33, wherein the at least one other chemotherapeutic agent comprises a Vinca alkaloid.

37. The method or composition for use according to embodiment 36, wherein the Vinca alkaloid comprises Vinblastine, Vincristine or Vinorelbine.

38. The method or composition for use according to any one of embodiments 30-33, wherein the at least one other chemotherapeutic agent comprises a platinum based antineoplastic drug.

39. The method or composition for use according to embodiment 38, wherein the platinum based antineoplastic drug comprises Cisplatin, Carboplatin or Oxaliplatin.

40. The method or composition for use according to any one of embodiments 30-33, wherein the at least one other chemotherapeutic agent comprises a Topoisomerase inhibitor.

41. The method or composition for use according to embodiment 40, wherein the topoisomerase inhibitor comprises Irinotecan or Etoposide.

42. The method or composition according to any one of embodiments 30-33, wherein the at least one other chemotherapeutic agent comprises a thymidylate synthase inhibitor.

43. The method or composition for use according to embodiment 42, wherein the thymidylate synthase inhibitor comprises 5-Fluorouracil (5-FU).

44. The method or composition according to any one of embodiments 30-33, wherein the at least one other chemotherapeutic agent comprises a DNA intercalating agent.

45. The method or composition for use according to embodiment 44, wherein the DNA intercalating agent comprises Doxorubicin.

46. The method or composition according to any one of embodiments 30-33, wherein the at least one other chemotherapeutic agent comprises a DNA alkylating agent.

47. The method or composition for use according to embodiment 46, wherein the DNA alkylating agent comprises Dacarbazine, Temozolomide, Cyclophosphamide or Ifosfamide.

48. The method or composition according to any one of embodiments 30-33, wherein the at least one other chemotherapeutic agent comprises an agent that binds to DNA and causes DNA damage.

49. The method or composition according to any one of embodiments 30-33, wherein the at least one other chemotherapeutic agent comprises a cyclin dependent kinase (CDK) inhibitor.

50. The method or composition for use according to embodiment 49, wherein the CDK inhibitor comprises an inhibitor of CDK4, an inhibitor of CDK6 or an inhibitor of CDK4 and CDK6.

51. The method or composition for use according to embodiment 49, wherein the CDK inhibitor comprises Abemaciclib (Verzenio), Palbociclib (Ibrance) or Ribociclib (Kisqali).

52. The method or composition according to any one of embodiments 30-33, wherein the at least one other chemotherapeutic agent comprises a mechanistic target of rapamycin kinase (mTOR) inhibitor.

53. The method or composition for use according to embodiment 52, wherein the mTOR inhibitor comprises Rapamycin (Sirolimus), Temsirolimus (Torisel), Everolimus (Afinitor) or Ridaforolimus.

54. The method or composition according to any one of embodiments 30-33, wherein the at least one other chemotherapeutic agent comprises a DNA damaging agent.

55. The method or composition for use according to embodiment 54, DNA damaging agent comprises Gemcitabine.

56. The method or composition according to any one of embodiments 30-33, wherein the at least one other chemotherapeutic agent comprises receptor tyrosine kinase (RTK) inhibitor.

57. The method or composition for use according to embodiment 56, wherein RTK inhibitor comprises erlotinib, imatinib or sorafenib.

58. The method or composition according to any one of embodiments 30-33, wherein the at least one other chemotherapeutic agent comprises a combination chemotherapy.

59. The method or composition for use according to embodiment 58, wherein the combination chemotherapy comprises 7+3, ABVD, AC, AD, ADE, ADOC, BEACOPP, BEP, CAF, CAPIRI, CAPDX, CB, CBI, CEF, CEPP, CFAR, CHOP, CIM, CLAG, CLAG-M, CMC, CMF, COI, CVD, CVP, DHAP, DVD, ECF, ECX, EOF, EOX, EP, EPOCH, EPOCH+R, ESHAP, FAMTX, FC, FCR, FEC, FLAG-IDA, FLO, FLOX, FOLFIRI, FOLFOX, FOLFOXIRI, GEMOX-B, GVD, Hyper-CVAD, ICE, ICE-V, IFL, IROX, LV5FU2, LVSFU-P, MAID, MFL, MINE, MOPP, MP, MPV, MVAC, OFF, PAC, PAD, PCR, PCV, R-MPV, R-GemOx, R-CHOP, R-CVP, R-FCM, RICE, TAC, TC, TCH, TIP, TPC, TPF, VAD, VIP, VMP, VMPT, XELIRI or XELOX.

60. The method or composition for use of any one of embodiments 30-59, wherein the composition comprising pyrvinium pamoate and the at least one other chemotherapeutic agent are in the same composition.

61. The method or composition for use according to embodiment 60, wherein the composition comprising pyrvinium pamoate and the at least one other chemotherapeutic agent are formulated in a nanoparticle.

62. The method or composition for use according to any one of embodiments 30-61, wherein the composition comprising pyrvinium pamoate and the least one other chemotherapeutic agent are administered simultaneously.

63. The method or composition for use according to any one of embodiments 30-59, wherein the composition comprising pyrvinium pamoate and the at least one other chemotherapeutic agent are administered sequentially.

64. The method or composition for use according to any one of embodiments 30-59 or 63, wherein the composition comprising pyrvinium pamoate and the at least one other chemotherapeutic agent are administered in an alternating series.

65. The method or composition for use according to any one of embodiments 30-59, 63 or 64, wherein the composition comprising pyrvinium pamoate and the second composition comprising at least one other chemotherapeutic agent are administered in temporal proximity.

66. The method or composition for use according to any one of embodiments 30-59 or 62-65, wherein the composition comprising pyrvinium pamoate is suitable for oral administration and the at least one other chemotherapeutic agent is suitable for parenteral administration.

67. The method or composition for use according to any one of embodiments 30-59 or 62-65, wherein the composition comprising pyrvinium pamoate is suitable for parenteral administration and the at least one other chemotherapeutic agent is suitable for oral administration.

68. The method or composition for use according to any one of embodiments 30-65, wherein both the composition comprising pyrvinium pamoate and the at least one other chemotherapeutic agent suitable for parenteral administration.

69. The method or composition for use according to any one of embodiments 30-65, wherein both the composition comprising pyrvinium pamoate and the at least one other chemotherapeutic agent are suitable for oral administration.

70. The method or composition for use according to any one of embodiments 66-68, wherein the parenteral administration comprises an injection or an infusion.

71. The method or composition for use according to embodiment 70, wherein the injection comprises a subcutaneous injection, an intraperitoneal injection, an intravenous injection or an intramuscular injection.

72. The method or composition for use according to embodiment 70, wherein the infusion comprises an intravenous infusion.

73. The method or composition for use according to any one of embodiments 1-72, wherein the cancer is a stage 0 or stage 1 (early stage, pre-metastatic) cancer.

74. The method or composition for use according to any one of embodiments 1-72, wherein the cancer is a stage 2 cancer or stage 3 (spread to nearby tissues and lymph nodes) cancer.

75. The method or composition for use according to any one of embodiments 1-72, wherein the cancer is a stage 4 (advanced or metastatic) cancer.

76. The method or composition for use according to any one of embodiments 1-75, wherein the subject is a mammal, a non-human primate or a human.

77. The method or composition for use according to any one of embodiments 1-75, wherein the subject is a human.

78. The method or composition for use according to embodiment 77, wherein the human is a man, a woman, a child (age 1-14 years, inclusive of the final year), a baby (a 2 months to 12 months, inclusive of the final month) or a neonate (age 0 to 2 months, inclusive of the final month).

79. The method or composition for use according to any one of embodiments 1-78, wherein the method of treatment or use of the composition further comprises at least one additional cancer treatment.

80. The method or composition for use according to embodiment 79, wherein the at least one additional cancer treatment comprises a surgical procedure to remove at least one tumor of the cancer, at least one dose of a radiation therapy, or a combination thereof.

81. The method or composition for use according to embodiment 79 or 80, wherein the at least one additional cancer treatment comprises at least one third additional chemotherapeutic agent, a therapeutic antibody, at least one immune checkpoint modulator, a combination thereof.

82. The method or composition for use according to embodiment 81, wherein the at least one third chemotherapeutic agent comprises a cell cycle checkpoint inhibitor, an immune checkpoint modulator, an antimitotic agent, a pro-apoptotic agent, a DNA damaging agent, a combination chemotherapy or an inhibitor of a DNA damage response pathway.

83. The method or composition for use according to embodiment 82, wherein the immune checkpoint modulator comprises Yervoy (Ipilimumab), Opdivo (Nivolumab), Tecentriq (Atezolizumab) or Keytruda (Pembrolizumab).

84. The method or composition for use according to embodiment 82, wherein the at least one third additional chemotherapeutic agent comprises Abitrexate (Methotrexate), Afinitor (Everolimus), Alimta (PEMETREXED), Alkeran (Melphalan), Aredia (Pamidronate), Arimidex (Anastrozole), Aromasin (Exemestane), Arranon (Nelarabine), Beleodaq (Belinostat), BiCNU (Carmustine), Blenoxane (Bleomycin), Bosulif (Bosutinib), Busulfex (Busulfan), Caprelsa (Vandetanib), Carboplatin, Casodex (Bicalutamide), CeeNU (Lomustine), Cerubidine (Daunorubicin), Cisplatin, Clolar (Clofarabine), Cometriq (Cabozantinib), Cosmegen (Dactinomycin), Cotellic (Cobimetinib), CytosarU (Cytarabine), Cytoxan, Dacarbazine, Dacogen (Decitabine), DaunoXome (Daunorubicin Lipid Complex), Decadron (Dexamethasone), Docetaxel, Doxorubicin, DepoCyt (Cytarabine Lipid Complex), Dexamethasone Intensol (Dexamethasone), Dexpak Taperpak (Dexamethasone), Droxia (Hydroxyurea), Eligard (Leuprolide), Ellence (Epirubicin), Eloxatin (Oxaliplatin), Elspar (Asparaginase), Emcyt (Estramustine), Erivedge (Vismodegib), Erwinaze (Asparaginase Erwinia chrysanthemi), Ethyol (Amifostine), Etopophos (Etoposide), Eulexin (Flutamide), Fareston (Toremifene), Farydak (Panobinostat), Faslodex (Fulvestrant), Femara (Letrozole), Firmagon (Degarelix), Fludara (Fludarabine), 5-Fluorouracil, Folex (methotrexate), Folotyn (Pralatrexate Injection), FUDR (floxuridine), Gemzar (Gemcitabine), Gilotrif (Afatinib), Gleevec (Imatinib Mesylate), Gliadel (Carmustine), HDAC (high dose Cytarabine), Halaven (Eribulin), Hexalen (Altretamine), Hycamtin (Topotecan), Hycamtin (Topotecan), Hydrea (Hydroxyurea), Ibrance (Palbociclib), Iclusig (Ponatinib), Idamycin PFS (Idarubicin), Ifex (Ifosfamide), Imbruvica (Ibrutinib), Inlyta (Axitinib), Intron A alfab (Interferon alfa-2a), Iressa (Gefitinib), Irinotecan, Istodax (Romidepsin), Ixempra (Ixabepilone), Jakafi (Ruxolitinib), Jevtana (Cabazitaxel Injection), Kyprolis (Carfilzomib), Lenvima (Lenvatinib mesylate), Somatuline Depot (Lanreotide acetate), Leukeran (Chlorambucil), Leukine (Sargramostim), Leustatin (Cladribine), Lonsurf (Trifluridine and Tipiracil), Lupron (Leuprolide), Lupron Depot (Leuprolide), Lupron Depot-PED (Leuprolide), Lynparza (Olaparib), Lysodren (Mitotane), Matulane (Procarbazine), Xofigo (Radium 223 dichloride), Megace (Megestrol), Mekinist (Trametinib), Mesnex (Mesna), Mesnex (Mesna Injection), Metastron (Strontium-89 Chloride), Mexate (Methotrexate) Mustargen (Mechlorethamine), Mutamycin (Mitomycin), Myleran (Busulfan), Navelbine (Vinorelbine), Neosar (Cyclophosphamide), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Odomzo (Sonidegib), Oncaspar (Pegaspargase), Ontak (Denileukin Diftitox), Paclitaxel, Panretin (Alitretinoin), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), RoferonA alfaa (Interferon alfa-2a), Sandostatin (Octreotide), Sandostatin LARDepot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b), Synribo (Omacetaxin), Tabloid (Thioguanine), Taflinar (Dabrafenib), Tarceva (Erlotinib), Targretin (Bexarotene), Tasigna (Nilotinib), Temodar (Temozolomide), Tepadina (Thiotepa), Thalomid (Thalidomide), TheraCys BCG (BCG), Thioplex (Thiotepa), TICE BCG (BCG), Toposar (Etoposide), Torisel (Temsirolimus), Yondelis (Trabectedin), Treanda (Bendamustine hydrochloride), Trelstar (Triptorelin), Trexall (Methotrexate), Trisenox (Arsenic trioxide), Tykerb (Lapatinib), Valstar (Valrubicin Intravesical), Vantas (Histrelin Implant), Velcade (Bortezomib), Vepesid (Etoposide), Vesanoid (Tretinoin), Vincristine, Vidaza (Azacitidine), Vinblastine, Votrient (Pazopanib), Vumon (Teniposide), Wellcovorin IV (Leucovorin), Xalkori (Crizotinib), Xeloda (Capecitabine), Xtandi (Enzalutamide), Zaltrap (Ziv-aflibercept), Zanosar (Streptozocin), Zelboraf (Vemurafenib), Zoladex (Goserelin), Zolinza (Vorinostat), Zometa (Zoledronic acid), Zortress (Everolimus), Zydelig (Idelalisib), Zykadia (Ceritinib), Zytiga (Abiraterone acetate), Vindesine (Eldesine), Raltitrexed (Tomudex), Lometrexol, Satraplatin, Larotaxel, Alectinib (Alecensa), Ixazomib (Ninlaro), Nilotinib (Tasigna), Osimertinib (Tagrisso), Venetoclax (Venclexta), Ribociclib (Kisqali), Enasidenib (Idhifa), Rucaparib (Rubraca), Niraparib (Zejula), Copanlisib (Aliqopa), Neratinib (Nerlynx), Brigatinib (Alunbrig), Midostaurin (Rydapt), Abemaciclib (Verzenio), Rapamycin (Sirolimus), Temsirolimus (Torisel), Ridaforolimus or a combination thereof.

85. The method or composition for use according to embodiment 82, wherein the therapeutic antibody comprises Adcetris (Brentuximab Vedotin), Arzerra (Ofatumumab), Avastin (Bevacizumab), Bexxar (Tositumomab), Bavencio (Avelumab), Blincyto (Blinatumomab), Campath (Alemtuzumab), Cyramza (Ramucirumab), Darzalex (Daratumumab), Empliciti (Elotuzumab), Erbitux (Cetuximab), Gazyva (Obinutuzumab), Imfinzi (Durvalumab), Herceptin (Trastuzumab), Gazyvaro (Obinutuzumab), Kadcyla (Ado-trastuzumab Emtansine), Keytruda (Pembrolizumab), Lartruvo (Olaratumab), Mylotarg (Gemtuzumab Ozogamicin), Ocrevus (Ocrelizumab), Opdivo (Nivolumab), Perjeta (Pertuzumab), Portrazza (Necitumumab), Proxinium (Catumaxomab), Removab (Catumaxomab), Rituxan (Rituximab), Sylvant (Siltuximab), Tecentriq (Atezolizumab), Unituxin (Dinutuximab), Vectibix (Panitumumab), Yervoy (Ipilimumab), Xgeva (Denosumab), Zevalin (Ibritumomab Tiuxetan), Mogamulizumab (Poteligeo) or a combination thereof.

86. The method or composition for use according to embodiment 82, wherein the combination chemotherapy comprises 7+3, ABVD, AC, AD, ADE, ADOC, BEACOPP, BEP, CAF, CAPIRI, CAPDX, CB, CBI, CEF, CEPP, CFAR, CHOP, CIM, CLAG, CLAG-M, CMC, CMF, COI, CVD, CVP, DHAP, DVD, ECF, ECX, EOF, EOX, EP, EPOCH, EPOCH+R, ESHAP, FAMTX, FC, FCR, FEC, FLAG-IDA, FLO, FLOX, FOLFIRI, FOLFOX, FOLFOXIRI, GEMOX-B, GVD, Hyper-CVAD, ICE, ICE-V, IFL, IROX, LV5FU2, LVSFU-P, MAID, MFL, MINE, MOPP, MP, MPV, MVAC, OFF, PAC, PAD, PCR, PCV, R-MPV, R-GemOx, R-CHOP, R-CVP, R-FCM, RICE, TAC, TC, TCH, TIP, TPC, TPF, VAD, VIP, VMP, VMPT, XELIRI or XELOX.

87. The method or composition for use according to embodiment 80, wherein the composition comprising pyrvinium pamoate is suitable for administration at the same time as the at least one dose of radiation therapy.

88. The method or composition for use according to embodiment 80, wherein the composition comprising pyrvinium pamoate is suitable for administration prior to the at least one dose of radiation therapy.

89. The method or composition for use according to embodiment 80, wherein the composition comprising pyrvinium pamoate is suitable for administration after the at least one dose of radiation therapy.

90. The method or composition for use according to embodiment 80, wherein the composition comprising pyrvinium pamoate is suitable for administration in temporal proximity to the at least one dose of radiation therapy.

91. The method or composition for use according to embodiment 80, wherein the surgical procedure to remove at least one tumor of the cancer removes the entire tumor.

92. The method or composition for use according to embodiment 80, wherein a surgical procedure to remove at least one tumor of the cancer removes a part of the tumor.

93. The method or composition for use according to any one of embodiments 80-92, wherein the method of treatment or composition for use further comprises an adoptive cell therapy, a therapy comprising a viral vector, or a combination thereof.

94. The method or composition for use according to embodiment 93, wherein the adoptive cell therapy comprises a chimeric antigen receptor T cell (CAR-T) therapy.

95. The method or composition for use according to any one of embodiments 1-94, wherein the method of treatment alleviates a sign or a symptom of the cancer.

96. The method or composition for use according to embodiment 95, wherein the alleviation of the sign or the symptom of the cancer comprises a reduction in size of at least one tumor, a reduction in the volume of at least one tumor, a decrease in the number of tumors, a decrease in the number of metastatic lesions of the cancer, a reduction of the rate of growth of the cancer or a remission of the cancer.

97. A composition comprising a synergistic combination of pyrvinium pamoate and at least one additional cancer therapeutic agent.

98. The composition according to embodiment 97, wherein the synergy is measured using the Chou-Talalay method in at least one cancer cell line.

99. The composition according to embodiment 98, wherein the synergy comprises a CI of less than 0.9 when measured at least three concentrations of the additional cancer therapeutic agent and the composition comprising pyrvinium pamoate in at least one cancer cell line.

100. The composition according to any one of embodiments 97-99, wherein the composition comprising pyrvinium pamoate comprises a salt or a salt hydrate.

101. The composition according to embodiment 100, wherein the salt comprises an anhydrous dipyrvinium pamoate salt.

102. The composition according to any one of embodiments 97-101, wherein the at least one additional cancer therapeutic agent comprises Cisplatin, Doxorubicin, Etoposide, Vincristine, Paclitaxel, 5-FU, Irinotecan, Carboplatin, Cyclophosphamide, Gemcitabine, Abemaciclib, Oxaliplatin, Erlotinib, Imatinib or Sorafenib.

103. The composition according to any one of embodiments 97-102, wherein the pyrvinium pamoate is formulated in a nanoparticle.

104. The composition according to any one of embodiments 97-102, wherein the pyrvinium pamoate and the at least one additional cancer therapeutic agent are formulated in a nanoparticle.

105. The composition according to embodiment 103 or 104, wherein the nanoparticle comprises a liposome, a micelle, a polymer-based nanoparticle, a lipid-polymer based nanoparticle, a metal based nanoparticle, a nanocrystal, a carbon nanotube based nanoparticle or a polymeric micelle.

106. The composition according to embodiment 105, wherein the polymer-based nanoparticle comprises a multiblock copolymer, a diblock copolymer, a polymeric micelle or a hyperbranched macromolecule.

107. The according to embodiment 105, wherein the polymer-based nanoparticle comprises a multiblock copolymer a diblock copolymer.

108. The composition according to embodiment 105, wherein the polymer-based nanoparticle comprises a poly(lactic-co-glycolic acid) PLGA polymer.

109. The composition according to any one of embodiments 105-108, wherein the polymer-based nanoparticle is pH responsive.

110. The composition according to any one of embodiments 105-109, wherein the polymer-based nanoparticle further comprises a buffering component.

111. The composition according to any one of embodiments 105-110, wherein the nanoparticle further comprises a targeting agent.

112. The composition according to embodiment 111, wherein the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment.

113. The composition according to embodiment 111, wherein the targeting agent comprises hyaluronic acid.

114. The composition according to any one of embodiments 111-113, wherein the targeting agent binds to the surface of a cell of the cancer of the subject.

115. A pharmaceutical composition, comprising the composition of any one embodiments 97-114 and a pharmaceutically acceptable carrier, diluent or excipient.

116. A combinational therapy for treating cancer, comprising administering a therapeutically effective amount of the composition of any one of embodiments 97-114 to a subject in need thereof.

117. A combinational therapy for treating cancer, comprising administering a synergistically effective amount of the composition of any one of embodiments 97-114 to a subject in need thereof.

118. A composition for use in a combinational therapy to treat cancer, comprising a therapeutically effective amount of the composition comprising pyrvinium pamoate of any one of embodiments 1-29.

119. The composition according to embodiment 118 for use in a combinational therapy, wherein the combinational therapy comprises administering one or more additional cancer therapies to the subject.

120. A kit comprising the composition of any one of embodiments 97-119 and instructions for use in the treatment of cancer.

121. A kit, comprising a therapeutically effective amount of a composition comprising pyrvinium pamoate and instructions for use in the treatment of cancer.

122. The kit of embodiment 121, further comprising at least one additional cancer therapeutic agent.

123. The kit of embodiment 122, wherein the therapeutically effective amount of the composition comprising pyrvinium pamoate comprises a synergistically effective amount of the composition comprising pyrvinium pamoate.

124. The kit of embodiment 122 or 123, wherein the composition comprising pyrvinium pamoate and the at least one additional cancer therapeutic agent exhibit synergy.

125. The kit of any one of embodiments 122-124, wherein the at least one additional cancer therapeutic agent comprises a second chemotherapeutic agent, a combination chemotherapy, a therapeutic antibody, a chimeric antigen receptor T cell (CAR-T) therapy or a combination thereof.

126. The kit of any one of embodiments 122-124, wherein the at least one additional cancer therapeutic agent comprises Paclitaxel, Docetaxel, Vincristine, Vinorelbine, Cisplatin, Carboplatin, Oxaliplatin, Irinotecan, Etoposide, 5-FU, Doxorubicin, Temozolomide, Dacarbazine, Cyclophosphamide, Ifosfamide, Abemaciclib, Gemcitabine, Erlotinib, Imatinib or Sorafenib.

127. The kit of any one of embodiments 121-126, wherein the pyrvinium pamoate is formulated in a nanoparticle.

128. The kit of any one of embodiments 122-127, wherein the pyrvinium pamoate and the at least one additional cancer therapeutic agent are formulated in a nanoparticle.

129. The kit of embodiment 127 or 128, wherein the nanoparticle comprises a PLGA polymer and an HA targeting agent.

EXAMPLES

Example 1: Effect of Pyrvinium Pamoate on Cancer Derived Cell Lines

The effect of pyrvinium pamoate administration on cell lines derived from exemplary cancers was tested. One approach to determining the effectiveness of pyrvinium pamoate in the treatment of cancer comprises in vitro testing. In this approach, cancer cell lines representative of the cancers of the disclosure are cultured in vitro according to standard techniques (see, for example, Human Cell Culture Protocols, Third Edition, R. Mitry and R. D. Hughes, Editors, Humana Press, 2012), and increasing concentrations of pyrvinium pamoate are administered to determine the $IC_{50}$ value. As used herein, the term "$IC_{50}$ value" refers to the concentration of a compound (for example pyrvinium pamoate) wherein cellular viability is reduced by half. The $IC_{50}$ is thus a measure of the effectiveness of a compound in inhibiting a biological process. In this model, cancerous cell lines representative of the various cancers of the disclosures were cultured, treated with pyrvinium pamoate in concentrations ranging, typically, from 0.0001 to 2 µM, and the $IC_{50}$ value was calculated after 72 hours to determine the effectiveness of pyrvinium pamoate in killing the cancer cells.

Several rare cancer tumor cell lines including neuroblastoma, leiomyosarcoma, adrenocortical carcinoma, rhabdomyosarcoma, gastric carcinoma, ovarian carcinoma, chordoma and Ewing's sarcoma were analyzed for sensitivity to pyrvinium pamoate treatment in vitro. Cultured cells were exposed to increasing concentrations of pyrvinium pamoate and viability was measured after 72 hours unless otherwise indicated. In all cases, including those described below, the viable cells were determined using the CellTiter Glo® kit and a dose response curve to calculate the $IC_{50}$ was generated using the PRISM software. Treatment with pyrvinium pamoate (PP) resulted in a significant decrease in cell viability with $IC_{50}$s ranging from 0.002-1 µM suggesting that pyrvinium pamoate may represent a potent anti-cancer agent for several rare cancer indications.

As shown in FIG. 1, the ovarian carcinoma cell line SKOV-3 was treated with nine serial dilutions of pyrvinium pamoate (0-2 µM) for 72 hours. The $IC_{50}$ for the SKOV-3 cell line following treatment of pyrvinium pamoate was calculated to be 0.016 µM.

Figure 2:
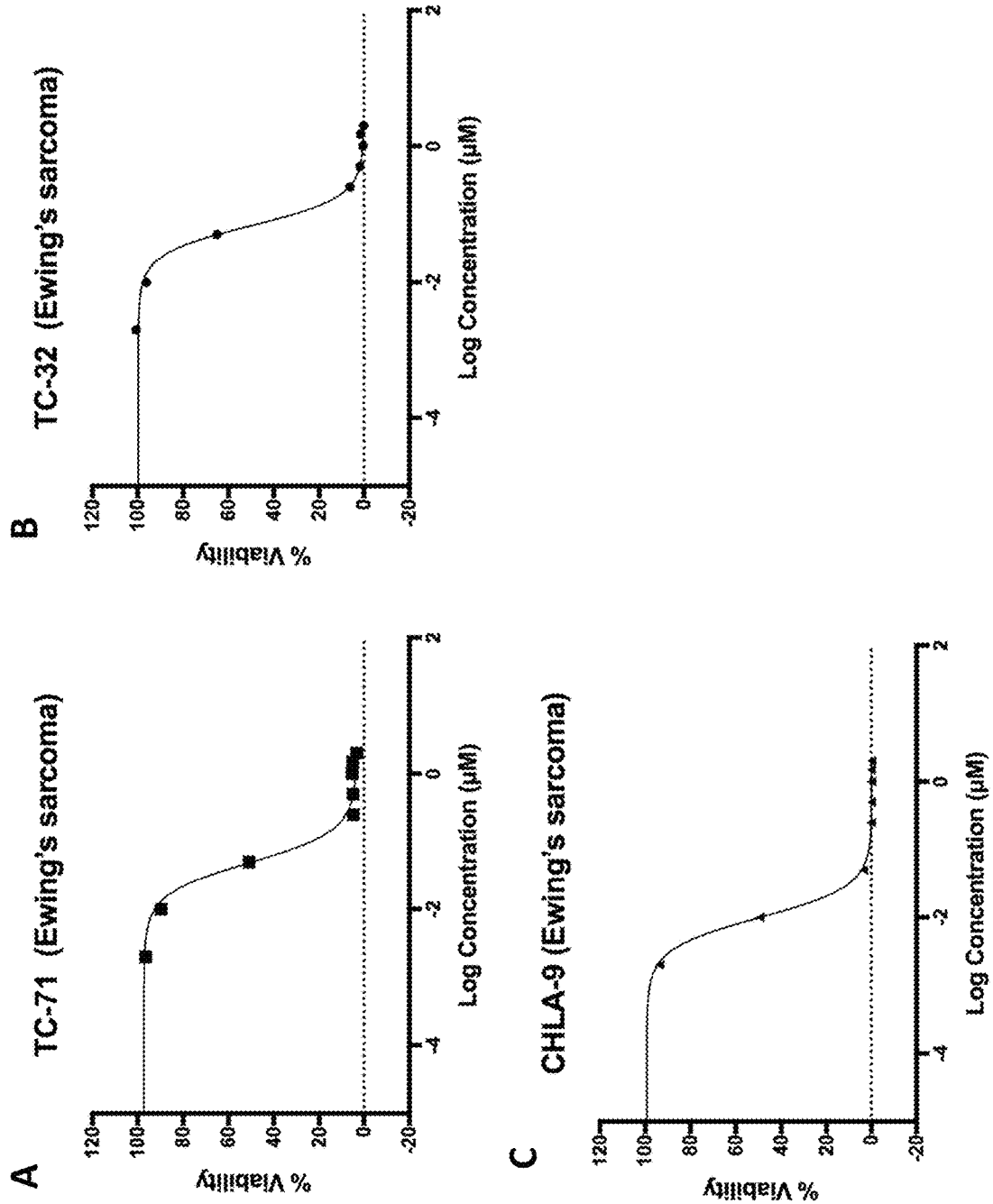
FIG. 2A-C is a series of plots showing the effect of pyrvinium pamoate treatment on cell viability at 72 hours in Ewing's sarcoma cell lines.

As shown in FIG. 2, the Ewing's sarcoma cell lines TC-71, TC-32, and CHLA-9 were treated with nine serial dilutions of pyrvinium pamoate (0-2 µM). An $IC_{50}$ curve was generated. The $IC_{50}$ for the TC-71 cell line following treatment of pyrvinium pamoate was calculated to be 0.0479 µM. The $IC_{50}$ for the TC-32 cell line following treatment of pyrvinium pamoate was calculated to be 0.068 µM. The $IC_{50}$ for the CHLA-9 cell line following treatment of pyrvinium pamoate was calculated to be 0.0099 µM.

Figure 3:
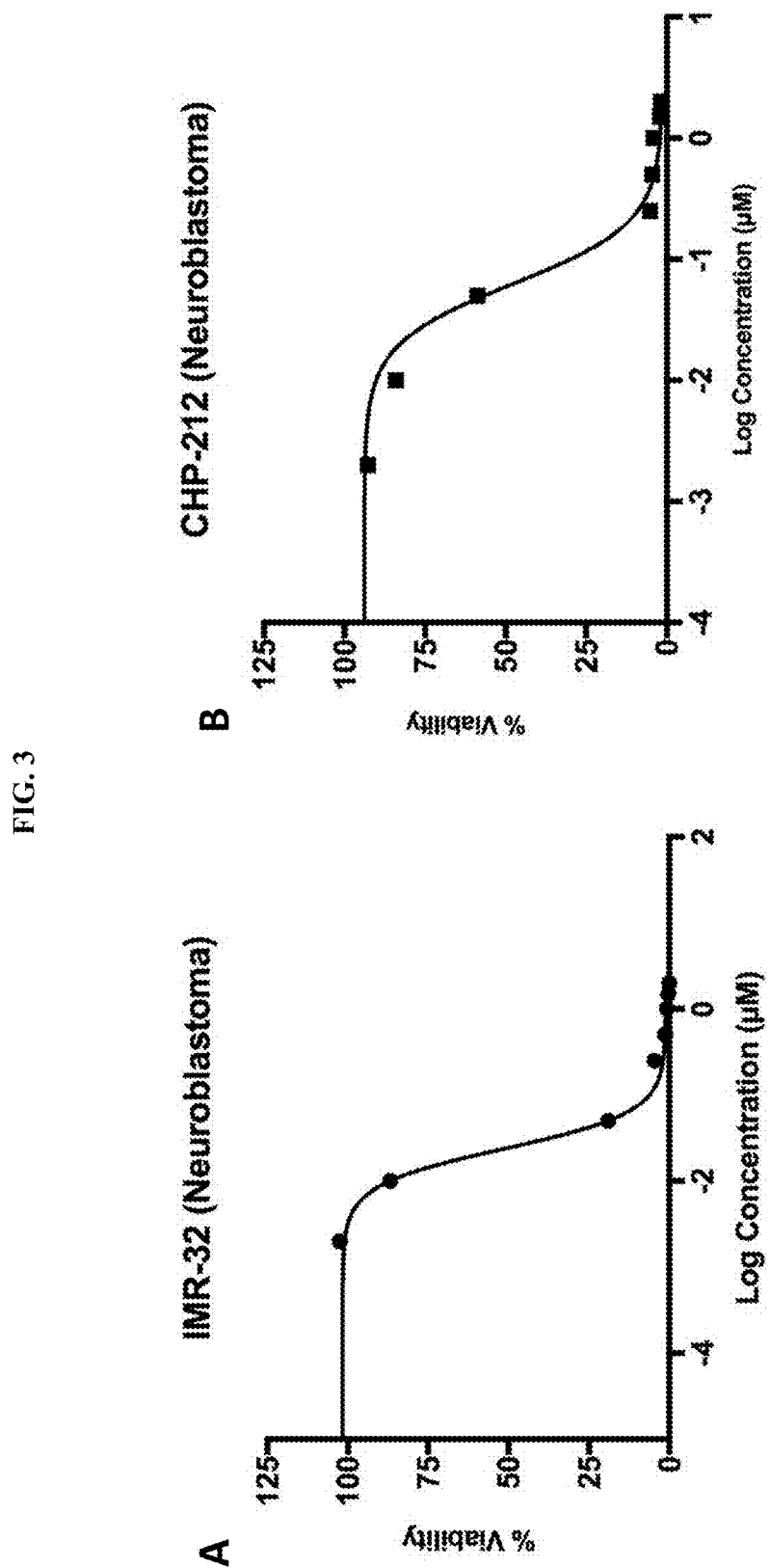
FIG. 3A-B is a series of plots showing the effect of pyrvinium pamoate treatment on cell viability at 72 hours in neuroblastoma cell lines.

As shown in FIG. 3, the neuroblastoma cell lines IMR-32 and CHP-212 were treated with nine serial dilutions of pyrvinium pamoate (0-2 µM) for 72 hours. The $IC_{50}$ for the IMR-32 cell line following treatment of pyrvinium pamoate was calculated to be 0.024 µM. The $IC_{50}$ for the CHP-212 cell line following treatment of pyrvinium pamoate was calculated to be 0.063 µM.

Figure 4:
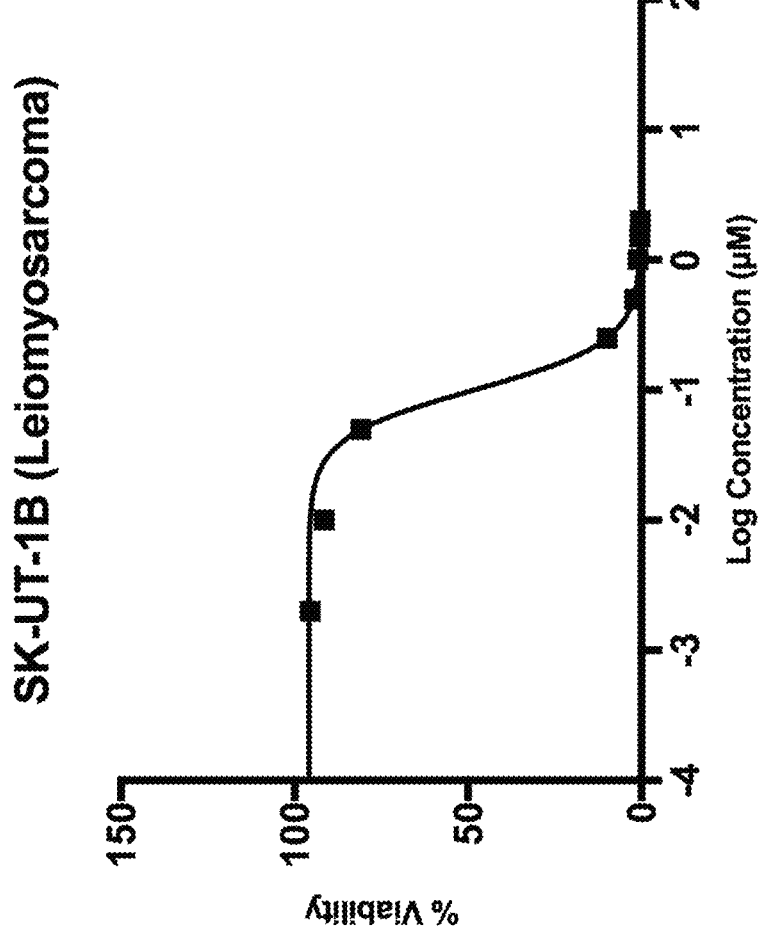
FIG. 4 is a plot showing the effect of pyrvinium pamoate treatment on cell viability at 72 hours in the leiomyosarcoma cell line SK-UT-1B. Cells were treated with nine serial dilutions of pyrvinium pamoate (0-2 µM).

As shown in FIG. 4, the leiomyosarcoma cell line SK-UT-1B cell line was treated with nine serial dilutions of pyrvinium pamoate (0-2 µM) for 72 hours. The $IC_{50}$ for the SK-UT-1B cell line following treatment of pyrvinium pamoate was calculated to be 0.1 µM.

Figure 5:
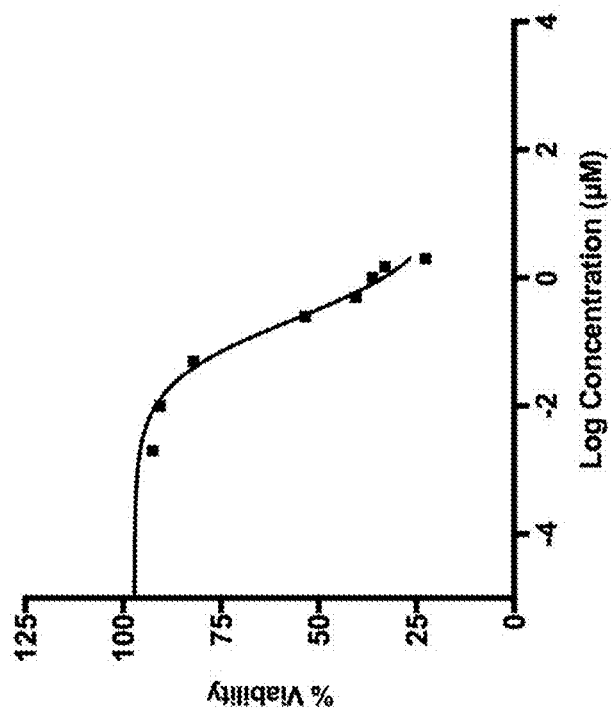
FIG. 5A-B is a series of plots showing the effect of pyrvinium pamoate treatment on cell viability at 72 hours in adrenocortical carcinoma cell lines.
Figure 5:
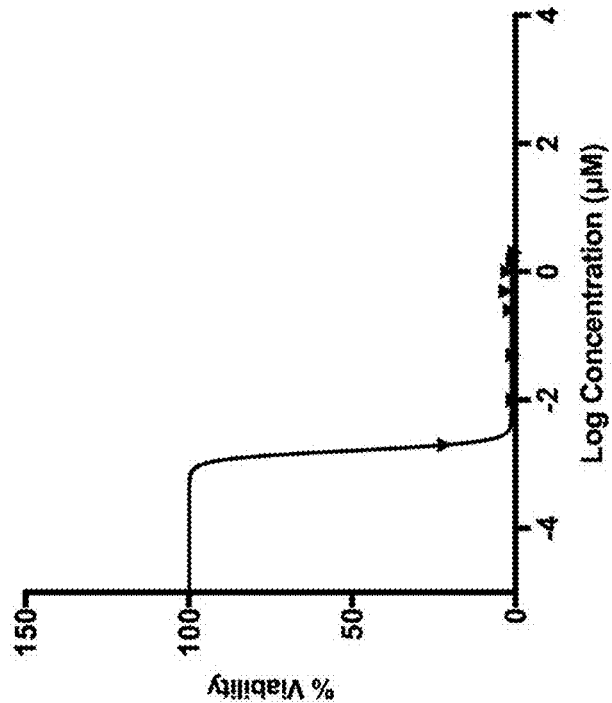

As shown in FIG. 5, the adrenal cortical carcinoma cell lines SW-13 and NCI-H295R were treated with nine serial dilutions of pyrvinium pamoate (0-2 µM) for 72 hours. The $IC_{50}$ for the SW-13 cell line following treatment of pyrvinium pamoate was calculated to be 0.0016 µM. The $IC_{50}$ for the NCI-H295R cell line following treatment of pyrvinium pamoate was calculated to be 0.22 µM.

Figure 6:
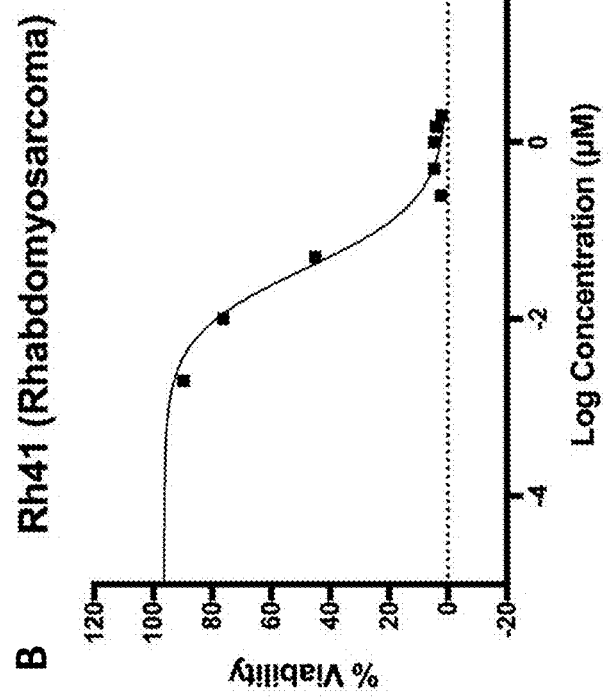
FIG. 6A-B is a series of plots showing the effect of pyrvinium pamoate treatment on cell viability at 72 hours in rhabdomyosarcoma cell lines.
Figure 6:
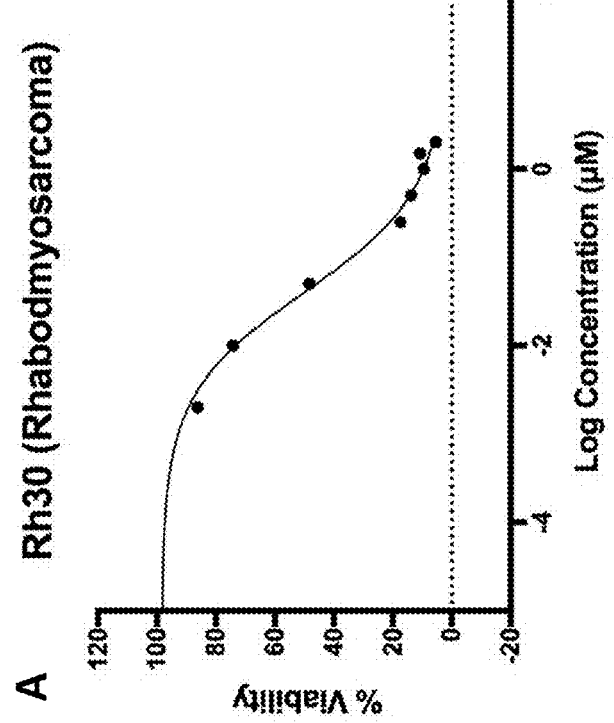

As shown in FIG. 6, the rhabdomyosarcoma cell lines (A) Rh-30 and (B) Rh-41 were treated with nine serial dilutions of pyrvinium pamoate (0-2 µM) for 72 hours. The $IC_{50}$ for the Rh-30 cell line following treatment of pyrvinium pamoate was calculated to be 0.040 µM. The $IC_{50}$ for the Rh-41 cell line following treatment of pyrvinium pamoate was calculated to be 0.0437 µM.

Figure 7:
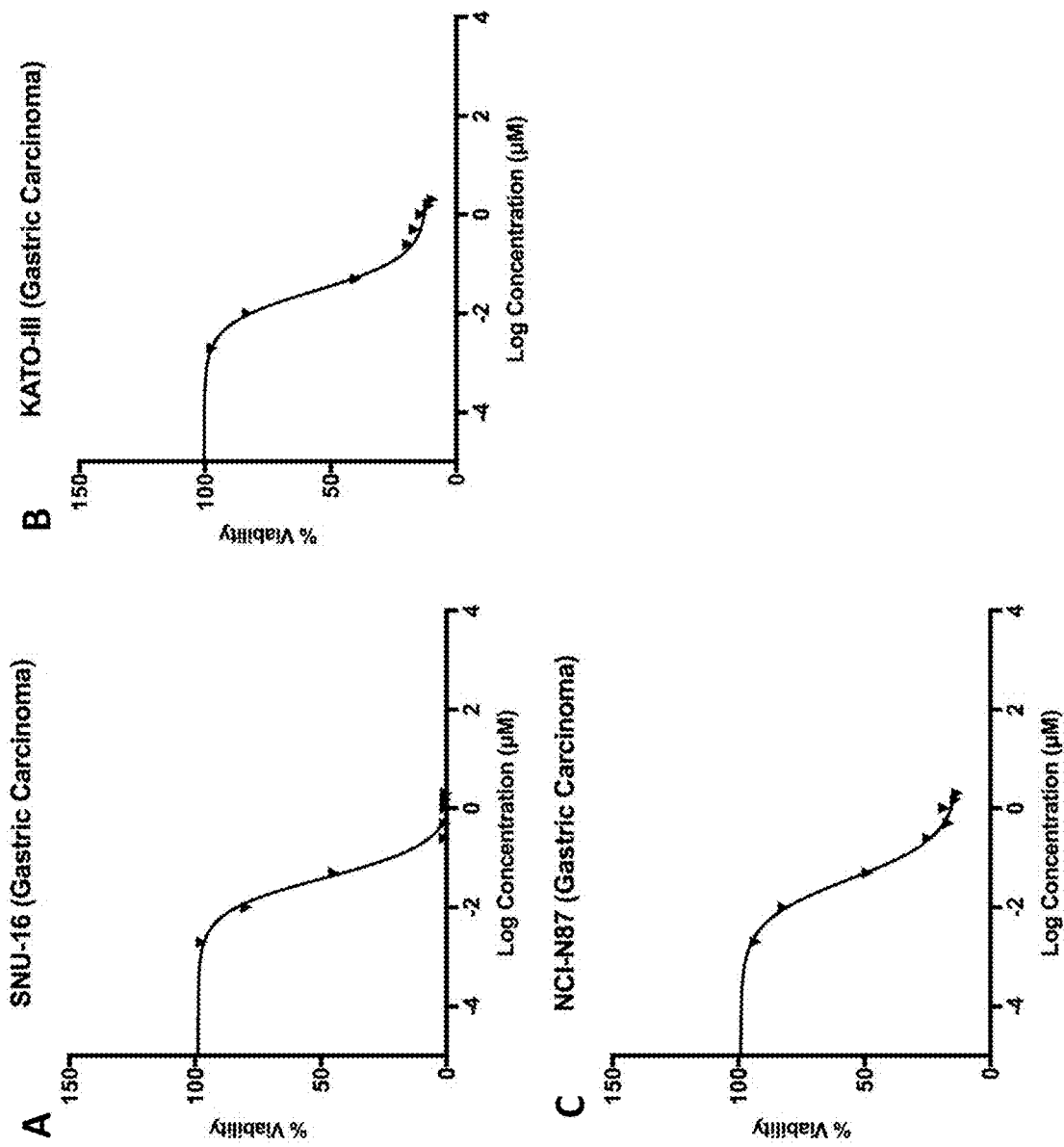
FIG. 7A-C is a series of plots showing the effect of pyrvinium pamoate treatment on cell viability at 72 hours in gastric carcinoma cell lines.

As shown in FIG. 7, the gastric carcinoma cell lines KATO-III, NCI-N87 and SNU-16 were treated with nine serial dilutions of pyrvinium pamoate (0-2 µM) for 72 hours. The $IC_{50}$ for the SNU-16 cell line following treatment of pyrvinium pamoate was calculated to be 0.04 µM. The $IC_{50}$ for the KATO-III cell line following treatment of pyrvinium pamoate was calculated to be 0.029 µM. The $IC_{50}$ for the NCI-N87 cell line following treatment of pyrvinium pamoate was calculated to be 0.038 µM.

Figure 8:
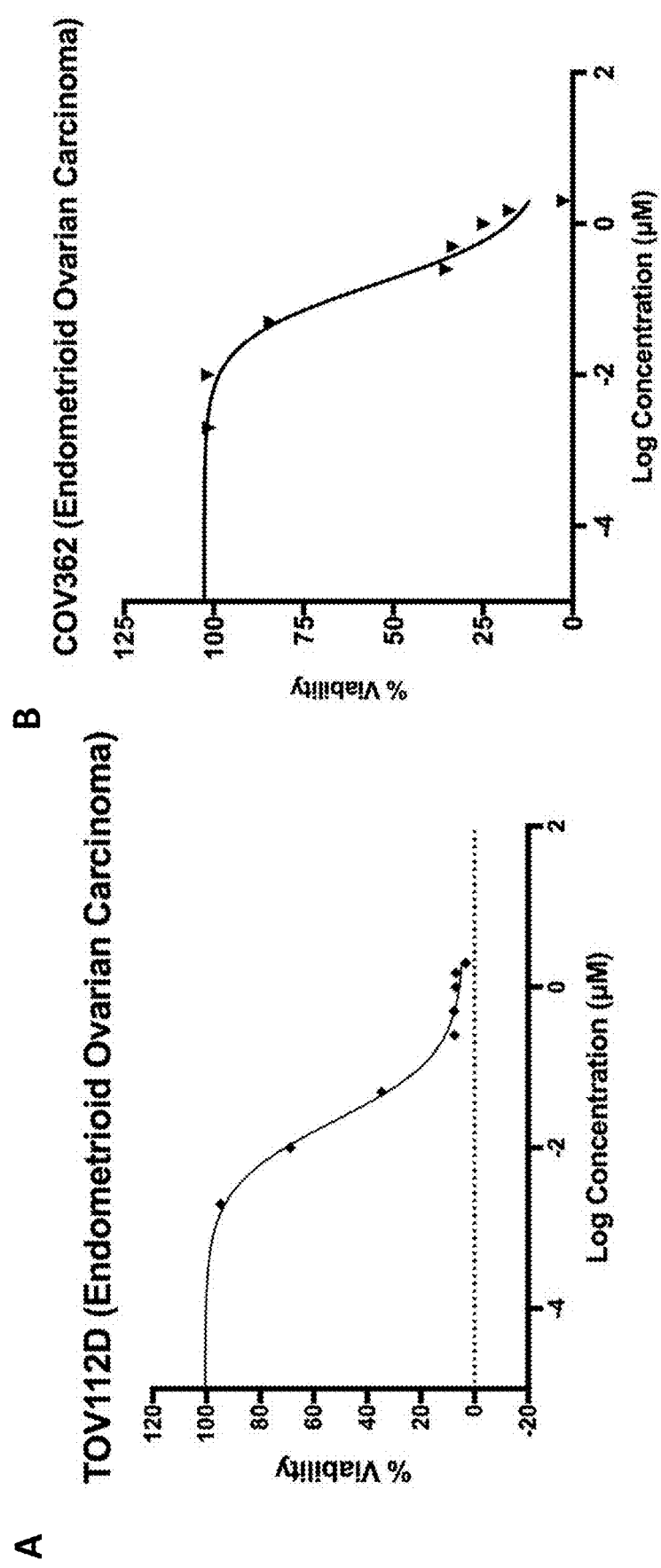
FIG. 8A-B is a series of plots showing the effect of pyrvinium pamoate treatment on cell viability at 72 hours in ovarian carcinoma cell lines.

As shown in FIG. 8, the ovarian carcinoma cell lines (A) TOV112D and (B) COV362, were treated with nine serial dilutions of pyrvinium pamoate (0-2 µM) for 72 hours. The $IC_{50}$ for the TOV112D cell line following treatment of pyrvinium pamoate was calculated to be 0.022 µM. The $IC_{50}$ for the COV362 cell line following treatment of pyrvinium pamoate was calculated to be 0.159 µM.

Figure 9:
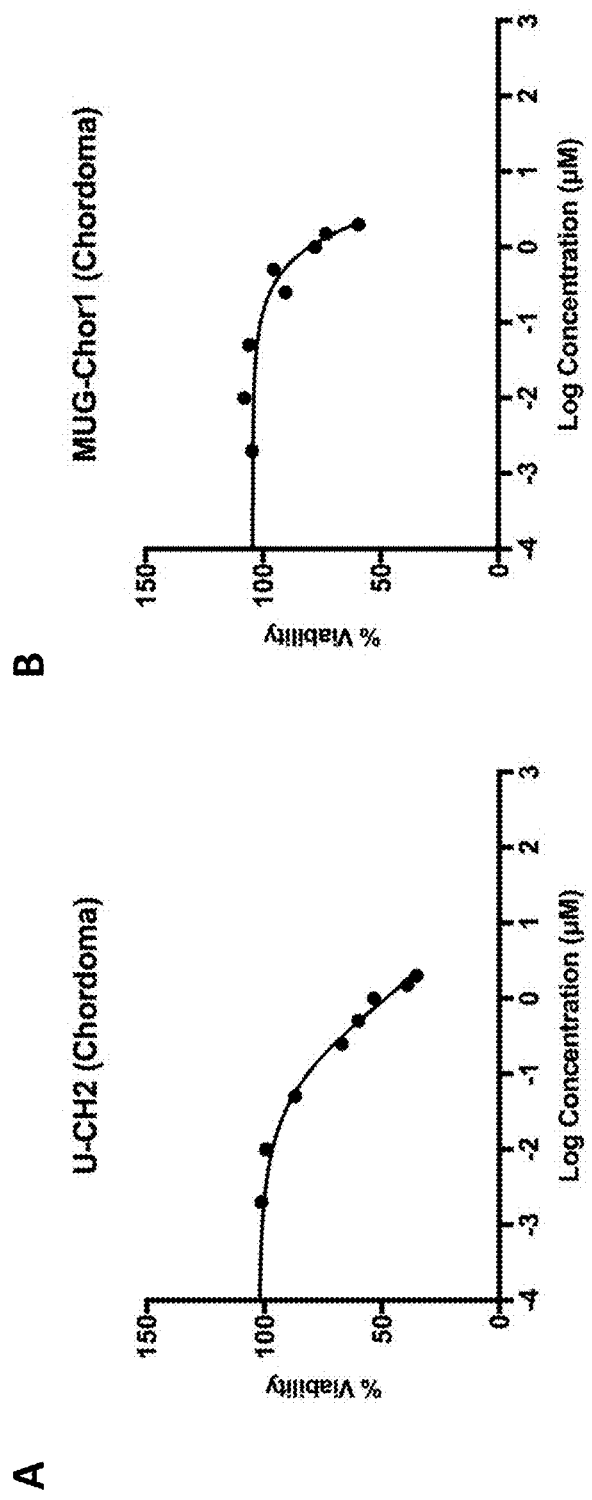
FIG. 9A-B is a series of plots showing the effect of pyrvinium pamoate treatment on cell viability at 72 hours in chordoma cell lines.

As shown in FIG. 9, the chordoma cell lines (A) U-CH2 and (B) MUG-Chor1 were treated with pyrvinium pamoate (0-2 µM) for 72 hours. The $IC_{50}$ for the U-CH2 cell line following treatment of pyrvinium pamoate was calculated to be 0.93 µM. An $IC_{50}$ was not reached with the cell line MUG-Chor1 up to the highest 2 µM concentration of pyrvinium pamoate tested.

Example 2: Synergistic Effect Pyrvinium Pamoate in Combination with Additional Chemotherapeutic Agents in Cancer Derived Cell Lines The $IC_{50}$ values calculated for the response of cell lines to pyrvinium pamoate show the response of these cancer cell lines to pyrvinium pamoate as a monotherapy. Representative cancer cell lines were treated with pyrvinium pamoate and at least one other chemotherapeutic agent, and the resulting $IC_{50}$ values compared to treatment with pyrvinium pamoate alone or the other chemotherapeutic agent alone. In some cases, the effect of the combination of pyrvinium pamoate and the at least one other chemotherapeutic agent resulted in a synergistic effect on the $IC_{50}$ value in these cancer cell lines. In some cases, the effect of the combination of pyrvinium pamoate and the at least one other chemotherapeutic agent was greater than the effects resulting from administration of either pyrvinium pamoate or the other chemotherapeutic agent alone.

FIG. 16 shows an exemplary Latin square showing the results of a synergy assay for pyrvinium pamoate and Paclitaxel. In FIG. 16, increasing concentrations of pyrvinium pamoate and Paclitaxel were added to the gastric cancer cell line SNU16. Cells were incubated for 72 hours at 5% CO2 and 37° C. Cell viability was determined with the Cell Titer Glo assay. Synergy was calculated using the Chou-Talalay method. Synergy was defined as a CI less than <0.9, and the lower the number, the greater the synergy observed.

Additional cancer cell lines were tested, and the results are summarized in tables 5-22 below. For tables 5-22, cells were plated in triplicate and treated with a range of 5 concentrations of pyrvinium pamoate in combination with 5 concentrations of chemotherapeutic agents or small molecules in a complete Latin square. Following a 72 hour incubation, cell viability was determined using Cell Titer Glo. The Combination index (CI) was determined based on the method described by Chou and Talalay (Cancer Res.

2010 Jan. 15; 70(2):440-6. doi: 10.1158/0008-5472.CAN-09-1947. Epub 2010 Jan. 12) with a CI value less than 0.9 indicating synergy. For each cell line tested, synergistic drug combinations were defined as combinations where multiple pairings (greater than or equal to 3) produced a CI<0.9. In each instance where significant synergy was observed, it is documented by Yes and the CI range is indicated.

The CI of pyrvinium pamoate and an additional therapeutic agent such as a chemotherapeutic agent or a small molecule is shown in tables 5-22 below. Entries with more than one CI range indicated are the results of multiple independent assays.

TABLE 5

Assessment of the synergistic activity of pyrvinium pamoate in combination with chemotherapeutic agents in adrenocortical carcinoma.

| Agent | NCI-H295R | SW13 |
| --- | --- | --- |
| Cisplatin | Yes- (0.314-0.798) | Yes- (0.309-0.886) |
| Doxorubicin | Yes- (0.185-0.872) | No |
| Etoposide | Yes- (0.717-0.864) | Yes- (0.487-0.623) |
| Vincristine | Yes- (0.752-0.827) | Yes- (0.499-0.875) |
| Paclitaxel | Yes- (0.571-0.887) | Yes- (0.552-0.870) |
| 5-FU | Yes- (0.529-0.780) | Yes- (0.506-0.834) |
| Irinotecan | Yes- (0.285-0.855) | Yes- (0.652-0.827) |
| Carboplatin | Yes- (0.190-0.896) | Yes- (0.408-0.891) |

Pyrvinium pamoate was tested in combination with Cisplatin, Doxorubicin, Etoposide, Vincristine, Paclitaxel, 5-Fluorouracil (5-FU), Irinotecan or Carboplatin in the adrenocortical carcinoma cell lines NCI-H295R and SW13. Synergy between pyrvinium pamoate and Cisplatin, Etoposide, Vincristine, Paclitaxel, 5-FU, Irinotecan or Carboplatin was observed in both NCI-H295R and SW13 adrenocortical carcinoma cells. Synergy between pyrvinium pamoate and Doxorubicin was observed in NCI-H295R adrenocortical carcinoma cells.

TABLE 6

Assessment of the synergistic activity of pyrvinium pamoate in combination with chemotherapeutic agents in carcinoid tumors.

| Agent | STC-1 |
| --- | --- |
| Cyclophosphamide | Yes- (0.167-0.751) |
| 5-FU | Yes- (0.596-0.841) |
| Cisplatin | Yes- (0.506-0.861) |
| Doxorubicin | Yes- (0.807-0.890) |
| Etoposide | Yes- (0.281-0.794) |
| Vincristine | Yes- (0.036-0.854) |
| Paclitaxel | Yes- (0.479-0.873) |

Pyrvinium pamoate was tested in combination with Cyclophosphamide, 5-FU, Cisplatin, Doxorubicin, Etoposide, Vincristine or Paclitaxel in the carcinoid tumor cell line STC-1. Synergy was observed in all cases. Cyclophosphamide is broken down into the metabolically active form of the drug, 4 hydroperoxycyclophosphamide (4-HC), in the body. Accordingly, in vitro experiments testing Cyclophosphamide activity were performed with 4-HC.

TABLE 7

Assessment of the synergistic activity of pyrvinium pamoate in combination with chemotherapeutic agents in cholangiocarcinoma.

| Agent | CCC-5 | TFK-1 |
| --- | --- | --- |
| 5-FU | Yes- (0.319-0.892) | Yes- (0.303-0.814) |
| Cisplatin | Yes- (0.326-0.892) | Yes- (0.058-0.361) |
| Gemcitabine | Yes- (0.008-0.729) | Yes- (0.290-0.851) |
| Oxaliplatin | Yes- (0.066-0.836) | Yes- (0.450-0.800) |
|  | Yes- (0.380-0.817) |  |
| Vincristine | No | Yes- (0.453-0.827) |
| Paclitaxel | Yes- (0.255-0.847) | Yes- (0.277-0.894) |
|  | Yes- (0.296-0.785) |  |
| Doxorubicin | Yes- (0.341-0.805) | No |
| Abemaciclib | Yes- (0.628-0.841) | Yes- (0.522-0.884) |

Pyrvinium pamoate was tested in combination with 5-FU, Cisplatin, Gemcitabine, Oxaliplatin, Vincristine, Paclitaxel, Doxorubicin or Abemaciclib in the cholangiocarcinoma cell lines CCC-5 and TFK-1. Synergy between pyrvinium pamoate and 5-FU, Cisplatin, Gemcitabine, Oxaliplatin, Paclitaxel or Abemaciclib was observed in both CCC-5 and TFK-1 cholangiocarcinoma cells. Synergy between pyrvinium pamoate and Vincristine was observed in TFK-1 cholangiocarcinoma cells. Synergy between pyrvinium pamoate and Doxorubicin was observed in CCC-5 cholangiocarcinoma cells.

TABLE 8

Assessment of the synergistic activity of pyrvinium pamoate in combination with chemotherapeutic agents in chordoma.

| Agent | UM-Chor1 |
| --- | --- |
| Erlotinib | Yes- (0.308-0.883) |
| Vincristine | Yes- (0.249-0.560) |
| Paclitaxel | Yes- (0.573-0.862) |
| Irinotecan | Yes- (0.580-0.772) |
| Doxorubicin | Yes- (0.423-0.875) |
| Cisplatin | Yes- (0.468-0.887) |
| 5-FU | Yes- (0.489-0.886) |

Pyrvinium pamoate was tested in combination with Erlotinib, Vincristine, Paclitaxel, Irinotecan, Doxorubicin, Cisplatin or 5-FU in the UM-Chor1 chordoma cell line. Synergy was observed in all cases.

TABLE 9

Assessment of the synergistic activity of pyrvinium pamoate in combination with chemotherapeutic agents in colorectal carcinoma.

| Agent | HCT116 | Colo-205 |
| --- | --- | --- |
| 5-FU | Yes- (0.806-0.886) | Yes- (0.094-0.867) |
| Etoposide | Yes- (0.716-0.836) | Yes- (0.107-0.751) |
| Irinotecan | Yes- (0.582-0.878) | Yes- (0.158-0.866) |
| Oxaliplatin | Yes- (0.375-0.889) | Yes- (0.020-0.623) |

Pyrvinium pamoate was tested in combination with 5-FU, Etoposide, Irinotecan or Oxaliplatin in the HCT116 and Colo-205 colorectal carcinoma cell lines. Synergy between pyrvinium pamoate and 5-FU, Etoposide, Irinotecan or Oxaliplatin was observed in both HCT116 and Colo-205 colorectal carcinoma cells.

TABLE 10

Assessment of the synergistic activity of pyrvinium pamoate in combination with chemotherapeutic agents in esophageal carcinoma.

| Agent | Flo-1 | OE-33 |
|---|---|---|
| 5-FU | Yes- (0.378-0.859) | Yes- (0.481-0.715) |
| Carboplatin | Yes- (0.253-0.892) | Yes- (0.647-0.863) |
| Irinotecan | No | Yes- (0.438-0.783) |
| Oxaliplatin | Yes- (0.558-0.871) | Yes- (0.447-0.703) |
| Paclitaxel | Yes- (0.640-0.888) | Yes- (0.527-0.896) |

Pyrvinium pamoate was tested in combination with 5-FU, Carboplatin, Irinotecan, Oxaliplatin or Paclitaxel in the Flo-1 and OE-33 esophageal carcinoma cell lines. Synergy between pyrvinium pamoate and 5-FU, Carboplatin, Oxaliplatin or Paclitaxel was observed in both Flo-1 and OE-33 esophageal carcinoma cells. Synergy between pyrvinium pamoate and Irinotecan was observed in OE-33 esophageal carcinoma cells.

TABLE 11

Assessment of the synergistic activity of pyrvinium pamoate in combination with chemotherapeutic agents in Ewing's sarcoma.

| Agent | TC-32 | TC-71 |
|---|---|---|
| Cyclophosphamide | No | Yes- (0.718-0.722) |
| 5-FU | Yes- (0.337-0.843) | Yes- (0.409-0.821) |
| Carboplatin | Yes- (0.101-0.836) | Yes- (0.597-0.878) |
| Cisplatin | Yes- (0.588-0.878) | Yes- (0.329-0.832) |
| Doxorubicin | Yes- (0.424-0.872) | No |
| Etoposide | Yes- (0.593-0.875) | Yes- (0.677-0.883) |
| Irinotecan | Yes- (0.612-0.764) | Yes- (0.466-0.803) |
| Paclitaxel | Yes- (0.586-0.884) | Yes- (0.254-0.721) |
| Vincristine | Yes- (0.659-0.869) | Yes- (0.251-0.898) |

Pyrvinium pamoate was tested in combination with Cyclophosphamide, 5-FU, Carboplatin, Cisplatin, Doxorubicin, Etoposide, Irinotecan, Paclitaxel or Vincristine in the TC-32 and TC-71 Ewing's sarcoma cell lines. Synergy between pyrvinium pamoate and 5-FU, Carboplatin, Cisplatin, Etoposide, Irinotecan, Paclitaxel or Vincristine was observed in both TC-32 and TC-71 Ewing's sarcoma cells. Synergy between pyrvinium pamoate and Cyclophosphamide was observed in TC-71 Ewing's sarcoma cells. Synergy between pyrvinium pamoate and Doxorubicin was observed in TC-32 Ewing's sarcoma cells.

TABLE 12

Assessment of the synergistic activity of pyrvinium pamoate combination with chemotherapeutic agents in gastric carcinoma.

| Agent | Kato-III | SNU-16 |
|---|---|---|
| 5-FU | No | Yes- (0.547-0.850) |
| Carboplatin | Yes- (0.221-0.887) | Yes- (0.267-0.860) |
|  |  | Yes- (0.261-0.842) |
| Irinotecan | Yes- (0.258-0.892) | No |
| Oxaliplatin | Yes- (0.384-0.781) | Yes- (0.083-0.831) |
|  |  | Yes- (0.089-0.851) |
| Paclitaxel | Yes- (0.076-0.898) | Yes- (0.178-0.820) |
| Doxorubicin | Yes- (0.021-0.584) | Yes- (0.614-0.878) |
| Cisplatin | Yes- (0.386-0.842) | Yes- (0.130-0.862) |
|  |  | Yes- (0.388-0.781) |

Pyrvinium pamoate was tested in combination with 5-FU, Carboplatin, Irinotecan, Oxaliplatin, Paclitaxel, Doxorubicin or Cisplatin in the Kato-III and SNU-16 gastric carcinoma cell lines. Synergy between pyrvinium pamoate and Carboplatin, Oxaliplatin, Paclitaxel, Doxorubicin or Cisplatin was observed in both Kato-III and SNU-16 gastric carcinoma cells. Synergy between pyrvinium pamoate and 5-FU was observed in SNU-16 gastric carcinoma cells. Synergy between pyrvinium pamoate and Irinotecan was observed in Kato-III gastric carcinoma cells.

TABLE 13

Assessment of the synergistic activity of pyrvinium pamoate in combination with chemotherapeutics and small molecule agents in gastrointestinal stromal tumors.

| Agent | GIST-1 |
|---|---|
| Carboplatin | No |
| Cisplatin | Yes- (0.177-0.732) |
| Doxorubicin | Yes- (0.169-0.883) |
| 5-FU | Yes- (0.168-0.798) |
| Imatinib | Yes- (0.203-0.726) |
| Irinotecan | Yes- (0.039-0.837) |
| Paclitaxel | Yes- (0.399-0.808) |
| Vincristine | Yes- (0.231-0.756) |
|  | Yes- (0.150-0.772) |
| Abemaciclib | Yes- (0.249-0.699) |

Pyrvinium pamoate was tested in combination with Carboplatin, Cisplatin, Doxorubicin, 5-FU, Imatinib, Irinotecan, Paclitaxel, Vincristine or Abemaciclib in the GIST-1 gastrointestinal stromal tumor cell line. Synergy was observed between pyrvinium pamoate and Cisplatin, Doxorubicin, 5-FU, Imatinib, Irinotecan, Paclitaxel, Vincristine or Abemaciclib in GIST-1 gastrointestinal stromal tumor cells.

TABLE 14

Assessment of the synergistic activity of pyrvinium pamoate in combination with chemotherapeutic agents or a small molecule agent in hepatocellular carcinoma.

| Agent | HepG2 | HepG2-C3A |
|---|---|---|
| Gemcitabine | Yes- (0.613-0.899) | Yes- (0.201-0.566) |
| Oxaliplatin | Yes- (0.354-0.865) | Yes- (0.307-0.870) |
| Sorafenib | Yes- (0.129-0.843) | Yes- (0.079-0.718) |

Pyrvinium pamoate was tested in combination with Gemcitabine, Oxaliplatin or Sorafenib in the HepG2 and HepG2-C3A hepatocellular carcinoma cell lines. Synergy between pyrvinium pamoate and Gemcitabine, Oxaliplatin or Sorafenib was observed in both HepG2 and HepG2-C3A hepatocellular carcinoma cells.

TABLE 15

Assessment of the synergistic activity of pyrvinium pamoate in combination with chemotherapeutic agents or a small molecule agent in leiomyosarcoma.

| Agent | SK-LMS-1 | SK-UT-1 | SK-UT-1B |
|---|---|---|---|
| Docetaxel | — | Yes- (0.402-0.693) | Yes- (0.536-0.809) |
| Doxorubicin | Yes- (0.492-0.898) Yes- (0.105-0.143) | Yes- (0.556-0.858) | Yes- (0.352-0.739) |
| Gemcitabine | Yes- (0.281-0.850) Yes- (0.311-0.774) | Yes- (0.118-0.888) | Yes- (0.516-0.687) |
| Ifosfamide | No | No | Yes-5 (0.285-0.315) |
| Vincristine | Yes- (0.163-0.831) | — | — |
| Paclitaxel | Yes- (0.078-0.847) | Yes- (0.089-0.330) | Yes-8 (0.262-0.773) |
| Irinotecan | Yes- (0.362-0.885) | No | Yes-8 (0.235-0.705) |
| Cisplatin | Yes- (0.014-0.783) | No | Yes- (0.407-0.742) Yes- (0.337-0.809) |

TABLE 15-continued

Assessment of the synergistic activity of pyrvinium pamoate in combination with chemotherapeutic agents or a small molecule agent in leiomyosarcoma.

| Agent | SK-LMS-1 | SK-UT-1 | SK-UT-1B |
|---|---|---|---|
| Carboplatin | Yes- (0.366-0.812) | — | — |
| 5-FU | Yes- (0.421-0.814) | — | — |
| Abemaciclib | Yes- (0.350-0.808) | — | — |

Pyrvinium pamoate was tested in combination with Doxorubicin, Gemcitabine, Ifosfamide, Paclitaxel, Irinotecan or Cisplatin in the SK-LMS-1, SK-UT-1 and SK-UT-1B leiomyosarcoma cell lines. Synergy between pyrvinium and Doxorubicin, Gemcitabine or Paclitaxel was observed in all three of K-LMS-1, SK-UT-1 and SK-UT-1B leiomyosarcoma cells. Synergy between pyrvinium pamoate and Ifosfamide was observed in SK-UT-1B leiomyosarcoma cells. Synergy between pyrvinium pamoate and Irinotecan or Cisplatin was observed in both K-LMS-1 and SK-UT-1B leiomyosarcoma cells.

Pyrvinium pamoate was tested in combination with Docetaxel in SK-UT-1 and SK-UT-1B leiomyosarcoma cell lines. Synergy between pyrvinium pamoate and Docetaxel was observed in both SK-UT-1 and SK-UT-1B leiomyosarcoma cells.

Pyrvinium pamoate was tested in combination with Vincristine, Carboplatin, 5-FU or Abemaciclib in the K-LMS-1 leiomyosarcoma cell line. Synergy was observed in all cases.

TABLE 16

Assessment of the synergistic activity of pyrvinium pamoate in combination with chemotherapeutic agents in mesothelioma.

| Agent | LO-68 | JU-77 |
|---|---|---|
| Doxorubicin | Yes- (0.008-0.642) | Yes- (0.444-0.889) |
| Carboplatin | Yes- (0.410-0.801) | Yes- (0.385-0.853) |
| Gemcitabine | Yes- (0.047-0.871) | Yes- (0.404-0.725) |
| Vinorelbine | Yes- (0.163-0.845) | Yes- (0.454-0.717) |

Pyrvinium pamoate was tested in combination with Doxorubicin, Carboplatin, Gemcitabine or Vinorelbine in the LO-68 and JU-77 mesothelioma cell lines. Synergy was observed in all cases in both LO-68 and JU-77 mesothelioma cells.

TABLE 17

Assessment of the synergistic activity of pyrvinium pamoate in combination with chemotherapeutic agents or a small molecule agent in neuroblastoma.

| Agent | SK-N-AS | CHP-212 | IMR-32 |
|---|---|---|---|
| Doxorubicin | Yes- (0.082-0.879) | Yes- (0.696-0.812) | — |
| Carboplatin | Yes- (0.107-0.843) | Yes- (0.519-0.846) | — |
| Cisplatin | Yes- (0.130-0.882) | Yes- (0.694-0.756) | — |
| Cyclophosphamide | Yes- (0.098-0.858) | Yes- (0.256-0.876) | — |
| Paclitaxel | Yes- (0.367-0.857) | Yes- (0.545-0.868) | — |
| Vincristine | — | No | — |
| Etoposide | Yes- (0.638-0.834) | Yes- (0.763-0.891) | — |
| Abemaciclib | — | Yes- (0.076-0.772) | Yes- (0.485-0.860) |
| Irinotecan | — | Yes- (0.719-0.891) | — |

Pyrvinium pamoate was tested in combination with Doxorubicin, Carboplatin, Cisplatin, Cyclophosphamide, Paclitaxel or Etoposide in the SK-N-AS and CHP-212 neuroblastoma cell lines. Synergy was observed in all cases in both SK-N-AS and CHP-212 neuroblastoma cells.

Pyrvinium pamoate was tested in combination with Vincristine or Irinotecan in the CHP-212 neuroblastoma cell line. Synergy between pyrvinium pamoate and Irinotecan was observed in CHP-212 neuroblastoma cells. No synergy was observed between pyrvinium pamoate and Vincristine in CHP-212 neuroblastoma cells.

Pyrvinium pamoate was tested in combination with Abemaciclib in the CHP-212 and IMR-32 neuroblastoma cell lines. Synergy between pyrvinium pamoate and Abemaciclib was observed in both CHP-212 and IMR-32 neuroblastoma cells.

TABLE 18

Assessment of the synergistic activity of pyrvinium pamoate in combination with chemotherapeutic agents or a small molecule agent in ovarian carcinoma.

| Agent | COV362 | TOV-112D | SKOV-3 |
|---|---|---|---|
| Doxorubicin | Yes- (0.021-0.895) | No | Yes- (0.017-0.870) |
| Carboplatin | Yes- (0.447-0.837) | Yes- (0.506-0.845) | — |
| Cisplatin | Yes- (0.443-0.859) | Yes- (0.439-0.845) | — |
| Docetaxel | — | No | — |
| Paclitaxel | Yes- (0.451-0.761) | Yes- (0.104-0.877) | — |
| Vincristine | Yes- (0.432-0.825) | Yes- (0.477-0.858) | — |
| Abemaciclib | Yes- (0.144-0.714) | Yes- (0.463-0.882) Yes- (0.373-0.787) | — |
| Irinotecan | Yes- (0.445-0.697) | Yes- (0.414-0.760) | — |
| 5-FU | Yes- (0.472-0.723) | No | — |

Pyrvinium pamoate was tested in combination with Doxorubicin in the COV362, TOV-112D and SKOV-3 ovarian carcinoma cell lines. Synergy between pyrvinium pamoate and Doxorubicin was observed in COV362 and SKOV-3 ovarian carcinoma cells.

Pyrvinium pamoate was tested in combination with Carboplatin, Cisplatin, Paclitaxel, Vincristine, Abemaciclib, Irinotecan or 5-FU in COV-362 and TOV-112D ovarian carcinoma cell lines. Synergy between pyrvinium pamoate and Carboplatin, Cisplatin, Paclitaxel, Vincristine, Abemaciclib or Irinotecan was observed in both COV362 and TOV-112D ovarian carcinoma cells. Synergy between pyrvinium pamoate and 5-FU was observed in COV362 ovarian carcinoma cells.

Pyrvinium pamoate was tested in combination with Docetaxel in the TOV-112D ovarian carcinoma cell line. No synergy was observed.

TABLE 19

Assessment of the synergistic activity of pyrvinium pamoate in combination with chemotherapeutic agents or a small molecule agent in pancreatic carcinoma.

| Agent | BxPC-3 | Hs766t |
|---|---|---|
| 5-FU | Yes- (0.539-0.785) | Yes- (0.328-0.504) Yes- (0.230-0.589) |
| Cisplatin | Yes- (0.472-0.882) Yes- (0.459-0.775) | Yes- (0.458-0.875) |
| Docetaxel | Yes- (0.014-0.741) | — |
| Gemcitabine | Yes- (0.417-0.851) | Yes- (0.378-0.822) |
| Irinotecan | No | Yes- (0.174-0.851) Yes- (0.051-0.623) |
| Oxaliplatin | Yes- (0.254-0.802) | Yes- (0.340-0.884) |
| Paclitaxel | Yes- (0.613-0.899) | Yes- (0.232-0.830) |

TABLE 19-continued

Assessment of the synergistic activity of pyrvinium pamoate in combination with chemotherapeutic agents or a small molecule agent in pancreatic carcinoma.

| Agent | BxPC-3 | Hs766t |
|---|---|---|
| Vincristine | Yes- (0.347-0.869) | No |
| Abemaciclib | Yes- (0.417-0.895) | Yes- (0.587-0.863) |
|  |  | Yes- (0.304-0.879) |

Pyrvinium pamoate was tested in combination with 5-FU, Cisplatin, Gemcitabine, Irinotecan, Oxaliplatin, Paclitaxel, Vincristine or Abemaciclib in the BxPC-3 and Hs766t pancreatic carcinoma cell lines. Synergy between pyrvinium pamoate and 5-FU, Cisplatin, Gemcitabine, Oxaliplatin, Paclitaxel or Abemciclib was observed in both BxPC-3 and Hs766t pancreatic carcinoma cells. Synergy between pyrvinium pamoate and Irinotecan was observed in Hs766t pancreatic carcinoma cells. Synergy between pyrvinium pamoate and Vincristine was observed in BxPC-3 pancreatic carcinoma cells.

Pyrvinium pamoate was tested in combination with Docetaxel in the BxPC-3 pancreatic carcinoma cell line. Synergy was observed between pyrvinium pamoate and Docetaxel in BxPC-3 pancreatic carcinoma cells.

TABLE 20

Assessment of the synergistic activity of pyrvinium pamoate in combination with chemotherapeutic agents in pheochromocytoma/paraganglioma.

| Agent | PC12 |
|---|---|
| Cyclophosphamide | No |
| Dacarbazine | Yes- (0.550-0.818) |
| Vincristine | Yes- (0.614-0.841) |

Pyrvinium pamoate was tested in combination with Cyclophosphamide, Dacarbazine or Vincristine in the PC12 pheochromocytoma/paraganglioma cell line. Synergy between pyrvinium pamoate and Dacarbazine or Vincristine was observed in PC12 pheochromocytoma/paraganglioma cells.

TABLE 21

Assessment of the synergistic activity of pyrvinium pamoate in combination with chemotherapeutic agents or a small molecule agent in rhabdomyosarcoma.

| Agent | Rh30 | Rh41 |
|---|---|---|
| 5-FU | Yes- (0.001-0.887) | Yes- (0.642-0.831) |
| Cisplatin | Yes- (0.693-0.877) | Yes- (0.130-0.874) |
| Cyclophosphamide | Yes- (0.083-0.786) | Yes- (0.274-0.867) |
| Doxorubicin | Yes- (0.152-0.897) | Yes- (0.145-0.834) |
|  | Yes- (0.781-0.896) | Yes- (0.101-0.831) |
| Irinotecan | Yes- (0.324-0.872) | Yes- (0.068-0.711) |
| Vincristine | Yes- (0.477-0.883) | Yes- (0.284-0.876) |
| Paclitaxel | Yes- (0.362-0.829) | Yes- (0.073-0.876) |
| Carboplatin | Yes- (0.770-0.821) | Yes- (0.162-0.820) |
| Abemaciclib | Yes- (0.148-0.886) | — |

Pyrvinium pamoate was tested in combination with 5-FU, Cisplatin, Cyclophosphamide, Doxorubicin, Irinotecan, Vincristine, Paclitaxel or Carboplatin in the Rh30 and Rh41 rhabdomyosarcoma cell lines. Synergy between pyrvinium pamoate and 5-FU, Cisplatin, Cyclophosphamide, Doxorubicin, Irinotecan, Vincristine, Paclitaxel or Carboplatin was observed in both Rh30 and Rh41 rhabdomyosarcoma cells.

Pyrvinium pamoate was tested in combination with Abemaciclib in the Rh30 rhabdomyosarcoma cell line. Synergy between pyrvinium pamoate and Abemaciclib was observed in Rh30 rhabdomyosarcoma cells.

TABLE 22

Assessment of the synergistic activity of pyrvinium pamoate in combination with chemotherapeutic agents or a small molecule agent in small cell lung carcinoma.

| Agent | DMS-114 | SW-1271 |
|---|---|---|
| Etoposide | No | No |
| Cisplatin | Yes- (0.572-0.883) | Yes- (0.568-0.895) |
| Abemaciclib | Yes- (0.327-0.876) | Yes- (0.183-0.889) |

Pyrvinium pamoate was tested in combination with Etoposide, Cisplatin or Abemaciclib in the DMS-114 and SW-1271 small cell lung carcinoma cell lines. Synergy between pyrvinium pamoate and Cisplatin or Abemaciclib was observed in both DMS-114 and SW-1271 small cell lung carcinoma cells. No synergy was observed between pyrvinium pamoate and Etoposide in either DMS-114 or SW-1271 small cell lung carcinoma cells.

Example 3: Encapsulation of Pyrvinium Pamoate in a PLGA-HA Nanoparticle

Pyrvinium pamoate was formulated in a hyaluronic acid (HA)-poly(lactic-co-glycolic acid (PLGA) nanoparticle to provide superior solubility and delivery to cancer cells. HA on the nanoparticle binds to CD44, a transmembrane glycoprotein expressed by many cancer cells.

In table 23 below, cells were plated in triplicate and treated with pyrvinium pamoate or the molar equivalent amount of pyrvinium pamoate contained within a PLGA-HA nanoparticle (PLGA-HA-Pyrvinium-Pamoate) at increasing doses. Following a 72 hr incubation, cell viability was determined using Cell Titer Glo. An $IC_{50}$ for each treatment was established using the PRISM software.

TABLE 23

Encapsulation of pyrvinium pamoate in a PLGA-HA nanoparticle does not significantly impact its biological activity.

| Cell Line | Pyrvinium Pamoate $IC_{50}$ (mM) | PLGA-HA-Pyrvinium-Pamoate $IC_{50}$ (mM) |
|---|---|---|
| TOV112D | 0.07 | 0.10 |
| COV362 | 0.50 | 0.70 |
| SNU16 | 0.06 | 0.06 |
| SK-LMS-1 | 0.02 | 0.10 |
| MSTO211H | 0.44 | 0.16 |
| CHP212 | 0.06 | 0.38 |
| HS766T | 0.06 | 0.29 |
| BXPC3 | 0.05 | 0.15 |
| RH30 | 0.04 | 0.08 |

The PLGA-HA-Pyrvinium-Pamoate nanoparticle was tested as a nanocrystal formulation. In Table 24 below, cells were plated in triplicate and treated with pyrvinium pamoate or the molar equivalent of pyrvinium pamoate in a nanocrystal formulation at increasing doses. Following a 72 hr incubation, cell viability was determined using Cell Titer Glo. An $IC_{50}$ for each treatment was established using the PRISM software.

TABLE 24

Nanocrystal formulation of pyrvinium pamoate does not significantly impact its biological activity.

| Cell Line | Pyrvinium pamoate $IC_{50}$ (mM) | PLGA-HA-Pyrvinium-Pamoate $IC_{50}$ (mM) |
|---|---|---|
| RH41 | 0.02 | 0.04 |
| TC71 | 0.07 | 0.11 |
| STC-1 | 0.01 | 0.03 |

Synergy between the nanoparticle formulation of Pyrvinium Pamoate as a nanoparticle (PLGA-HA-Pyrvinium-Pamoate) and chemotherapeutic agents was observed in representative rhabdomyosarcoma cell lines.

In table 25 below, cells were plated in triplicate and treated with a range of 5 concentrations of pyrvinium pamoate or PLGA-HA-Pyrvinium-Pamoate nanoparticles containing a molar equivalent of pyrvinium pamoate, and 5 concentrations of relevant chemotherapeutic agents in a complete Latin square. Combination indexes (CI) were determined based on the method described by Chou-Talalay with a CI value less than 0.9 indicating synergy. For each cell line tested, synergistic drug combinations were defined as combinations where multiple pairings (greater than or equal to 3) produced a CI<0.9. Numbers in parentheses represent the range of synergistic CI values for each cell line and drug combination.

TABLE 25

Assessment of the synergistic activity of pyrvinium pamoate nanoparticles (PLGA-HA-Pyrvinium-Pamoate) and chemotherapeutics agents in rhabdomyosarcoma.

| Chemotherapeutic | Rh30 | Rh41 |
|---|---|---|
| Vincristine | Yes- (0.098-0.538) | Yes- (0.125-0.792) |
| | Yes- (0.007-0.071) | Yes- (0.045-0.201) |
| Irinotecan | Yes- (0.592-0.850) | Yes- (0.197-0.892) |
| | Yes- (0.019-0.884) | Yes- (0.0001-0.067) |
| Doxorubicin | Yes- (0.055-0.838) | Yes- (0.057-0.834) |
| | Yes- (0.454-0.614) | Yes- (0.004-0.754) |
| | Yes- (0.004-0.763) | Yes- (0.010-0.847) |

Encapsulation of pyrvinium pamoate in a PLGA-HA nanoparticle. Hyaluronic acid (HA) on the nanoparticle binds to CD44, a transmembrane glycoprotein expressed by many cancer cells, enhancing uptake of pyrvinium pamoate by the cancer cells.

Figure 10:
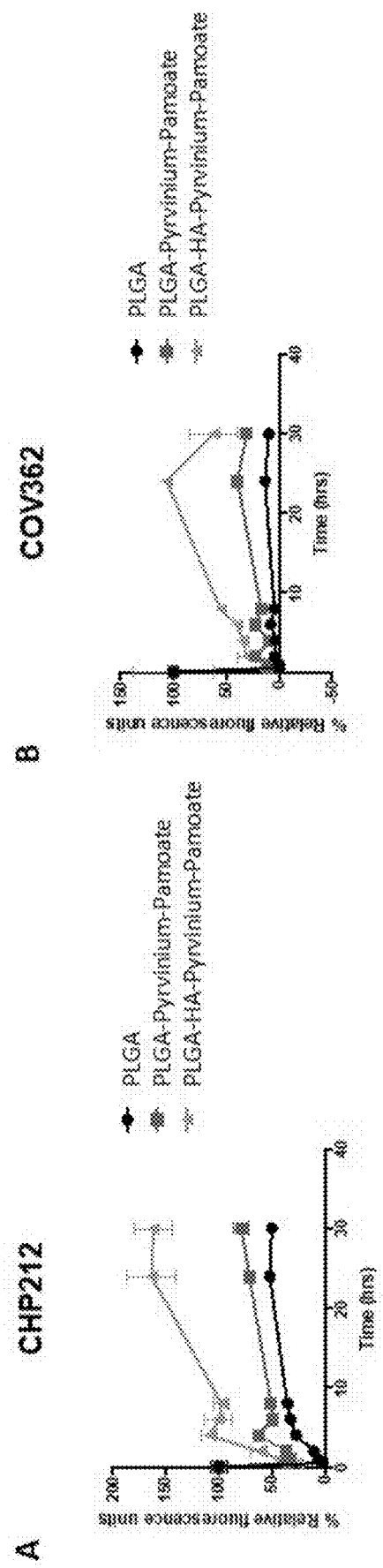
FIG. 10A-B is a pair of plots showing the enhanced uptake of HA-coated pyrvinium pamoate nanoparticles by tumor cells expressing the CD44 ligand.

In FIG. 10, cells from two representative cancer cell lines were tested for nanoparticle uptake. Cells were plated in triplicate and treated with three types of nanoparticles. In FIG. 10, PLGA is a control nanoparticle containing green fluorescent dye, PLGA-Pyrvinium-Pamoate is a nanoparticle containing pyrvinium pamoate along with green fluorescent dye, and PLGA-HA-Pyrvinium-Pamoate is a nanoparticle containing pyrvinium pamoate along with green fluorescent dye and coated with hyaluronic acid (HA) to target CD44 ligand on the surface of tumor cells.

At different time intervals, cells were washed with 1×PBS and the amount of fluorescence internalized was recorded. Data were plotted using PRISM software. Data from two CD44 positive cancer cell lines CHP212 (neuroblastoma) and COV362 (ovarian carcinoma) are shown. Coating with HA to target CD44 significantly enhanced the uptake of nanoparticles into tumor cells.

Figure 11:
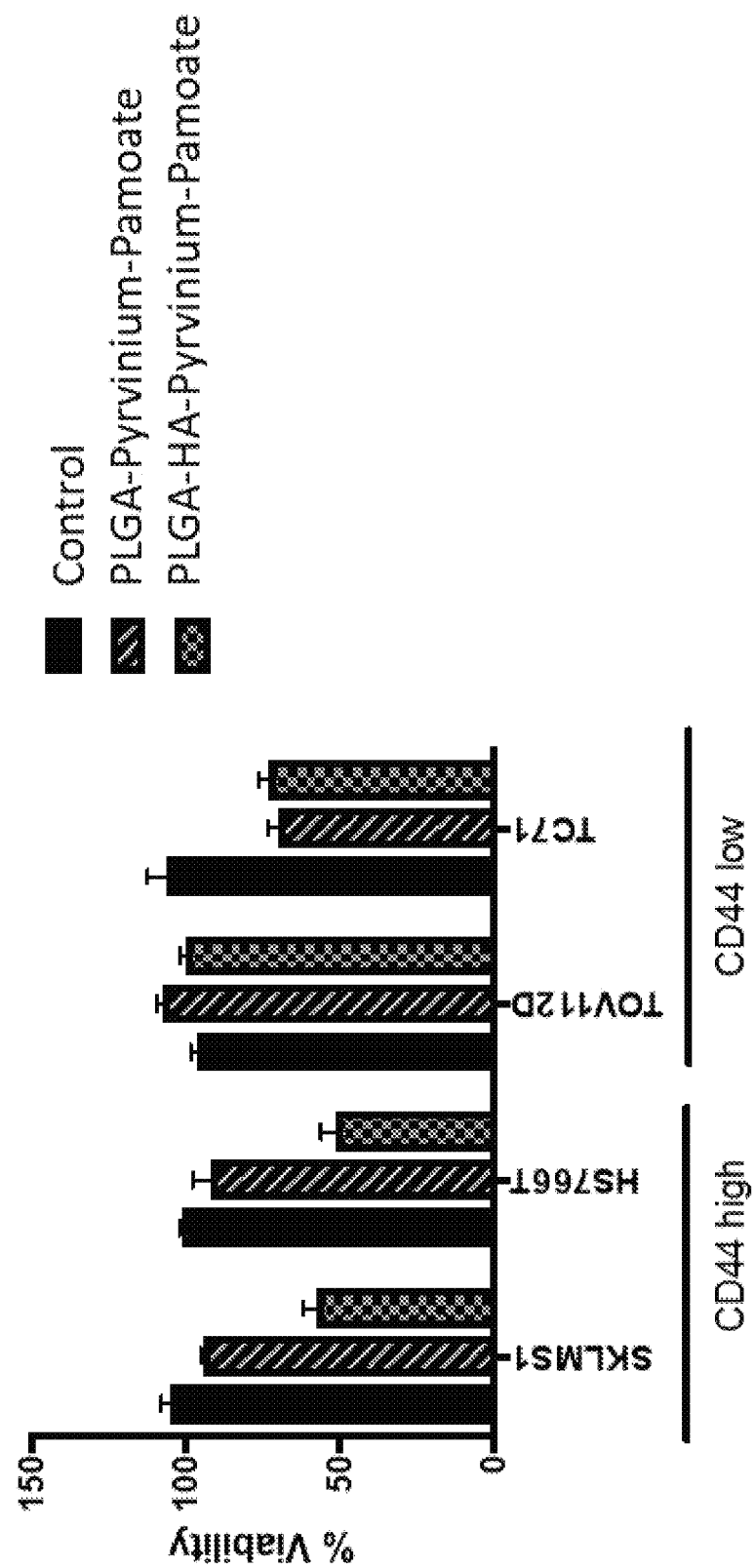
FIG. 11 is a plot showing that HA coating of pyrvinium pamoate nanoparticles enhances cytotoxicity in tumor cells with high levels of CD44 ligand expression.

HA coating of the pyrvinium pamoate nanoparticles also enhanced the cytotoxicity of these nanoparticles in tumor cells with high levels of CD44 ligand expression. In FIG. 11, cells were plated in triplicate and treated with two types of nanoparticles. PLGA-Pyrvinium-Pamoate is a nanoparticle containing pyrvinium pamoate along with green fluorescent dye, and PLGA-HA-Pyrvinium-Pamoate is a nanoparticle containing pyrvinium pamoate along with green fluorescent dye and coated with hyaluronic acid (HA) to target CD44 ligand on the surface of tumor cells. After 8 hours of treatment, cells were washed to remove the nanoparticles which were not taken up by cells. 72 hours later, Cell Titer Glow 2.0 was used to measure cell viability.

Data plotted was using PRISM software. Data from four cancer cell lines with either high or low levels of expression of CD44 are shown. The cancer cell lines with high CD44 expression were SK-LMS-1 (leiomyosarcoma) and Hs766t (pancreatic carcinoma). The cancer cell lines with low CD44 expression were TOV-112D (ovarian carcinoma) and TC-71 (Ewing's sarcoma). HA coating significantly enhanced cytotoxicity of pyrvinium pamoate nanoparticles in tumor cell lines with high levels of CD44 expression.

The exposure level of pyrvinium pamoate (PP) following a single injection of 1 mg/kg of PLGA-HA-Pyrvinium-Pamoate nanoparticle (see FIG. 12). The serum exposure level of pyrvinium pamoate was determined in mice following a single intravenous (iv) administration of 1 mg/kg PP-loaded nanoparticles. As shown in FIG. 12, at six hours post administration, the mean serum concentration of PP in severe combined immune deficiency (SCID) mice (N=3) was 23 nM. This concentration is above the $IC_{50}$ concentration of pyrvinium pamoate for several rare cancer cell lines in vitro. These data show that administration of pyrvinium pamoate in a nanoparticle results in biologically active concentrations of PP in the serum of injected mice.

Figure 13:
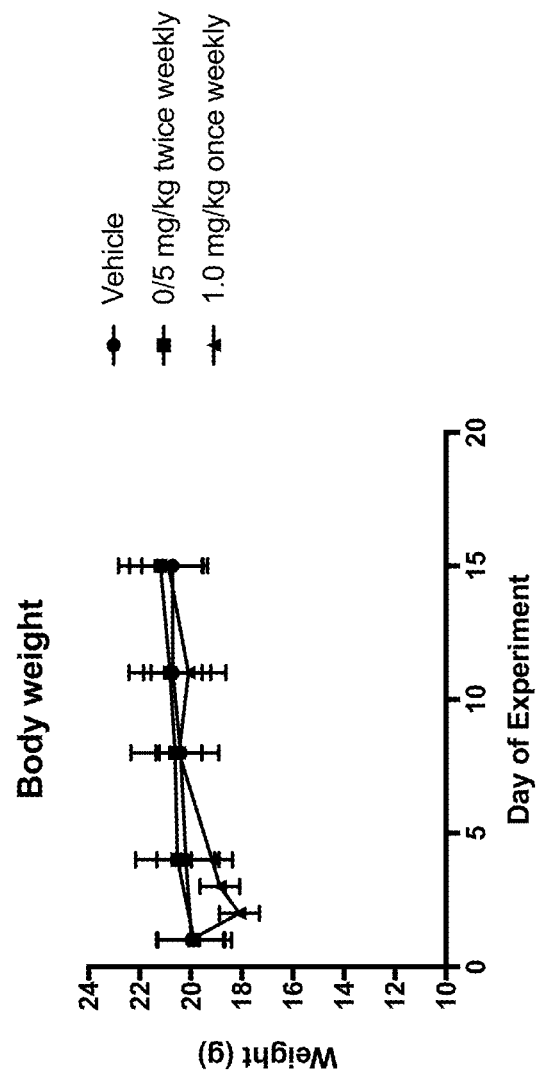
FIG. 13 is a graph showing the tolerability of multiple injections of pyrvinium pamoate contained within nanoparticles administered at 0.5 mg/kg twice weekly and 1.0 mg/kg once weekly in severe combined immune deficiency (SCID) mice.
Figure 14:
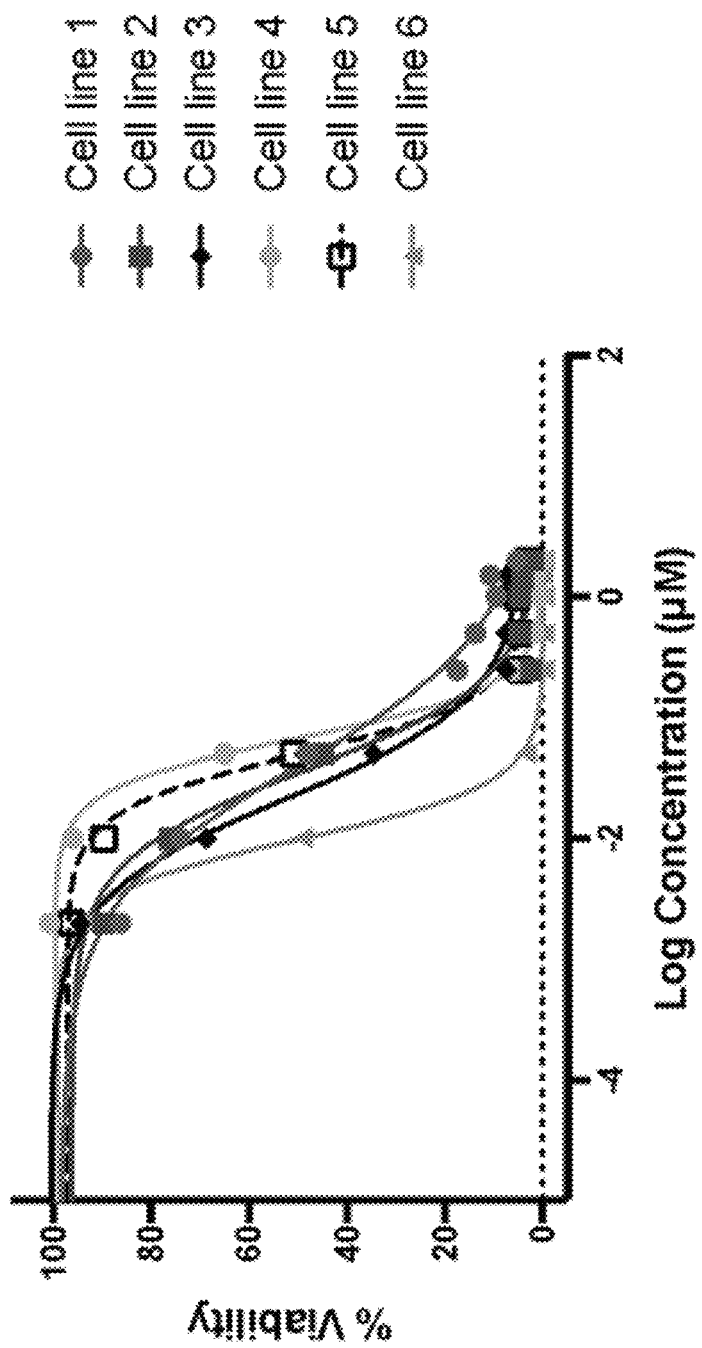
FIG. 14 is a plot showing that treatment with pyrvinium pamoate inhibits growth of multiple rare cancer cell lines.
Figure 17:
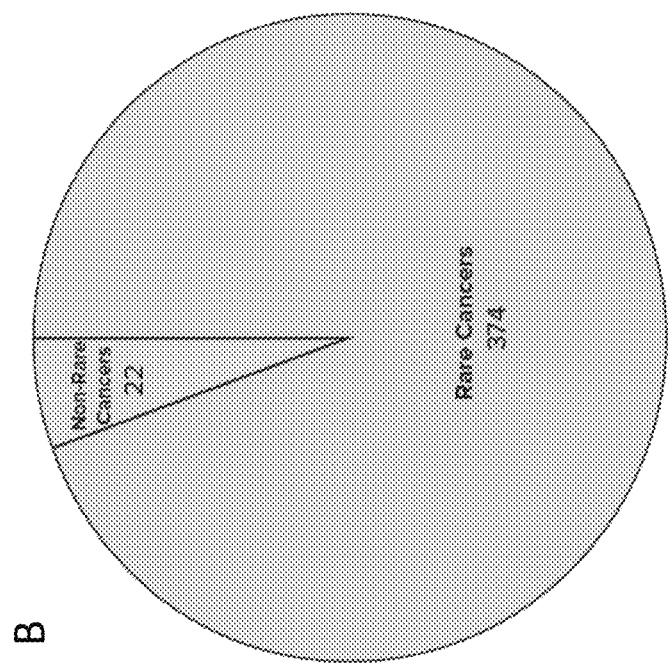
FIG. 17A-B are a pair of pie charts.
Figure 17:
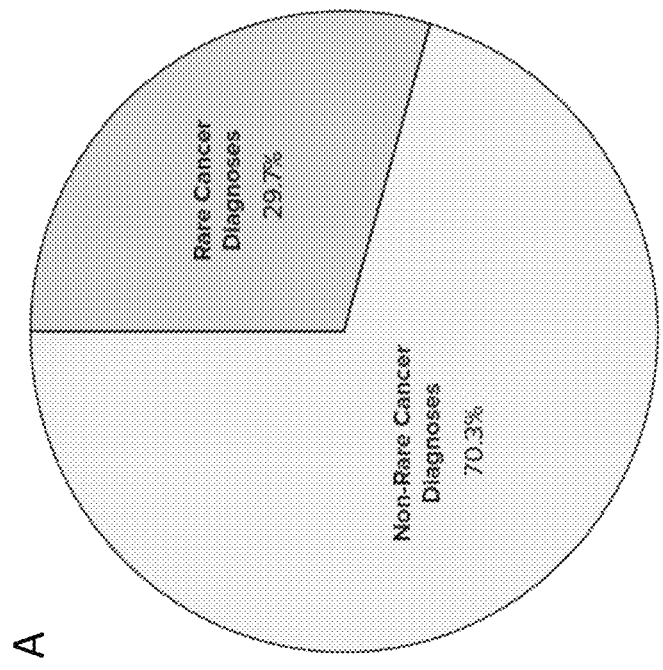
Figure 18:
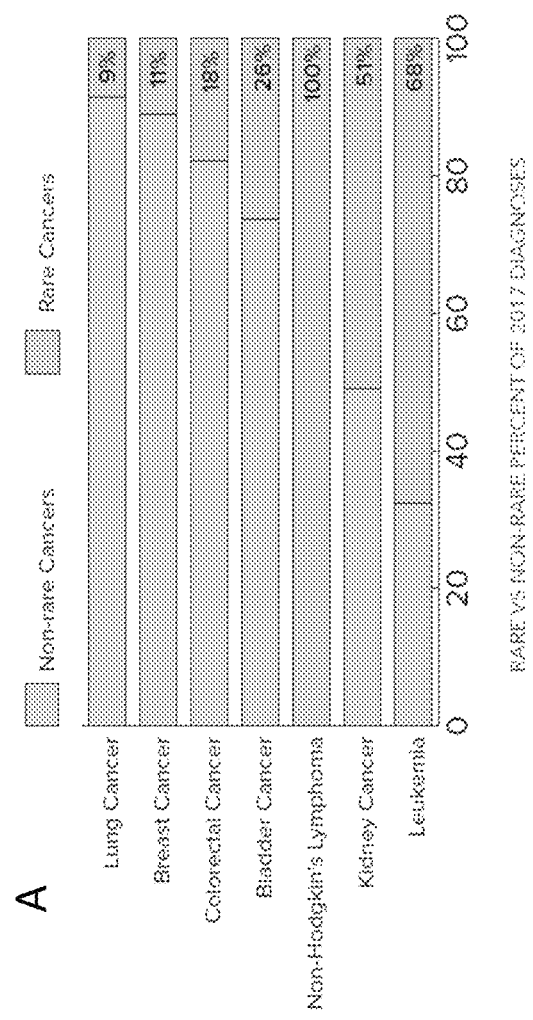
FIG. 18A-B are a graph and a pie chart showing that common cancers are frequently rare.

The tolerability of multiple injections of pyrvinium pamoate (PP) contained within PLGA-HA nanoparticles was also examined in SCID mice. PP nanoparticles were injected intravenously (iv) either once weekly at 1 mg/kg on days 1, 7, and 14, or twice weekly on days 1, 4, 7, 11, and 14 at 0.5 mg/kg. Mice were weighed at multiple timepoints to determine whether administration severely affected body weight as an indicator of toxicity. As shown in FIG. 13, administration of either 1 mg/kg nanoparticles once weekly or 0.5 mg/kg twice weekly was well tolerated by the mice. Although there was a transient decrease in weight following the first injection at 1 mg/kg, mice quickly recovered and weight loss was not observed after the second or third administration. Taken together, these data indicate that following injection of pyrvinium pamoate contained within a nanoparticle, biologically active concentrations of the drug can be detected in circulation. In addition, multiple injections of pyrvinium pamoate contained within a nanoparticle are well tolerated and do not result in sustained weight loss.

Example 4: Incidence of Rare Cancers

Rare cancers are an understudied and deadly public health problem. Estimates for the percentage of cancer diagnoses that are rare vary depending upon the source cited and the definition of what constitutes a rare cancer. Following the NCI definition of a rare disease as affecting fewer than 15 persons per 100,000 per year a cancer affecting 45,691 or fewer is classified as rare. Over 300 rare cancers exist for which there are few treatment options beyond surgical resection representing a significant unmet medical need. Treatment options are currently being explored for several rare cancer indications including repurposing of drugs clinically approved for other indications.

Some of the most severely affected cancer patients are minorities, veterans, those who reside in rural areas, those of the lowest socioeconomic status (SES), those of color, and those who are pediatric patients below the age of 19. At least 64 forms of cancer disproportionately affect veterans and are correlated with service-related exposures such as burn pits and Agent Orange. Between 44-52 of these are defined as rare cancers. Minorities and women are disproportionately affected by dozens of cancers, many of them rare, and frequently face significant economic and social burdens to receiving treatment and participating in clinical trials. Pediatric cancer research receives 4% or less of total NCI funding. Most NCI funding supports discovery-stage basic research and not translational science. All pediatric cancers are rare.

Despite advances in the understanding of the factors involved in promoting tumor growth, up to 87% of rare cancer patients have no treatment options beyond surgical resection, radiation and/or traditional chemotherapy. Repurposing of drugs for use in oncology represents an attractive strategy for the rapid development of therapies that address the significant unmet medical need that remains for rare cancers.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A method of treating a carcinoma selected from the group consisting of adrenocortical carcinoma, cholangiocarcinoma, colorectal carcinoma, esophageal carcinoma, gastric carcinoma, hepatocellular carcinoma, ovarian carcinoma, pancreatic carcinoma and small cell lung carcinoma in a subject in need thereof, comprising administering to the subject a synergistic combination of a composition comprising pyrvinium pamoate, and a composition comprising Cisplatin, Oxaliplatin or Carboplatin.

2. The method according to claim 1, wherein the composition comprising pyrvinium pamoate comprises a salt or a salt hydrate.

3. The method according to claim 1, wherein the composition comprising pyrvinium pamoate further comprises a nanoparticle.

4. The method according to claim 3, wherein the nanoparticle comprises a liposome, a micelle, a polymer-based nanoparticle, a lipid-polymer based nanoparticle, a metal based nanoparticle, a nanocrystal, a carbon nanotube based nanoparticle or a polymeric micelle.

5. The method according to claim 4, wherein the polymer-based nanoparticle comprises a multiblock copolymer, a diblock copolymer, a polymeric micelle or a hyperbranched macromolecule.

6. The method according to claim 4, wherein the polymer-based nanoparticle comprises a poly(lactic-co-glycolic acid) PLGA polymer.

7. The method according to claim 4, wherein the nanoparticle further comprises a targeting agent.

8. The method according to claim 7, wherein the targeting agent comprises a peptide ligand, a nucleotide ligand, a polysaccharide ligand, a fatty acid ligand, a lipid ligand, a small molecule ligand, an antibody, an antibody fragment, an antibody mimetic or an antibody mimetic fragment.

9. The method according to claim 7, wherein the targeting agent comprises hyaluronic acid.

10. The method according to claim 7, wherein the targeting agent binds to the surface of a cell of the carcinoma of the subject.

11. The method according to claim 1, wherein the ovarian carcinoma comprises an endometrioid or epithelial ovarian carcinoma.

12. The method according to claim 1, wherein the synergy is measured using the Chou-Talalay method in at least one carcinoma cell line.

13. The method according to claim 12, wherein the synergy comprises a CI of less than 0.9 when measured at at least three concentrations of the composition comprising pyrvinium pamoate and the composition comprising Cisplatin, Oxaliplatin or Carboplatin in at least one carcinoma cell line.

14. The method according to claim 1, wherein the composition comprising pyrvinium pamoate and the composition comprising Cisplatin, Oxaliplatin or Carboplatin are in the same composition.

15. The method according to claim 14, wherein the composition comprising pyrvinium pamoate and the composition comprising Cisplatin, Oxaliplatin or Carboplatin are formulated in a nanoparticle.

16. The method according to claim 1, wherein the composition comprising pyrvinium pamoate and the composition comprising Cisplatin, Oxaliplatin or Carboplatin are administered simultaneously, are administered sequentially, are administered in alternating series or are administered in temporal proximity.

17. The method according to claim 1, wherein the composition comprising pyrvinium pamoate is administered orally or parenterally, and wherein the composition comprising Cisplatin, Oxaliplatin or Carboplatin is administered parenterally.

18. The method according to claim 17, wherein the parenteral administration comprises a subcutaneous injection, an intraperitoneal injection, an intravenous injection, an intravenous infusion or an intramuscular injection.

19. The method according to claim 1, wherein the carcinoma is a stage 0 or stage 1 pre metastatic carcinoma, a stage 2 or stage 3 carcinoma that has spread to nearby tissues and lymph nodes or a stage 4 advanced or metastatic carcinoma.

20. The method according to claim 1, wherein the subject is a mammal, a non-human primate or a human.

21. The method according to claim 1, wherein the method of treatment further comprises at least one additional carcinoma treatment.

22. The method according to claim 21, wherein the at least one additional carcinoma treatment comprises a surgical procedure to remove at least one tumor of the carcinoma, at least one dose of a radiation therapy, at least one additional chemotherapeutic agent, a therapeutic antibody, at least one immune checkpoint modulator, or a combination thereof.

23. The method according to claim 22, wherein the at least one chemotherapeutic agent comprises a cell cycle checkpoint inhibitor, an immune checkpoint modulator, an anti-mitotic agent, a pro-apoptotic agent, a DNA damaging agent, a combination chemotherapy or an inhibitor of a DNA damage response pathway.

24. The method according to claim 23, wherein the immune checkpoint modulator comprises Ipilimumab, Nivolumab, Atezolizumab or Pembrolizumab.

25. The method according to claim 23, wherein the at least one additional chemotherapeutic agent comprises Methotrexate, Everolimus, Pemetrexed, Melphalan, Pamidronate, Anastrozole, Exemestane, Nelarabine, Belinostat, Carmustine, Bleomycin, Bosutinib, Busulfan, Vandetanib, Carboplatin, Bicalutamide, Lomustine, Daunorubicin, Cisplatin, Clofarabine, Cabozantinib, Dactinomycin, Cobimetinib, Cytarabine, Cytoxan, Dacarbazine, Decitabine, Daunorubicin Lipid Complex, Dexamethasone, Docetaxel, Doxorubicin, Cytarabine Lipid Complex, Hydroxyurea, Leuprolide, Epirubicin, Oxaliplatin, Asparaginase, Estramustine, Vismodegib, Asparaginase *Erwinia chrysanthemi*, Amifostine, Etoposide, Flutamide, Toremifene, Panobinostat, Fulvestrant, Letrozole, Degarelix, Fludarabine, 5-Fluorouracil, Pralatrexate Injection, floxuridine, Gemcitabine, Afatinib, Imatinib Mesylate, Carmustine, high dose Cytarabine, Eribulin, Altretamine, Topotecan, Palbociclib, Ponatinib, Idarubicin, Ifosfamide, Ibrutinib, Axitinib, Interferon alfa-2a, Gefitinib, Romidepsin, Ixabepilone, Ruxolitinib, Cabazitaxel Injection, Carfilzomib, Lenvatinib mesylate, Lanreotide acetate, Chlorambucil, Sargramostim, Cladribine, Trifluridine and Tipiracil, Leuprolide, Olaparib, Mitotane, Procarbazine, Radium 223 dichloride, Megestrol, Trametinib, Mesna, Strontium-89 Chloride, Mechlorethamine, Mitomycin, Vinorelbine, Cyclophosphamide, filgrastim, pegfilgrastim, Sorafenib, nilutamide, Pentostatin, Tamoxifen, Mitoxantrone, Sonidegib, Pegaspargase, Denileukin Diftitox, Alitretinoin, Pomalidomide, Prednisone, Aldesleukin, Mercaptopurine, Zoledronic acid, Lenalidomide, Octreotide, Dasatinib, Regorafenib, Histrelin Implant, Sunitinib, Peginterferon Alfa-2b, Omacetaxin, Thioguanine Dabrafenib, Erlotinib, Bexarotene, Nilotinib, Temozolomide, Thiotepa, Thalidomide, TheraCys BCG, TICE BCG, Temsirolimus, Trabectedin, Bendamustine hydrochloride, Triptorelin, Arsenic trioxide, Lapatinib, Valrubicin Intravesical, Bortezomib, Tretinoin, Vincristine, Azacitidine, Vinblastine, Pazopanib, Teniposide, Leucovorin, Crizotinib, Capecitabine, Enzalutamide, Ziv-aflibercept, Streptozocin, Vemurafenib, Goserelin, Vorinostat, Zoledronic acid, Idelalisib, Ceritinib, Abiraterone acetate, Vindesine, Raltitrexed, Lometrexol, Satraplatin, Larotaxel, Alectinib, Ixazomib, Nilotinib, Osimertinib, Venetoclax, Ribociclib, Enasidenib, Rucaparib, Niraparib, Copanlisib, Neratinib, Brigatinib, Midostaurin, Abemaciclib, Rapamycin, Temsirolimus, Ridaforolimus or a combination thereof.

26. The method according to claim 23, wherein the therapeutic antibody comprises Brentuximab Vedotin, Ofatumumab, Bevacizumab, Tositumomab, Avelumab, Blinatumomab, Alemtuzumab, Ramucirumab, Daratumumab, Elotuzumab, Cetuximab, Obinutuzumab, Durvalumab, Trastuzumab, Obinutuzumab, Ado-trastuzumab Emtansine, Pembrolizumab, Olaratumab, Gemtuzumab Ozogamicin, Ocrelizumab, Nivolumab, Pertuzumab, Necitumumab, Catumaxomab, Catumaxomab, Rituximab, Siltuximab, Atezolizumab, Dinutuximab, Panitumumab, Ipilimumab, Denosumab, Ibritumomab Tiuxetan, Mogamulizumab or a combination thereof.

27. The method according to claim 23, wherein the combination chemotherapy comprises 7+3, ABVD, AC, AD, ADE, ADOC, BEACOPP, BEP, CAF, CAPIRI, CAPDX, CB, CBI, CEF, CEPP, CFAR, CHOP, CIM, CLAG, CLAG-M, CMC, CMF, COI, CVD, CVP, DHAP, DVD, ECF, ECX, EOF, EOX, EP, EPOCH, EPOCH+R, ESHAP, FAMTX, FC, FCR, FEC, FLAG-IDA, FLO, FLOX, FOLFIRI, FOLFOX, FOLFOXIRI, GEMOX-B, GVD, Hyper-CVAD, ICE, ICE-V, IFL, IROX, LV5FU2, LVSFU-P, MAID, MFL, MINE, MOPP, MP, MPV, MVAC, OFF, PAC, PAD, PCR, PCV, R-MPV, R-GemOx, R-CHOP, R-CVP, R-FCM, RICE, TAC, TC, TCH, TIP, TPC, TPF, VAD, VIP, VMP, VMPT, XELIRI or XELOX.

28. The method according to claim 22, wherein the composition comprising pyrvinium pamoate is suitable for administration at the same time as the at least one dose of radiation therapy, prior to the at least one dose of radiation therapy, after the at least one dose of radiation therapy or in temporal proximity to the at least one dose of radiation therapy.

29. The method according to claim 22, wherein the method of treatment further comprises an adoptive cell therapy, a therapy comprising a viral vector, or a combination thereof.

30. The method according to claim 1, wherein the method of treatment alleviates a sign or a symptom of the carcinoma.

31. The method according to claim 1, wherein the carcinoma is pancreatic carcinoma.

* * * * *

UNITED STATES PATENT AND TRADEMARK OFFICE
CERTIFICATE OF CORRECTION

| | | |
|---|---|---|
| PATENT NO. | : 10,933,061 B2 | Page 1 of 1 |
| APPLICATION NO. | : 16/229783 | |
| DATED | : March 2, 2021 | |
| INVENTOR(S) | : Katherine Arline et al. | |

It is certified that error appears in the above-identified patent and that said Letters Patent is hereby corrected as shown below:

In the Claims

At Column 92, Claim number 19, Line number 58:
"noma is a stage 0 or stage 1 pre metastatic carcinoma, a stage"

Should read:
-- noma is a stage 0 or stage 1 pre-metastatic carcinoma, a stage --

At Column 94, Claim number 27, Line number 23:
"ADE, ADOC, BEACOPP, BEP, CAF, CAPIRI, CAPDX"

Should read:
-- ADE, ADOC, BEACOPP, BEP, CAF, CAPIRI, CAPOX --

At Column 94, Claim number 27, Line number 29:
"V, IFL, IROX, LV5FU2, LVSFU-P, MAID, MFL, MINE"

Should read:
-- V, IFL, IROX, LV5FU2, LV5FU-P, MAID, MFL, MINE --

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*